US012661355B2

(12) United States Patent
Vergnes et al.

(10) Patent No.: US 12,661,355 B2
(45) Date of Patent: Jun. 23, 2026

(54) COMPOUNDS AND METHODS FOR INDUCING UCP1 EXPRESSION

(71) Applicant: The Regents of the University of California, Oakland, CA (US)

(72) Inventors: Laurent Vergnes, Oakland, CA (US); Karen Reue, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 783 days.

(21) Appl. No.: 17/917,194

(22) PCT Filed: Apr. 6, 2021

(86) PCT No.: PCT/US2021/025887
§ 371 (c)(1),
(2) Date: Oct. 5, 2022

(87) PCT Pub. No.: WO2021/207135
PCT Pub. Date: Oct. 14, 2021

(65) Prior Publication Data

US 2023/0158028 A1 May 25, 2023

Related U.S. Application Data

(60) Provisional application No. 63/005,763, filed on Apr. 6, 2020.

(51) Int. Cl.
*A61K 31/517* (2006.01)
*A61K 31/454* (2006.01)
*A61P 9/00* (2006.01)

(52) U.S. Cl.
CPC .......... *A61K 31/517* (2013.01); *A61K 31/454* (2013.01); *A61P 9/00* (2018.01)

(58) Field of Classification Search
CPC ............................ A61K 31/517; A61K 31/454
USPC ..................................................... 514/266.24
See application file for complete search history.

(56) References Cited

U.S. PATENT DOCUMENTS 5,939,462 A 8/1999 Connell et al.

FOREIGN PATENT DOCUMENTS

| | | | | |
|---|---|---|---|---|
| WO | WO-98/35944 | A1 | 8/1998 | |
| WO | WO-2008/112715 | A2 | 9/2008 | |
| WO | WO-2012058211 | A2 * | 5/2012 | .............. A61P 25/16 |
| WO | WO-2013/181135 | A1 | 12/2013 | |
| WO | WO-2016/201257 | A2 | 12/2016 | |
| WO | WO-2018046933 | A1 * | 3/2018 | ........... C07D 403/12 |
| WO | WO-2018/146485 | A1 | 8/2018 | |
| WO | WO-2019/140151 | A1 | 7/2019 | |
| WO | WO-2021/207135 | A1 | 10/2021 | |

OTHER PUBLICATIONS

International Search Report and Written Opinion for International Application No. PCT/US2021/025887 dated Jul. 22, 2021.
Invitation to Pay Additional Fees for International Application No. PCT/US2021/025887 mailed Jun. 22, 2021.
Rao et al., "Natural alkaloid bouchardatine ameliorates metabolic disorders in high-fat diet-fed mice by stimulating the sirtuin 1/liver kinase B-1/AMPK axis," Br J Pharmacol, 174(15): 2457-2470 (2017).
Shantz et al., "Targeted overexpression of ornithine decarboxylase enhances beta-adrenergic agonist-induced cardiac hypertrophy," Biochem J, 358: 25-32 (2001).
Vergnes et al., "Induction of UCP1 and thermogenesis by a small molecule via AKAP1/PKA modulation," J Biol Chem, 295(44): 15054-15069 (2020).
El-Sayed et al., "Synthesis and evaluation of anticancer, antiphospholipases, antiproteases, and antimetabolic syndrome activities of some 3H-quinazolin-4-one derivatives" Journal of Enzyme Inhibition and Medicinal Chemistry, vol. 34, No. 1, p. 672-683 (2019).
Extended European Search Report for EP Application No. 21784394.5 dated Mar. 5, 2024.

* cited by examiner

*Primary Examiner* — Yevgeny Valenrod
(74) *Attorney, Agent, or Firm* — Foley Hoag LLP; David P. Halstead; David S. Surry

(57) ABSTRACT

The compounds and methods of the present disclosure exhibit induce Ucp1 transcription, enhance of mitochondrial respiration, activate protein kinase A, increase lipolysis, and increase p38 MAPK phosphorylation in cells, particularly brown adipocytes and white adipocytes. They also protect primary cardiomyocytes against hypertrophy induced by adrenergic agonists. Such compounds and methods are useful in the treatment and prevention of conditions such as obesity and associated complex metabolic, endocrine, and hemodynamic changes, as well as related conditions as dyslipidemias, cardiovascular disease, and type 2 diabetes.

15 Claims, 21 Drawing Sheets

Specification includes a Sequence Listing.

Relative mRNA levels
Ucp1
Zic1
Hoxa5
Ppargc1a
Prdm16
Cidea
Elovl3
Acox1
Cpt1b
Veh
AST070
Z160

OCR (pmol/min/μg protein)
Mitochondrial
Uncoupled
Maximal
Veh
AST
Z160

UCP1
CIDEA
ACADM
CPT1B
ELOVL3
Relative mRNA levels
Veh
Z160
Mitochondrial
Uncoupled
Maximal
OCR (pmol/min/μg protein)
OCR (pmol/min/1000 cells)

| Z160 | AST070 |
|---|---|
| 1.8x | 1.9x |
| 1.4x | 1.3x |
| 1.5x | 1.5x |
| 1.9x | 1.7x |
| 1.2x | 1.2x |

Heart
Sk. muscle
Gon. fat
Ing. fat
BAT
Brain
Liver
Intestine
Testis
PKA RII-β
PKA C-α
AKAP1
AKAP6
GAPDH
52
38
150
102
38

1:4000
μM Z160
0
1
10
50
100
AKAP1
PKA RII-β
PKA C-α
AKAP6
GAPDH
115
50
35
115
30

Veh
Z160
°C
40
41.9
44.9
49.4
55.8
60.3
63.3
PKG-1
p38MAPK
PKA RII-β
PKA C-α
AKAP1
AKAP6
76
52
150
102

Hours
0
2
4
6
8
24
AKAP1
PKA RII-β
PKA C-α
CYTC
GAPDH
Ponceau
150
52
38
17
38

Veh
AST070
Z160
52
IP: α-AKAP1
38
52
Input lysate
38
IB: α-PKA RII-β
IB: α-PKA C-α
IB: α-PKA RII-β
IB: α-PKA C-α

COMPOUNDS AND METHODS FOR INDUCING UCP1 EXPRESSION

RELATED APPLICATION

This application is the U.S. National Stage of International Patent Application No. PCT/US21/25887, filed Apr. 6, 2021, which claims the benefit of priority to U.S. Provisional Patent Application Ser. No. 63/005,763, filed Apr. 6, 2020. Each application is hereby incorporated herein by reference in its entirety.

GOVERNMENT SUPPORT

This invention was made with government support under Grant Number HL028481, awarded by the National Institutes of Health. The government has certain rights in the invention.

REFERENCE TO A SEQUENCE LISTING

This application contains a Sequence Listing in computer readable form. The computer readable form is incorporated herein by reference. Said ASCII copy, created on Jan. 21, 2026, is named UCH-16301_SL.txt and is 11,480 bytes in size.

BACKGROUND

The increasing prevalence of obesity worldwide reflects changes in lifestyle, including a combination of increased food intake and reduced physical activity. Obesity causes complex metabolic, endocrine, and hemodynamic changes that may lead to dyslipidemias, cardiovascular disease and type 2 diabetes [1,2]. Because obesity develops when energy intake exceeds energy expenditure, increasing the latter is an attractive strategy to reduce body weight and fat storage [3,4].

There has been extensive interest in modulating thermogenesis, particularly in brown adipose tissue (BAT) as a treatment for obesity [5-8]. During adaptive thermogenesis, particularly cold exposure, mammals dissipate energy in BAT as heat by decreasing coupling between fatty acid oxidation and ATP synthesis as well as increasing mitochondrial biogenesis. Stored energy in fat is converted to heat, so changes in mitochondrial respiration or in the level of uncoupling activity could promote fat utilization. Recently, the existence of BAT in humans has been reappraised and there is good evidence that brown fat depots are active in adults and are capable of energy dissipation [9-12]. Moreover, adipocytes within white adipose tissue (WAT) may be induced to acquire brown adipocyte characteristics in both animals and humans by recruiting precursor cells or by transdifferentiation [6,13-16]. Thus, human BAT and browning of WAT may be important regulators of body fat accumulation/utilization and potential anti-obesity drug targets.

One key factor in adaptive thermogenesis in BAT is the mitochondrial uncoupling protein-1 (UCP1). UCP1 is responsible for enabling the protein leak in mitochondria that dissipates energy resulting from oxidative metabolism [17,18]. The presence of UCP1 in both classical brown adipocytes and beige adipocytes has spurred interest in targeting UCP1 as a means of increasing energy expenditure. Ucp1 expression is induced by stimulation of the sympathetic nervous system during cold exposure through activation of the β-adrenergic receptor. This leads to cAMP production and activation of protein kinase A (PKA), p38 mitogen-activated protein kinase (p38 MAPK), and transcription factors such as peroxisome proliferator-activated receptor gamma (PPARγ), PPARγ coactivator 1 alpha (PGC1α), and activating transcription factor 2 (ATF2) [17, 19-21]. PKA activation by the second messenger cAMP is critical for the subsequent post-translational modification of transcription factors that induce a thermogenic gene expression program. PKA is a holoenzyme comprised of 2 catalytic and 2 regulatory subunits [22]. PKA is involved in many signaling pathways in different tissues and subcellular compartments. The spatiotemporal organization of PKA activity is facilitated by scaffolding proteins, including A-kinase anchoring proteins (AKAPs). AKAPs compartmentalize PKA to specific subcellular locations such as the cellular membrane, the nucleus, or the mitochondria, allowing distinct substrate phosphorylation and specific signal transmission [23-25]. There has been an interest in targeting AKAP to influence PKA activity [25,26]. In addition, AKAP1 and AKAP13 play a role in the heart, where they have been implicated in protection from cardiac hypertrophy [55,56].

Although the thermogenic pathway and Ucp1 transcriptional effectors have been relatively well characterized, few small molecules have been identified that target Ucp1 expression or activation [7,27,28]. As obesity and other metabolic disorders present a significant challenge to human health, new approaches for treating these conditions are needed.

SUMMARY OF INVENTION

In certain aspects, the compounds and methods of the present invention are useful in the treatment and prevention of conditions such as obesity and associated complex metabolic, endocrine, and hemodynamic changes, as well as related conditions as dyslipidemias, cardiovascular disease, and type 2 diabetes. For example, disclosed herein are methods of treating or preventing a condition, comprising administering to a subject in need thereof an effective amount of a compound of formula (I):

(I)

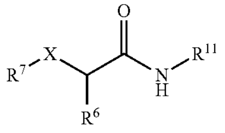

or a tautomer and/or salt thereof;

wherein:

X is S or $CH_2$;

$R^{11}$ is aryl;

$R^6$ is H;

$R^7$ is a quinazolin-4-on-2-yl group, such as

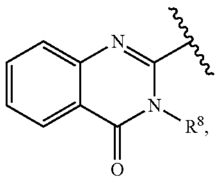

wherein the phenyl ring of the quinazolin-4-on-2-yl group may be substituted or unsubstituted; and $R^8$ is H, $C_{1-5}$ alkyl, $C_{1-5}$ alkenyl, or amino;

or $R^6$ and $R^7$ combine to form an optionally substituted piperidinyl or thiazinanyl ring, including the atoms to which $R^6$ and $R^7$ are attached; and wherein the condition is selected from obesity and associated complex metabolic, endocrine, and hemodynamic changes, dyslipidemias, cardiovascular disease, and type 2 diabetes.

In some aspects, the present disclosure relates to methods of inducing Ucp1 transcription, comprising contacting a cell with a compound of formula (I):

(I)

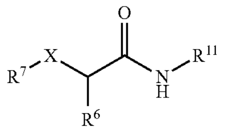

or a tautomer and/or salt thereof;

wherein:

X is S or $CH_2$;

$R^{11}$ is aryl;

$R^6$ is H;

$R^7$ is a quinazolin-4-on-2-yl group, such as

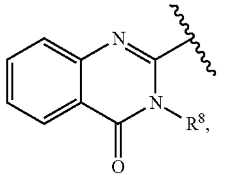

wherein the phenyl ring of the quinazolin-4-on-2-yl group may be substituted or unsubstituted; and $R^8$ is H, $C_{1-5}$ alkyl, $C_{1-5}$ alkenyl, or amino;

or $R^6$ and $R^7$ combine to form an optionally substituted piperidinyl or thiazinanyl ring, including the atoms to which $R^6$ and $R^7$ are attached.

In certain embodiments, $R^{11}$ is a phenyl ring, e.g., substituted with one or more substituents selected from alkyl, alkoxy, aryloxy, aralkoxy, halo, and cyano. In other embodiments, $R^{11}$ is a phenyl ring fused with a dioxane or dioxolane ring, and may optionally be further substituted with one or more substituents, e.g., substituents selected from alkyl, alkoxy, aryloxy, aralkoxy, halo, and cyano.

In certain embodiments, the compound of formula (I) is a compound of formula (Ia):

(Ia)

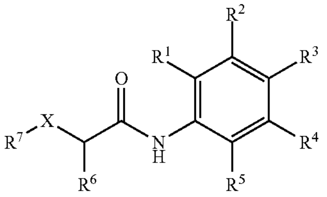

or a tautomer or salt thereof;

wherein:

$R^1$ is H, $C_{1-3}$ alkyl, or $C_{1-3}$ alkoxy;

$R^2$ is H or $C_{1-3}$ alkoxy;

$R^3$ is H, $C_{1-3}$ alkoxy, phenoxy, or benzyloxy;

$R^4$ is H, hydroxyl, $C_{1-3}$ alkoxy, or $C_{1-3}$ haloalkoxy;

or $R^3$ and $R^4$ combine to form a dioxane or dioxolane ring, including the atoms to which $R^3$ and $R^4$ are attached; and $R^5$ is H or $C_{1-3}$ alkyl.

In certain preferred embodiments, the compound of formula (Ia) is

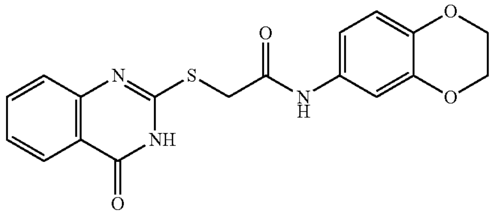

or

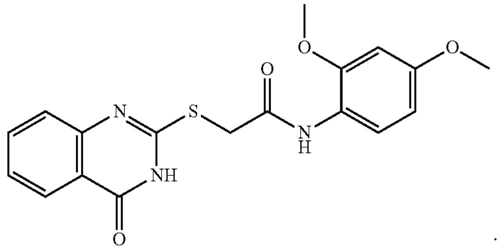

.

The present disclosure further relates to methods of enhancing mitochondrial respiration, comprising contacting a cell with a compound disclosed herein. In still other aspects, the present disclosure relates to methods of increasing lipolysis in a cell, comprising contacting the cell with a compound disclosed herein. In yet other aspects, the present disclosure relates to methods of modulating protein kinase A (PKA) activity in a cell, comprising contacting the cell with a compound disclosed herein.

It is hypothesized that compounds capable of regulating UCP1 levels could increase thermogenesis in animals. The compounds disclosed herein effectively induce endogenous UCP1 levels in mouse brown adipocytes and human white adipocytes. An exemplary compound from this family has been demonstrated to promote mitochondria-related gene expression, and activate PKA and lipolysis. Without wishing to be bound to any putative mechanism of action, experiments based on protein stabilization suggest that this compound acts by binding AKAP1 and AKAP13, thus modifying the PKA signaling pathway in adipocytes.

In further aspects, the present disclosure relates to methods of administering a β-adrenergic agonist to a patient, comprising conjointly administering the β-adrenergic agonist with a compound of Formula (I), (Ia), (Ib), or (Ic) disclosed herein or tautomer and/or salt thereof. Such conjoint administration may be achieved by way of the simultaneous, sequential or separate dosing of the individual components of the combination. In certain embodiments, the compound of Formula (I), (Ia), (Ib), or (Ic) disclosed herein, or tautomer and/or salt thereof, is administered before the β-adrenergic agonist. For example, the compound of Formula (I), (Ia), (Ib), or (Ic) disclosed herein, or tautomer and/or salt thereof, may be administered at least 1 minute before the β-adrenergic agonist, at least 5 minutes before the β-adrenergic agonist, at least 15 minutes before the β-adrenergic agonist, at least 30 minutes before the β-adrenergic agonist, or even at least 60 minutes before the β-adrenergic agonist.

In certain other embodiments, the compound of Formula (I), (Ia), (Ib), or (Ic) disclosed herein, or tautomer and/or salt thereof, is administered after the β-adrenergic agonist. For example, the compound of Formula (I), (Ia), (Ib), or (Ic) disclosed herein, or tautomer and/or salt thereof, may be administered at least 1 minute after the β-adrenergic agonist, at least 5 minutes after the β-adrenergic agonist, at least 15 minutes after the β-adrenergic agonist, at least 30 minutes after the β-adrenergic agonist, or even at least 60 minutes after the β-adrenergic agonist.

In other embodiments, the compound of Formula (I), (Ia), (Ib), or (Ic) disclosed herein, or tautomer and/or salt thereof, is administered simultaneously with the β-adrenergic agonist, such as in a single co-formulation with the β-adrenergic agonist.

In still further aspects, the present disclosure relates to methods of reducing β-adrenergic agonist-induced cardiac hypertrophy, comprising administering, to a patient receiving a β-adrenergic agonist, a compound disclosed herein.

Another aspect of the invention provides a kit for reducing the cardiac hypertrophy induced by β-adrenergic agonists. In certain such embodiments, the kit contains a hypertrophy-reducing compound, such as a compound of Formula (I), (Ia), (Ib), or (Ic), or tautomer and/or salt thereof, and instructions for administering the hypertrophy-reducing compound with a β-adrenergic agonist. The kit may optionally further include a β-adrenergic agonist. The hypertrophy-reducing compound and/or the β-adrenergic agonist (if present) may be provided as pharmaceutical preparations, whether for administration by the same route of administration (e.g., intravenous), or by differing routes of administration (e.g., the β-adrenergic agonist in an intravenous formulation and the hypertrophy-reducing compound as an oral formulation). The kit may include one or more hypertrophy-reducing compounds which may be formulated separately or together.

In some embodiments, the hypertrophy-reducing compound has cardioprotective properties. In some embodiments, the cardioprotective properties of the hypertrophy-reducing compound can be characterized by the reduction of β-adrenergic agonist-induced hypertrophy in cardiomyocytes.

BRIEF DESCRIPTION OF DRAWINGS

FIG. 1A is a schematic containing Ucp1 promoter-luciferase reporter constructs which are shown to scale below a diagram of evolutionarily conserved regions in the mouse Ucp1 promoter retrieved from the conservation track in the UCSC genome browser (genome.ucsc.edu). The location of the enhancer is indicated. FIG. 1B is a bar graph showing the luciferase activity (expressed as relative luminometer units, RLU) in brown adipocyte cell lines that were stably transfected with Ucp1 promoter-luciferase constructs shown in FIG. 1A. Cells were treated overnight with vehicle (Veh) or effectors indicated. n=2. FIG. 1C is a schematic summary of luciferase activity generated in brown adipocyte cell line stably expressing the 3 kb Ucp1 promoter-luciferase construct from FIG. 1A. Results are shown for 12,000 compounds (10 μM), with each dot representing the relative luciferase unit (RLU) for one compound. Horizontal dashed lines represent the arbitrary +/−55% change from values obtained with vehicle alone. Arrows indicate AST 7062601. n=2. FIG. 1D is a bar graph showing Ucp1 mRNA levels from immortalized brown adipocytes after overnight treatment with vehicle (Veh) or with AST 7062601 at the concentrations indicated. n=4. FIG. 1E is a bar graph showing Ucp1 mRNA levels after treatment with 10 μM AST 7062601 or other compounds with >81% identity. Treatment with vehicle (Veh) and with 10 nM CL316,243 are shown for comparison. n=3-4. All data presented as mean±SD. *, $p<0.05$, , $p<0.01$, *, $p<0.001$.

FIG. 2A is a series of bar graphs showing the relative expression of brown adipocyte, mitochondrial, and fatty acid oxidation markers after treatment with vehicle (Veh) or 10 μM AST070 or Z160 in primary brown adipocytes. n=4. FIG. 2B is a series of three bar graphs showing the cellular respiration in immortalized brown adipocytes treated with vehicle or 10 μM of AST070 or Z160. n=4. All data presented as mean±SD. *, $p<0.05$, , $p<0.01$, *, $p<0.001$.

FIG. 3A is a series of bar graphs showing the relative expression of brown adipocyte, mitochondrial, and fatty acid oxidation markers in human brown adipocytes, n=6-8. FIG. 3B is a series of bar graphs showing the cellular respiration in human brown adipocytes, n=20. FIG. 3C is a series of bar graphs showing the relative expression of brown adipocyte, mitochondrial, and fatty acid oxidation markers in human white adipocytes, n=4. FIG. 3D is a series of bar graphs showing the cellular respiration in human white adipocytes, n=12. For each data series all cells were treated with vehicle (Veh) or 10 μM Z160 for 4 days. All data presented as mean±SD. *, $p<0.05$, , $p<0.01$, *, $p<0.001$.

FIG. 4A is a series of bar graphs showing the relative expression of brown adipocyte, mitochondrial, and fatty acid oxidation markers. FIG. 4B is a series of bar graphs showing the cellular respiration data. For each data series all cells were treated with vehicle (Veh) or 10 μM Z160 at day 17 for 4 days. All data presented as mean±SD. *, $p<0.05$, ***, $p<0.001$.

FIG. 5A shows a volcano plot. NS, non-significant, FC, fold-change. FIG. 5B is series of bar graphs showing qPCR validation of microarray data for representative genes up-regulated by Z160. n=4. FIG. 5C is a is an image showing the electron transport chain protein complexes detected by Western blot in isolated mitochondria. Cells were treated overnight with vehicle (Veh), 10 μM Z160, or 10 μM AST070. Ponceau staining represents a loading control. Quantification as fold change is presented on the right. All data presented as mean±SD. *, $p<0.05$, , $p<0.01$, *, $p<0.001$.

FIG. 6A is a line graph showing body temperature ($p<0.05$ by two-way ANOVA). FIG. 6B is a schematic showing UCP1 protein in BAT. Beta-ACTIN (ACTB) is a loading control. FIG. 6C is a series of bar graphs showing mRNA levels in BAT. n=5. FIG. 6D is a bar graph showing aspartate aminotransferase activity measured in plasma. n=4-5. All data presented as mean±SD. n=5. *, p<0.05, **, p<0.01.

FIG. 7A is a schematic and bar graph. Ucp1 mRNA levels in mouse immortalized brown adipocytes treated with 10 μM Z160 (+) and either vehicle (Veh) or 20 μM tolazoline (Tola), 20 μM propranolol (Prop), 20 μM SR59230A (SR), 20 μM H-89, 20 μM SB202190 (SB). Cells were treated with the inhibitors 1 h prior to and during overnight Z160 treatment. The schematic on the left shows where the inhibitors act on the adrenergic signaling pathway leading to increase of Ucp1 expression. FIG. 7B is two bar graphs showing Cidea and Elovl3 mRNA levels after 10 μM Z160 treatment (+) and in presence of vehicle (Veh) or 20 μM H-89. H-89 was added 1 h prior and during the overnight Z160 treatment. FIG. 7C is a bar graph showing PKA activity in immortalized brown adipocytes treated overnight with vehicle (Veh), or 10 μM AST070 or Z160. FIG. 7D is a bar graph showing PKA activity in immortalized brown adipocyte lysates treated 30 min with Z160 concentrations indicated. FIG. 7E is a bar graph showing the relative (Rel.) PKA activity in mouse tissue lysates treated 30 min with 25 μM Z160. FIG. 7F is a bar graph showing the PKA activity in immortalized brown adipocyte lysates treated with 50 μM Z160, in presence of vehicle (Veh) or 500 μM H-89. H-89 was added to the lysates 10 min prior the 30 min incubation with Z160. All data presented as mean±SD. n=4. *, p<0.05, , p<0.01, *, p<0.001.

FIG. 8A shows a western blot analysis of phosphorylated and total p38 MAPK protein. Immortalized brown adipocytes were treated overnight with vehicle (Veh), 10 μM Z160, or 10 nM CL316,243 (CL). FIG. 8B is a bar graph showing the lipolysis of endogenous lipid in immortalized brown adipocytes after 10 μM Z160 overnight treatment. n=8. FIG. 8C is a series of bar graphs showing the mRNA levels of lipolysis-related genes in immortalized brown adipocytes measured by qPCR after 10 μM Z160 overnight treatment. n=4. FIG. 8D is a series of bar graphs showing the mRNA levels of lipolysis-related genes in immortalized primary adipocytes measured by qPCR after 10 μM Z160 overnight treatment. n=4. All data presented as mean±SD. *, p<0.05, ***, p<0.001.

FIG. 9A is a western blot showing tissue distribution of PKA subunits and AKAPs in mouse tissues with indicated antibodies. GAPDH represents a loading control. Sk, skeletal; Gon, gonadal; Ing, inguinal. FIG. 9B is the representative Western blot of a CETSA assay in immortalized brown adipocytes treated with vehicle (Veh) or 10 μM Z160 overnight. Temperature (° C.) is indicated across the top. FIG. 9C is the representative western blot of a DARTS assay in BAT extracts treated with different Z160 concentrations for 1 h. Pronase dilution is indicated across the top. FIG. 9D is the western blot of mitochondria-associated proteins isolated from immortalized brown adipocytes treated with 10 μM Z160 for the indicated time. FIG. 9E is the western blot showing co-immunoprecipitation of PKA C-α and PKA RII-β with AKAP1. Immortalized brown adipocytes were treated with vehicle (Veh), 10 μM AST070, or 10 μM Z160 for 7 h.

FIG. 10A shows the western blot analysis of cell lysates of the AKAP1wt and AKAP1mut cell lines probed with the AKAP1 antibody. GAPDH is a loading control. FIG. 10B is a series of bar graphs showing the relative expression of brown adipocyte, mitochondrial, and fatty acid oxidation markers after treatment with vehicle (Veh) or 10 μM Z160. n=6; mean±SD. *, p<0.05, , p<0.01, *, p<0.001.

FIG. 12A shows 8 representative plates of small molecules run in duplicate (screen 1 and 2). FIG. 12B is a bar graph representing the Ucp1 mRNA levels from brown adipocytes treated with vehicle (Veh) or 10 μM AST070 for times indicated. Mean±SD. ***, p<0.001 vs. vehicle (Veh).

FIG. 14A is a series of bar graphs showing the relative expression of brown adipocyte, mitochondrial, and fatty acid oxidation markers after treatment with vehicle (Veh) or 10 μM AST070 or Z160 in immortalized brown adipocytes. FIG. 14B is a series of bar graphs showing the relative expression of brown adipocyte, mitochondrial, and fatty acid oxidation markers after treatment with vehicle (Veh) or 10 μM AST070 or Z160 or in immortalized cells treated concomitantly with 10 nM CL316,243 overnight. All data presented as mean±SD. *, p<0.05, , p<0.01, *, p<0.001.

FIG. 15A is the representative western blot of a DARTS assay in immortalized brown adipocyte cell extracts treated with vehicle (−) or 20 μM Z160 (+) for 1 h. Pronase dilution is indicated across the top. FIG. 15B is the representative Western blot of a DARTS assay in immortalized brown adipocyte cell extracts treated with vehicle (Veh), 20 μM Z160, 20 μM AST070, or 20 nM CL316,243 for 1 h. Pronase dilution is indicated across the top.

FIG. 16A shows the western blot analysis for the phosphorylation of PKA substrates. Brown adipocytes were treated overnight with vehicle (Veh), 10 μM Z160, or 10 μM AST070. FIG. 16B is a series of bar graphs showing the mRNA levels in primary brown adipocytes after overnight treatment with vehicle (Veh) or 10 μM Z160. Mean±SD. *p<0.05, ***p<0.001.

FIG. 17A shows the representative western blot of a DARTS assay in H9c2 cell extracts treated with vehicle or 20 μM Z160 for 1 h. Pronase dilution is indicated across the top. The result shows a change of AKAP13 conformation in presence of Z160. FIG. 17B is a series of bar graphs showing the mRNA levels in primary cardiomyocytes after 2 days of treatment with vehicle (Veh) or 10 μM Z160 with or without the addition of 60 μM isoproterenol (ISO) or 50 μM phenylephrine (PE). ISO and PE increase Nppa and Nppb mRNA while decreasing Pln mRNA, three hypertrophic markers. Z160 reverses the effect of ISO and PE. Mean±SD. *, $p<0.05$ vs Veh. FIG. 17C shows mitochondrial reserve capacity in primary cardiomyocytes after 48h treatment with vehicle or 100 μM ISO, followed by 1 day treatment with vehicle or 10 μM Z160. Z160 prevented the ISO-induced reduction in reserve capacity. Mean±SD. *, $p<0.05$, **, $p<0.01$ vs Veh.

DETAILED DESCRIPTION

Definitions

Figure 1A:
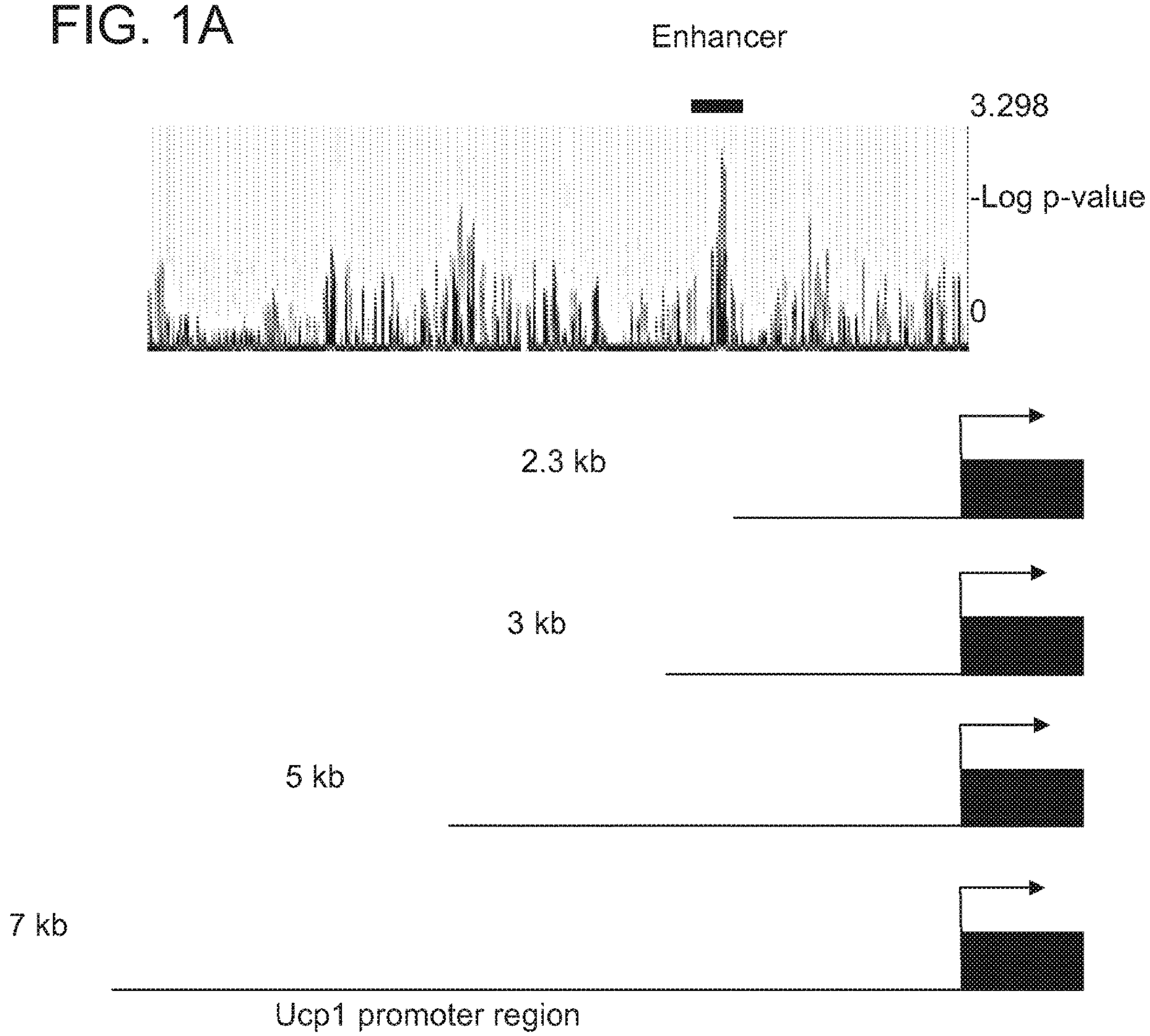
FIGS. 1A-1E depict the identification of small molecules that induce Ucp1 expression in mouse brown adipocytes.

"Patients receiving a β-adrenergic agonist", as the term is used herein, include patients who have been administered at least one dose of a β-adrenergic agonist within the prior week, patients who are prescribed to receive at least one dose of a β-adrenergic agonist within a week after receiving a hypertrophy-reducing compound, and patients who are otherwise being conjointly treated with a β-adrenergic agonist and a hypertrophy-reducing compound.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), $—CF_3$, —CN and the like. Exemplary substituted alkyls are described below. Cycloalkyls can be further substituted with alkyls, alkenyls, alkoxys, alkylthios, aminoalkyls, carbonyl-substituted alkyls, $—CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

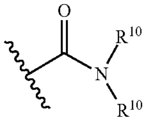

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

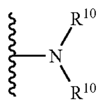

or

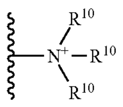

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

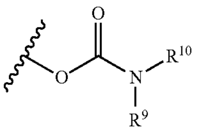

or

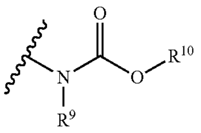

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group $—OCO_2—R^{10}$, wherein $R^{10}$ represents a hydrocarbyl group.

The term "carboxy", as used herein, refers to a group represented by the formula $—CO_2H$.

The term "ester", as used herein, refers to a group $—C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group $-OSO_3H$, or a pharmaceutically acceptable salt thereof.

The term "sulfonamide" is art-recognized and refers to the group represented by the general formulae

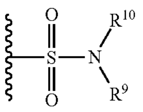
or
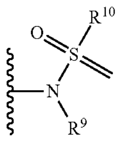

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group $-S(O)-R^{10}$, wherein $R^{10}$ represents a hydrocarbyl.

The term "sulfonate" is art-recognized and refers to the group $SO_3H$, or a pharmaceutically acceptable salt thereof.

The term "sulfone" is art-recognized and refers to the group $-S(O)_2-R^{10}$, wherein $R^{10}$ represents a hydrocarbyl.

The term "thioalkyl", as used herein, refers to an alkyl group substituted with a thiol group.

The term "thioester", as used herein, refers to a group $-C(O)SR^{10}$ or $-SC(O)R^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

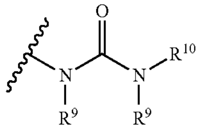

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry,* 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, the phrase "conjoint administration" refers to any form of administration of two or more different therapeutic compounds such that the second compound is administered
while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof). As used herein, treating a disease, disorder, or condition includes treating complication(s) of the disease, disorder, or condition, such as by treating the underlying pathophysiology specific to the complication(s) of the disease, disorder, or condition.

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or organic esters.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules). In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water. These compositions may also optionally contain opacifying agents and may be of a composition that they release the active ingredient(s) only, or preferentially, in a certain portion of the gastrointestinal tract, optionally, in a delayed manner Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Alternatively or additionally, compositions can be formulated for delivery via a catheter, stent, wire, or other intraluminal device. Delivery via such devices may be especially useful for delivery to the gastrointestinal tract.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In certain embodiments, the active compound will be administered once daily.

The patient receiving this treatment may be any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Methods

In certain aspects, disclosed herein is a method of treating or preventing a condition, comprising administering to a subject in need thereof an effective amount of a compound of formula (I):

(I)

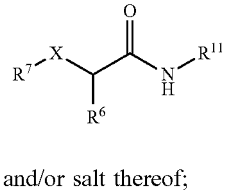

or a tautomer and/or salt thereof;

wherein:

X is S or $CH_2$;

$R^{11}$ is aryl;

$R^6$ is H;

$R^7$ is a quinazolin-4-on-2-yl group, such as

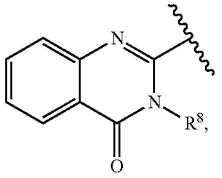

wherein the phenyl ring of the quinazolin-4-on-2-yl group may be substituted or unsubstituted; and $R^8$ is H, $C_{1-5}$ alkyl, $C_{1-5}$ alkenyl, or amino;

or $R^6$ and $R^7$ combine to form an optionally substituted piperidinyl or thiazinanyl ring, including the atoms to which $R^6$ and $R^7$ are attached; and wherein the condition is selected from obesity and associated complex metabolic, endocrine, and hemodynamic changes, dyslipidemias, cardiovascular disease, and type 2 diabetes.

In some aspects, disclosed herein is a method of enhancing mitochondrial respiration, comprising contacting a cell with a compound of formula (I):

(I)

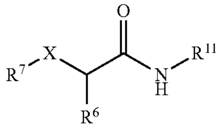

or a tautomer and/or salt thereof;

wherein:

X is S or $CH_2$;

$R^{11}$ is aryl;

$R^6$ is H;

$R^7$ is a quinazolin-4-on-2-yl group, such as

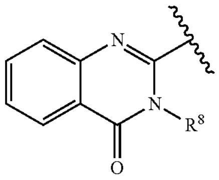

, wherein the phenyl ring of the quinazolin-4-on-2-yl group may be substituted or unsubstituted; and $R^8$ is H, $C_{1-5}$ alkyl, $C_{1-5}$ alkenyl, or amino;

or $R^6$ and $R^7$ combine to form an optionally substituted piperidinyl or thiazinanyl ring, including the atoms to which $R^6$ and $R^7$ are attached.

In some aspects, disclosed herein is a method of increasing lipolysis in a cell, comprising contacting the cell with a compound of formula (I):

(I)

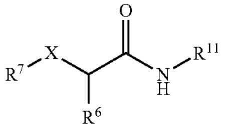

or a tautomer and/or salt thereof;

wherein:

X is S or $CH_2$;

$R^{11}$ is aryl;

$R^6$ is H;

$R^7$ is a quinazolin-4-on-2-yl group, such as

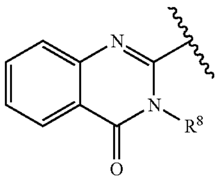

, wherein the phenyl ring of the quinazolin-4-on-2-yl group may be substituted or unsubstituted; and $R^8$ is H, $C_{1-5}$ alkyl, $C_{1-5}$ alkenyl, or amino;

or $R^6$ and $R^7$ combine to form an optionally substituted piperidinyl or thiazinanyl ring, including the atoms to which $R^6$ and $R^7$ are attached In some aspects, the present disclosure relates to methods of inducing Ucp1 transcription or modulating PKA activity in a cell, comprising contacting the cell with a compound of formula (I):

(I)

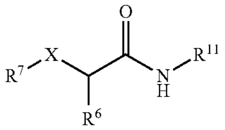

or a tautomer and/or salt thereof;

wherein:

X is S or $CH_2$;

$R^{11}$ is aryl;

$R^6$ is H;

$R^7$ is a quinazolin-4-on-2-yl group, such as

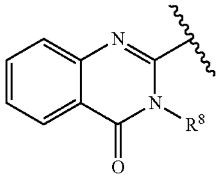

, wherein the phenyl ring of the quinazolin-4-on-2-yl group may be substituted or unsubstituted; and $R^8$ is H, $C_{1-5}$ alkyl, $C_{1-5}$ alkenyl, or amino;

or $R^6$ and $R^7$ combine to form an optionally substituted piperidinyl or thiazinanyl ring, including the atoms to which $R^6$ and $R^7$ are attached.

In some aspects, disclosed herein is a method of protecting a cell against hypertrophy, comprising contacting the cell with a compound of formula (I):

(I)

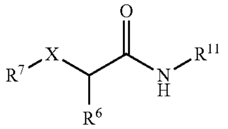

or a tautomer and/or salt thereof;

wherein:

X is S or $CH_2$;

$R^{11}$ is aryl;

$R^6$ is H;

$R^7$ is a quinazolin-4-on-2-yl group, such as

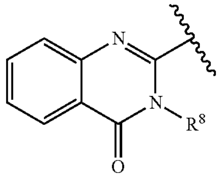

, wherein the phenyl ring of the quinazolin-4-on-2-yl group may be substituted or unsubstituted; and $R^8$ is H, $C_{1-5}$ alkyl, $C_{1-5}$ alkenyl, or amino;

or $R^6$ and $R^7$ combine to form an optionally substituted piperidinyl or thiazinanyl ring, including the atoms to which $R^6$ and $R^7$ are attached.

In certain embodiments, $R^{11}$ is a phenyl ring, e.g., substituted with one or more substituents selected from alkyl, alkoxy, aryloxy, aralkoxy, halo, and cyano. In other embodiments, $R^{11}$ is a phenyl ring fused with a dioxane or dioxolane ring, and may optionally be further substituted with one or more substituents, e.g., substituents selected from alkyl, alkoxy, aryloxy, aralkoxy, halo, and cyano.

In certain embodiments, the compound of formula (I) is a compound of formula (Ia):

(Ia)

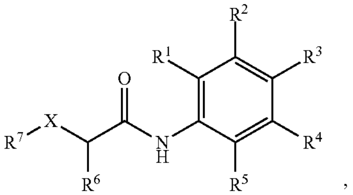

, or a tautomer or salt thereof;

wherein:

$R^1$ is H, $C_{1-3}$ alkyl, or $C_{1-3}$ alkoxy;

$R^2$ is H or $C_{1-3}$ alkoxy;

$R^3$ is H, $C_{1-3}$ alkoxy, phenoxy, or benzyloxy;

$R^4$ is H, hydroxyl, $C_{1-3}$ alkoxy, or $C_{1-3}$ haloalkoxy;

or $R^3$ and $R^4$ combine to form a dioxane or dioxolane ring, including the atoms to which $R^3$ and $R^4$ are attached; and $R^5$ is H or $C_{1-3}$ alkyl.

In some embodiments, $R^1$ is H, $CH_3$, methoxy, or ethoxy; $R^2$ is H or methoxy; $R^3$ is H, methoxy, ethoxy, phenoxy, or benzyloxy; $R^4$ is H, methoxy, ethoxy, tetrafluoroethoxy, or hydroxyl; or $R^3$ and $R^4$ combine to form a dioxane or dioxolane ring, including the atoms to which $R^3$ and $R^4$ are attached; and $R^5$ is H or methyl.

In some embodiments, $R^2$ is H; $R^3$ is H, methoxy, ethoxy, or phenoxy; and $R^4$ is H, methoxy, tetrafluoroethoxy, or hydroxyl; or $R^3$ and $R^4$ combine to form a dioxane or dioxolane ring including the atoms to which $R^3$ and $R^4$ are attached.

In some embodiments, $R^6$ and $R^7$ combine to form a piperidinyl ring.

In some embodiments, $R^7$ is

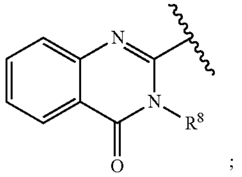

;

and $R^8$ is H, $CH_3$, ethyl, methoxypropyl, or amino.

In some embodiments, the compound of Formula I is selected from:

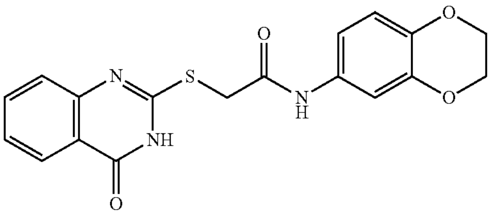

,

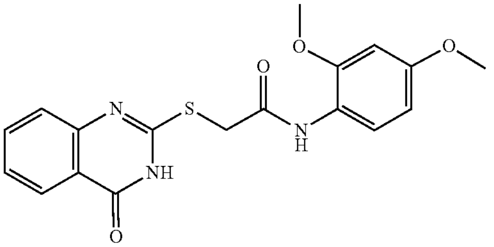

,

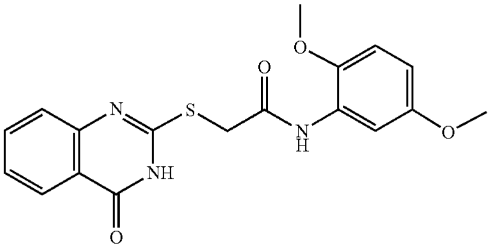

,

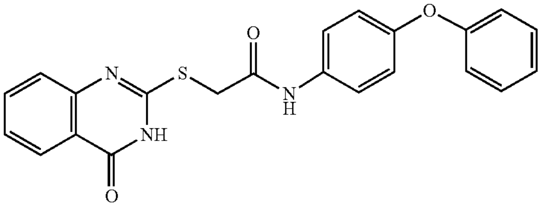

,

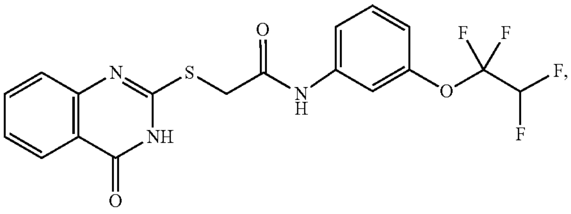

,

-continued
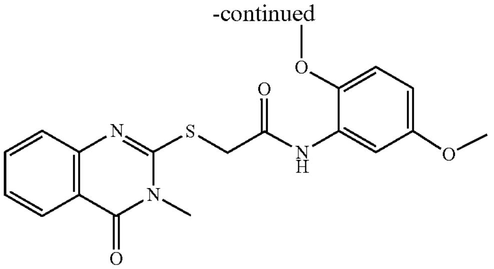
,
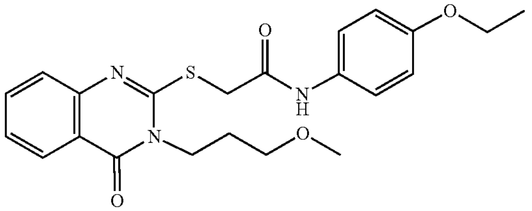
,
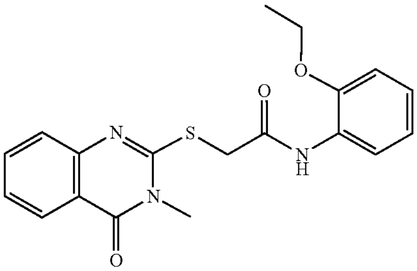
,
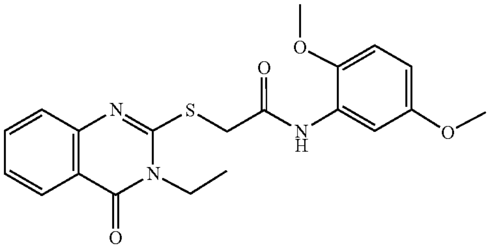
,
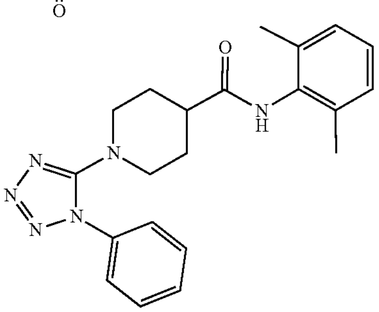
,
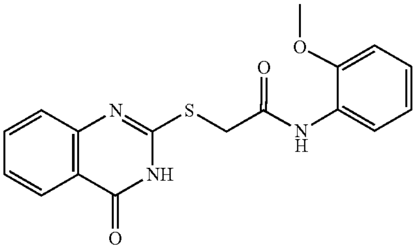
,
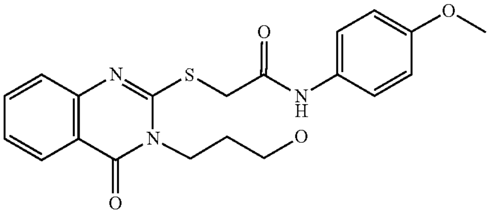
, and
-continued
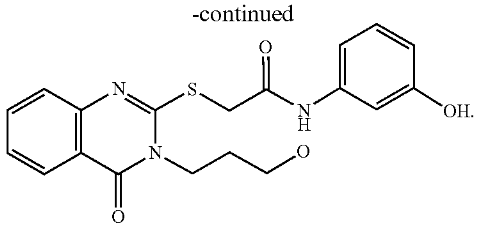
In certain preferred embodiments, the compound of formula (Ia) is
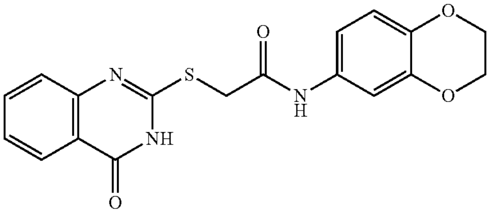
or
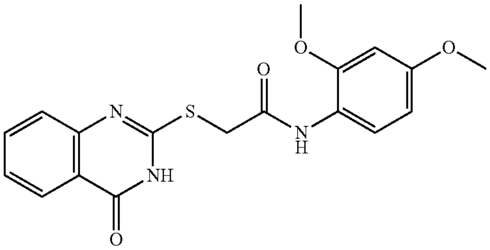
.
In even more preferred embodiments, the compound of formula (Ia) is
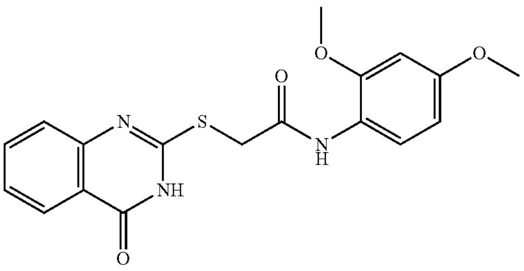 [SMILES: COc1ccc(NC(=O)CSc2nc3ccccc3c(=O)[nH]2)c(OC)c1]
In some embodiments, the compound of formula (Ia) is a compound of formula (Ib):
(Ib)
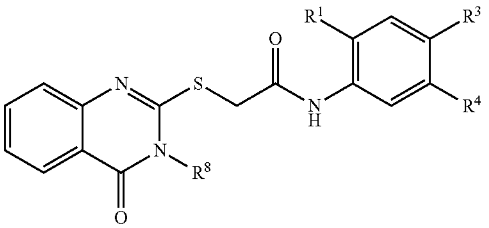
or a tautomer or salt thereof; wherein:
$R^1$ is H or methoxy;
$R^3$ is H or methoxy, and $R^4$ is H or methoxy, or $R^3$ and $R^4$ combine to form a dioxane or dioxolane ring including the atoms to which $R^3$ and $R^4$ are attached; and $R^8$ is H or $C_{1-3}$ alkyl.

In some embodiments, the compound of formula (Ib) is selected from:

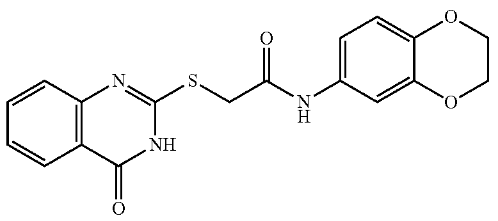 [SMILES: O=C(CSc1nc2ccccc2c(=O)[nH]1)Nc1ccc2c(c1)OCCO2]
,
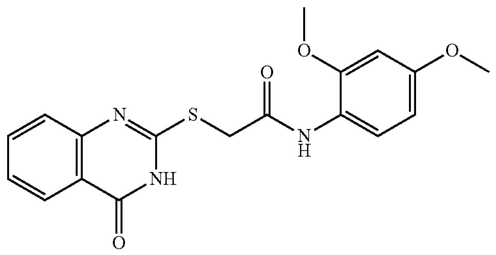 [SMILES: COc1ccc(NC(=O)CSc2nc3ccccc3c(=O)[nH]2)c(OC)c1]
,
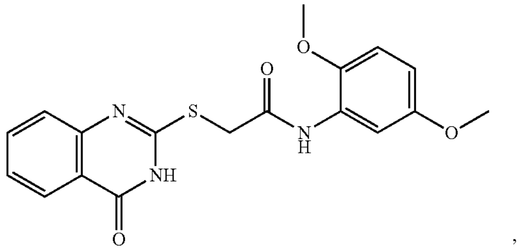
, and
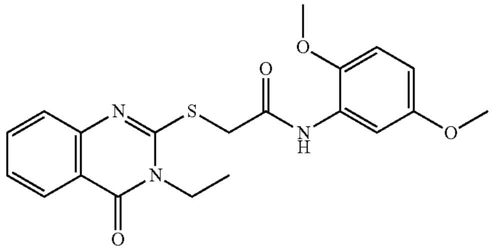
.

In certain embodiments, n the compound of formula (Ia) is a compound of formula (Ic):

(Ic)
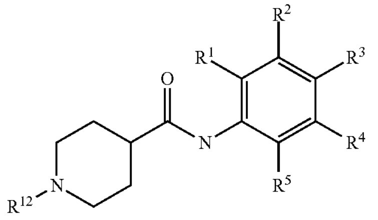

wherein $R^{12}$ is a heteroaryl, such as a tetrazole, e.g., substituted with a substituted or unsubstituted phenyl group.

In certain preferred embodiments, the compound of formula (Ic) is

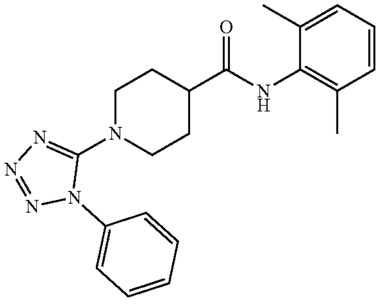
.

In some embodiments, the compound is a compound selected from the compounds identified in Table 2.

In certain embodiments, the cell is an adipocyte or a cardiomyocyte. In certain embodiments, the cardiomyocyte has been previously contacted with a β-adrenergic agonist.

In further aspects, the present disclosure relates to methods of administering a β-adrenergic agonist to a patient, comprising conjointly administering the β-adrenergic agonist with a compound of Formula (I), (Ia), (Ib), or (Ic) disclosed herein or tautomer and/or salt thereof. Such conjoint administration may be achieved by way of the simultaneous, sequential or separate dosing of the individual components of the combination. In certain embodiments, the compound of Formula (I), (Ia), (Ib), or (Ic) disclosed herein, or tautomer and/or salt thereof, is administered before the β-adrenergic agonist. For example, the compound of Formula (I), (Ia), (Ib), or (Ic) disclosed herein, or tautomer and/or salt thereof, may be administered at least 1 minute before the β-adrenergic agonist, at least 5 minutes before the β-adrenergic agonist, at least 15 minutes before the β-adrenergic agonist, at least 30 minutes before the β-adrenergic agonist, or even at least 60 minutes before the β-adrenergic agonist.

In certain other embodiments, the compound of Formula (I), (Ia), (Ib), or (Ic) disclosed herein, or tautomer and/or salt thereof, is administered after the β-adrenergic agonist. For example, the compound of Formula (I), (Ia), (Ib), or (Ic) disclosed herein, or tautomer and/or salt thereof, may be administered at least 1 minute after the β-adrenergic agonist, at least 5 minutes after the β-adrenergic agonist, at least 15 minutes after the β-adrenergic agonist, at least 30 minutes after the β-adrenergic agonist, or even at least 60 minutes after the β-adrenergic agonist.

In other embodiments, the compound of Formula (I), (Ia), (Ib), or (Ic) disclosed herein, or tautomer and/or salt thereof, is administered simultaneously with the β-adrenergic agonist, such as in a single co-formulation with the β-adrenergic agonist.

In still further aspects, the present disclosure relates to methods of reducing β-adrenergic agonist-induced cardiac hypertrophy, comprising administering, to a patient receiving a β-adrenergic agonist, a compound of Formula (I), (Ia), (Ib), or (Ic).

In certain embodiments, the β-adrenergic agonist is selected from isoproterenol, phenylephrine, denopamine, dobutamine, dopexamine, epinephrine, prenalterol, xamoterol, Arformoterol, Buphenine, Clenbuterol, Dopexamine, Epinephrine, Fenoterol, Formoterol, Isoetarine, Isoprenaline, Levosalbutamol, levalbuterol, Orciprenaline, metaproterenol, Pirbuterol, Procaterol, Ritodrine, Salbutamol, albuterol, Salmeterol, Terbutaline, Arbutamine, Befunolol, Bromoacetylalprenololmenthane, Broxaterol, Cimaterol, Cirazoline, Etilefrine, Hexoprenaline, Higenamine, Isoxsuprine, Mabuterol, Methoxyphenamine, Oxyfedrine, Ractopamine, Reproterol, Rimiterol, Tretoquinol, Tulobuterol, Zilpaterol, Zinterol, CL316,243, Rafabegron, Mirabegron, Solabegron, Amibegron, Talibegron, and L-796568. In certain preferred embodiments, the β-adrenergic agonist is selected from isoproterenol and phenylephrine.

Another aspect of the invention provides a kit for reducing the cardiac hypertrophy induced by β-adrenergic agonists. In certain such embodiments, the kit contains a hypertrophy-reducing compound, such as a compound of Formula (I), (Ia), (Ib), or (Ic), or tautomer and/or salt thereof, and instructions for administering the hypertrophy-reducing compound with a β-adrenergic agonist. The kit may optionally further include a β-adrenergic agonist. The hypertrophy-reducing compound and/or the β-adrenergic agonist (if present) may be provided as pharmaceutical preparations, whether for administration by the same route of administration (e.g., intravenous), or by differing routes of administration (e.g., the β-adrenergic agonist in an intravenous formulation and the hypertrophy-reducing compound as an oral formulation). The kit may include one or more hypertrophy-reducing compounds which may be formulated separately or together.

In some embodiments, the hypertrophy-reducing compound has cardioprotective properties. In some embodiments, the cardioprotective properties of the hypertrophy-reducing compound can be characterized by the reduction of β-adrenergic agonist-induced hypertrophy in cardiomyocytes.

EXEMPLIFICATION

The invention now being generally described, it will be more readily understood by reference to the following examples, which are included merely for purposes of illustration of certain aspects and embodiments of the present invention, and are not intended to limit the invention.

Example 1. Materials and Methods

Cell Culture

Primary brown adipocytes were isolated according to known methods. An established mouse brown adipocyte cell line was obtained from Dr. Bruce Spiegelman (Dana-Farber Cancer Institute, Boston, USA). To differentiate primary and immortalized brown adipocytes, cells were grown until confluency in DMEM containing 10% FBS, 25 mM glucose 1 mM pyruvate, 2 mM glutamine, 20 nM insulin, 1 nM T3, and antibiotics. Once confluent (day 0), differentiation was induced by supplementing the medium with 0.5 mM IBMX, 0.5 μM dexamethasone, and 0.125 mM indomethacin, for 2 days. Differentiation was continued in the original medium (without IBMX, dexamethasone and indomethacin) for 7-10 days.

Human immortalized brown and white preadipocytes were obtained from Dr. Yu-Hua Tseng (Joslin Diabetes Center, Harvard Medical School, USA). The generation of the two cell lines from human neck adipose tissue biopsies and immortalization was performed as previously described but from a different donor. Cells were cultured in high glucose DMEM supplemented with 10% FBS and antibiotics. Two days after reaching confluence, cells were treated with 30 μM biotin, 500 nM insulin, 17 μM pantothenate, 100 nM dexamethasone, 2 nM 3,3',5-Triiodo-L-thyronine, 500 μM IBMX, 30 μM indomethacin and 1 μM rosiglitazone, for 12 days. Afterwards, cells were treated with 30 μM biotin, 500 nM insulin, 17 μM pantothenate and 2 nM 3,3',5-Triiodo-L-thyronine (Maintenance media) for 2 days with end-point assays performed on day 18, and for 5 days with end-point assays performed on day 21, for the brown and white adipocytes cells, respectively.

Rat H9c2 cells were grown in DMEM supplemented with 10% FBS, 25 mM glucose, 1 mM pyruvate, and 2 mM glutamine Neonatal rat ventricular myocytes (NRVM) were isolated and cultured as previously described. Briefly, 2-4 day old rats were sacrificed and myocytes and fibroblasts were isolated and separated using a Percoll density gradient. Following isolation, NRVMs were plated on gelatin-coated plates in DMEM containing 10% FBS, 25 mM glucose, 1 mM pyruvate, and 2 mM glutamine The next day, FBS was replaced by 1× insulin-transferrin-selenium supplement and the cells were treated with vehicle or 10 μM Z160 for 2 days, with or without 60 μM isoproterenol or 50 μM phenylephrine.

Generation of Brown Adipocyte UCP1-Reporter Cell Lines

Different lengths of mouse Ucp1 promoter were cloned into pGL3-basic vector (Promega) by PCR, using the NheI and XhoI sites. PCR amplification was performed on Ucp1 promoter fragments of 2.3 kb (cttgatgtgtggagctgagtagc (SEQ ID NO: 1)), 3 kb (gtgccgtcactaacagtactg (SEQ ID NO: 2), 5 kb (ctgcagactcctgacacagct (SEQ ID NO: 3)), and 7 kb (ggaaagtggttcagtttgattagaagg (SEO ID NO: 4)) plus 94 bases downstream of the transcription start site (reverse primer: ctaggtagtgccagtgcagag (SEQ ID NO: 5)). To perform chemical library screening in mature brown adipocytes, stable cell lines in the immortalized mouse brown adipocytes were created. For this purpose, a neomycin cassette from pcDNA3.1/V5-His vector (Invitrogen) was introduced into the SalI site of pGL3-basic plasmid. All constructs were verified by sequencing. Stable cell lines were selected with 500 μg/ml G418.

Luciferase Assay for Pilot Studies Prior to Drug Screen

Stable brown adipocyte cell lines carrying Ucp1 promoter-luciferase constructs were seeded in 96-well plates and differentiated for 7-10 days. Cells were treated with either 10 nM CL316,243, 10 μM forskolin, 1 μM rosiglitazone, or 1 μM cis- and trans-retinoic acid, overnight. Luciferase activity was assayed using LAR II or Bright-Glo luciferase assay system (Promega). For the LAR II assays, passive lysis was performed on the cells. Luminescence was measured with a GloMax Luminometer. The Bright-Glo luciferase assay system was selected for the drug screen.

Small Molecule Library Screen

TScreening was conducted at the UCLA Molecular Screening Shared Resource using automated instruments Immortalized brown adipocytes were differentiated in T225 flasks and plated in Matrix 384-well plates (26,000 cells per well) with white flat bottom (ThermoScientific) using trypsin and collagenase type II (Sigma C6885). The small molecule libraries screened were a BioMol library (204 compounds), an FDA-approved drug library (1120 compounds), a Microsource spectrum collection (2000 compounds), and a druggable compound set (8000 compounds). Molecules were delivered at 10 μM final concentration in DMSO. The screen was performed in duplicate on different days. After 18 h, luciferase activity was measured with Bright-Glo luciferase assay system and an LJL instrument. Data were normalized to the basal response (100% activity) in the presence of DMSO. Following the primary screen, 92 molecules were selected for validation and used to treat brown adipocyte cells plated in a 96-well plate overnight. RNA was extracted with an SV 96 Total RNA Isolation System (Promega). Compounds used for follow-up studies were identified using search tools available from Molport (molport.com), and ordered from the same company.

Cellular Bioenergetics

Cellular respiration was measured using a Seahorse XF24 or XF96 analyzer (Agilent) following known protocols Immortalized brown adipocytes were differentiated in 6-well plates and replated in the Seahorse XF24 plates at a density of 50,000 cells per well using trypsin and collagenase type II. Cells were treated with vehicle (DMSO) or compounds for 18-24 h. Oxygen consumption rates were obtained before and after the sequential injection of 0.75 μM oligomycin, 0.5 μM FCCP, and 0.75 μM rotenone/myxothiazol. Results were normalized to total protein. For human white adipocytes, cells were cultured as described above and differentiated in XF96 microplates. DMSO or Z160 (10 μM) was added at day 17 and for 4 days. Oxygen consumption rates were measured before and after the sequential injection of 1 μM oligomycin, 1 μM FCCP, and 0.5 μM rotenone/antimycin A. For these cells, results were normalized to cell count determined by nuclei fluorescent staining with Hoescht staining imaged on Cytation 5 Imaging Reader and analysis with Gen5 software (BioTek). For both mouse and human cell lines, mitochondrial respiration was calculated by subtracting the non-mitochondrial respiration present after the last injection. Uncoupled respiration corresponds to the respiration difference between oligomycin and the last injections. Maximal respiration was determined after FCCP injection.

Gene Expression Analysis

RNA levels were measured by qPCR according to known methods. Briefly, RNA was extracted with TRIzol (Invitrogen) and reverse transcribed with iScript (Bio-Rad). Real-time PCR analysis was performed with a CFX Connect (Bio-Rad).

Mouse RNA levels were measured by qPCR according to known methods. Data were normalized to B2m and Tbp reference genes. Primers are listed in Table 1. Human RNA was extracted using an RNA Mini Plus kit (Zymo) and gene expression determined by Taqman assay. The 1-step qPCR was run on a QuantStudio 12K Flex Real Time PCR System (ThermoFisher) using the following protocol: 50° C. for 5 minutes, 95° C. for 20 seconds, 40 cycles of 95° C. for 15 seconds and 60° C. for 60 seconds. Data were normalized to PPIA and PSMB2 reference genes. Taqman probes (ThermoFisher Scientific) are listed in Table 1. For global gene expression analysis, RNA isolated from brown adipocytes treated with compounds as indicated (four biological replicates) was hybridized to Illumina mouse Ref 8 V2.0 bead chips at the University of California, Los Angeles Neuroscience Genomics Core as previously described. Data were processed with GenomeStudio V2011.1 using the quantile normalization, background subtraction, and a present call of $P<0.05$.

TABLE 1

Primers and probes used in real time PCR.

| Species | Gene | Sequences |
|---|---|---|
| Mouse | Ucp1 | GGGCCCTTGTAAACAACAAA (SEQ ID NO: 6),<br>GTCGGTCCTTCCTTGGTGTA (SEQ ID NO: 7) |
| Mouse | Zic1 | AACCTCAAGATCCACAAAAGGA (SEQ ID NO: 8),<br>CCTCGAACTCGCACTTGAA (SEQ ID NO: 9) |
| Mouse | Hoxa5 | CAAGCTGCACATTAGTCACG (SEQ ID NO: 10),<br>GGTAGCGGTTGAAGTGGAAT (SEQ ID NO: 11) |
| Mouse | Ppargc1 | CTCACAGAGACACTGGACAGT (SEQ ID NO: 12),<br>TGTAGCTGAGCTGAGTGTTGG (SEQ ID NO: 13) |
| Mouse | Cidea | ATCACAACTGGCCTGGTTACG (SEQ ID NO: 14),<br>TACTACCCGGTGTCCATTTCT (SEQ ID NO: 15) |
| Mouse | Elovl3 | GATGGTTCTGGGCACCATCTT (SEQ ID NO: 16),<br>CGTTGTTGTGTGGCATCCTT (SEQ ID NO: 17) |
| Mouse | Acox1 | CAGGAAGAGCAAGGAAGTGG (SEQ ID NO: 18),<br>CCTTTCTGGCTGATCCCATA (SEQ ID NO: 19) |
| Mouse | Cpt1b | GTCGCTTCTTCAAGGTCTGG (SEQ ID NO: 20),<br>AAGAAAGCAGCACGTTCGAT (SEQ ID NO: 21) |
| Mouse | Prdm16 | CGCTGTGATGAGTGTGATGAG (SEQ ID NO: 22),<br>CGTGTGGACGATCATGTGTTG (SEQ ID NO: 23) |
| Mouse | Ndufb4 | CTTGCATAGGTCCAGCGAAT (SEQ ID NO: 24),<br>GGCTTAAACGGGAGTATCTGC (SEQ ID NO: 25) |
| Mouse | Ndufab1 | ACTGTACTGGCGGCACAAAT (SEQ ID NO: 26),<br>GAGGGAATCCGGAGGAGA (SEQ ID NO: 27) |
| Mouse | Sdhb | TGACACATAAGCGGGTCTGA (SEQ ID NO: 28),<br>CATGGCGGTTCTCTTAAAGC (SEQ ID NO: 29) |
| Mouse | Cycs | CCAGTCTTATGCTTGCCTCC (SEQ ID NO: 30),<br>GGACGTCTGTCTTCGAGTCC (SEQ ID NO: 31) |
| Mouse | Cox6a2 | GAAGAGCCAGCACAAAGGTC (SEQ ID NO: 32),<br>GGCTCTGCCTCTAAAGGTCC (SEQ ID NO: 33) |

TABLE 1-continued

Primers and probes used in real time PCR.

| Species | Gene | Sequences |
|---|---|---|
| Mouse | Atp5a1 | CAACAAAGGATGACCCCAAA (SEQ ID NO: 34), AAGCTGCAAGGATGCTGTCT (SEQ ID NO: 35) |
| Mouse | Atgl | TCGTGTTTCAGACGGAGAGAA (SEQ ID NO: 36), CAGACATTGGCCTGGATGAG (SEQ ID NO: 37) |
| Mouse | Hsl | GGAACTAAGTGGACGCAAGC (SEQ ID NO: 38), CCAGGGCTGCCTCAGACAC (SEQ ID NO: 39) |
| Mouse | FGF21 | ACCTGGAGATCAGGGAGGAT (SEQ ID NO: 40) GTCCTCCAGCAGCAGTTCTC (SEQ ID NO: 41) |
| Mouse | B2m | CAGCATGGCTCGCTCGGTGAC (SEQ ID NO: 42), CGTAGCAGTTCAGTATGTTCG (SEQ ID NO: 43) |
| Mouse | Tbp | ACCCTTCACCAATGACTCCTATG (SEQ ID NO: 44), ATGATGACTGCAGCAAATCGC (SEQ ID NO: 45) |
| Human | UCP1 | Hs00222453_m1 (ThermoFisher Scientific) |
| Human | CIDEA | Hs00154455_m1 (ThermoFisher Scientific) |
| Human | ACADM | Hs00936576_m1 (ThermoFisher Scientific) |
| Human | CPT1B | Hs03046298_s1 (ThermoFisher Scientific) |
| Human | ELOVL3 | Hs00537016_m1 (ThermoFisher Scientific) |
| Human | PPIA | Hs99999904_m1 (ThermoFisher Scientific) |
| Human | PSMB2 | Hs01002946_m1 (ThermoFisher Scientific) |

Immunoblot Analysis.

Cells and tissues were lysed in 10 mM Tris pH 7.5, 10 mM NaCl, 1 mM EDTA and 0.5% Triton X-100, supplemented with complete mini EDTA-free protease (Roche Diagnostics) and phosphatase (Cocktail 2 and 3, Sigma) inhibitors, followed by 10 second sonication. For analysis of mitochondrial proteins, mitochondria were isolated from cells by dual centrifugation, as described. Protein lysates were separated by SDS-PAGE and transferred to a nitrocellulose membrane. Transfer was confirmed by Ponceau staining (P7170, Sigma). After blocking in 5% milk, 0.1% Tween-20 in Tris-buffered saline (TBS), primary antibody was incubated overnight at 4° C. in 5% bovine serum albumin and 0.1% Tween-20 in TBS. Primary antibodies against ACTB (GTX109639, GeneTex), AKAP1 (5203, Cell Signaling), AKAP6 (07-087, Millipore), Cytochrome c (136F3, Cell Signaling), electron transport chain protein complexes (Total OXPHOS rodent WB antibody cocktail ab110413, Abcam), GAPDH (GTX100118, Genetex), active p38 MAPK (V1211, Promega), total p38 MAPK (8690, Cell Signaling), PGC1α (AB3242, Millipore), phospho-(Ser/Thr) PKA substrate (9621, Cell Signaling), PKA C-α (4782, Cell Signaling), PKA RII-β (ab75993, Abcam), and UCP1 (662045, Calbiochem) were used at 1:2000. Peroxidase goat anti-rabbit (sc-2030, Santa Cruz Biotechnology, Inc) or rabbit anti-mouse (A9044, Sigma) secondary antibody was used at a 1:10,000 dilution for 1 h at room temperature in 5% milk and 0.1% Tween-20 in TBS Immunoreactive bands were revealed with ECL prime (Amersham) and visualized with a Bio-Rad Gel-doc imager. Quantification using representative bands from the Ponceau staining was performed with ImageJ.

Co-Immunoprecipitation

Immortalized brown adipocyte cells were differentiated for 10 days and treated with 10 μM AST070 or Z160 for 7 h. Cells were lysed in 150 mM NaCl, 50 mM Tris pH 7.5, 1% Nonidet P40, 0.5% Na-deoxycholate containing protease and phosphatase inhibitors. Cell lysates were incubated overnight at 4° C. with 2 μl of anti-AKAP1 antibody. Twenty microliter of Protein A/G PLUS agarose beads (Santa Cruz Biotechnologies) were added for 2 h at 4° C. After a initial wash (500 mM NaCl, 50 mM Tris pH 7.5, 0.1% Nonidet P40, 0.05% Na-deoxycholate) and a final wash (10 mM Tris pH 7.5, 0.1% Nonidet P40, 0.05% Na-deoxycholate), proteins were eluted from the beads with 1× loading buffer and 2% β-mercaptoethanol, boiled for 10 min and analyzed by Western blot. To avoid detecting the IgG heavy chain, TidyBlot Western Blot reagent:HRP (Bio-Rad) at 1:100 was used as secondary antibody to reveal the PKA subunits from the co-immunoprecipitation blot.

Assessment of PKA Activity

PKA kinase activity was measured with an ELISA that utilized a synthetic peptide as substrate for PKA and a polyclonal antibody that recognizes the phosphorylated form of the substrate (ab139435, Abcam). PKA activity was measured in lysates from cultured brown adipocytes, mouse BAT, or liver. Cells and tissues were lysed in 20 mM MOPS, 5 mM EGTA, 2 mM EDTA, and 0.1% Triton X-100 supplemented with protease and phosphatase inhibitor as described above. Protein concentration was determined by Bradford assay and 10 μg of cells, 0.25 μg of BAT extract, or 0.5 μg of liver extract were assessed for PKA activation according to the manufacturer's instruction, with minor changes. Briefly, vehicle or Z160 was incubated with brown adipocyte cells overnight or with protein lysates for 30 min, followed by one wash before the primary antibody, 60 min incubation with the primary antibody, 30 min incubation with the secondary antibody, and by 10 min washing. Absorbance was measured after the substrate was added for 20-60 min, depending the intensity of the signal.

Lipolysis Assay

Lipolysis was assessed in cultured cells using medium collected over 3 h with the Adipolysis assay kit (AB100, Millipore), according to the manufacturer's protocol.

Cellular Thermal Shift Assay (CETSA)

CETSA assays were performed according to known methods. Briefly, differentiated brown adipocytes (one 10 cm dish per treatment) were treated with vehicle or compounds, trypsinized, counted, and re-suspended in approximately 450 μl PBS containing protease inhibitors (volumes were adjusted to have the same number of cells in each treatment). For each sample, 18 μl was distributed into each of 7 PCR tubes. Samples were heated using a thermocycler with a temperature gradient (iCycler, Biorad) for 3 min, followed by 3 min at room temperature, and then snap-frozen in liquid $N_2$. After two freeze-thaw cycles, samples were centrifuged at 20,000 g for 15 min at 4° C., and the supernatants were transferred to another set of tubes. Proteins were analyzed by immunoblotting.

Drug Affinity Responsive Target Stability (DARTS)

ARTS assays were performed according to known methods. Briefly, BAT or cells within a 10 cm dish were lysed with 600 μl M-PER buffer containing protease and phosphatase inhibitors. Debris was pelleted by centrifugation at 18,000 g for 10 min at 4° C., and the lysates were harvested and supplemented with TNC buffer (50 mM Tris-HCl, 50 mM NaCl, 10 mM $CaCl_2$). The lysates were split into two tubes and treated with either vehicle or 20 μM Z160 for 1 h at room temperature. For experiment with BAT, 100 μg of lysate was incubated with different Z160 concentrations. Different concentrations of pronase (from 1:100 to 1:10,000 dilution from a 1.25 mg/ml pronase stock) were incubated with the samples for 30 min at room temperature and the reaction was stopped with SDS loading buffer followed immediately by heating at 70° C. for 10 min. Protein lysates were separated by SDS-PAGE and transferred to a nitrocellulose membrane. After blocking in 5% milk, 0.1% Tween-20 in Tris-buffered saline (TBS), primary antibody was incubated overnight at 4° C. in 5% bovine serum albumin and 0.1% Tween-20 in TBS. Primary antibodies against AKAP1 (5203, Cell Signaling), AKAP13 (39715, One World Lab), GAPDH (GTX100118, Genetex), OPA1 (39557, One World Lab), PKA C-α (4782, Cell Signaling), PKA RII-β (ab75993, Abcam), were used at 1:2000. A goat anti-rabbit secondary antibody (sc-2030, Santa Cruz Biotechnology, Inc) was used at a 1:10,000 dilution for 1 h at room temperature in 5% milk and 0.1% Tween-20 in TBS. Immunoreactive bands were revealed with ECL prime (Amersham) and visualized with a Bio-Rad Gel-doc imager.

CRISPR/Cas9 Akap1 Gene Editing

Two gRNAs were selected using sgRNA Designer from the Broad Institute (gRNA1: gagggggcaagtaacccgag (SEQ ID NO: 46) and gRNA2: actggctccacaaagctact (SEQ ID NO: 47)). Cloning was performed using pSpCas9 (BB)-2A-puro (PX459) V2.0 vector (Addgene plasmid #62988). Plasmid construction was confirmed by sequencing. A puromycin-sensitive brown adipocyte cell line was transfected with the two plasmids and selected with 3 μg/μl puromycin. Single-cell cloning was performed in a 96-well plate and clones selected by Western blot to detect AKAP1 protein knockdown, and confirmed by sequencing after PCR amplification (PCR primers: gcaagagtcttcaagccccg (SEQ ID NO: 48) and ggagaagaggtgagccatgg (SEQ ID NO: 49)).

Animal Experiments

All mouse studies were conducted in accordance with and approved by the Institutional Animal Research Committee of the University of California, Los Angeles. C57BL/6J male mice were obtained from the Jackson Laboratory. For the drug injection, Z160 (diluted in 100 μl DMSO) was injected subcutaneously, near BAT, at 1.5 mg/kg body weight and compared with vehicle alone. Plasma and tissues were obtained after 20 h. Body temperature was obtained with a rectal probe (BAT-12, Physitemp). Aspartate aminotransferase (AST) activity was determined from plasma according to the manufacturer's protocol (MAK055, Sigma).

Statistical Analyses

Statistical analyses were performed by unpaired 2-tailed Student's t test. A value of $p<0.05$ was considered significant.

Respirometry

NRVM were seeded in a Seahorse Bioscience XF96 plate and cultured for 48 h in 10% FBS. Next, cells were treated with 100 μM ISO for 48 h, followed by 24 h of 10 μM Z160. Oxygen consumption rate (OCR) was recorded in a Seahorse Bioscience XF96 analyzer before and after the sequential injection of 0.75 μM oligomycin, 0.75 μm FCCP and 0.75 μM rotenone/myxothiazol. Reserve capacity was calculated as the difference between basal respiration and FCCP response.

Example 2: Identification of Small Molecules that Induce Ucp1 Expression

Figure 1B:
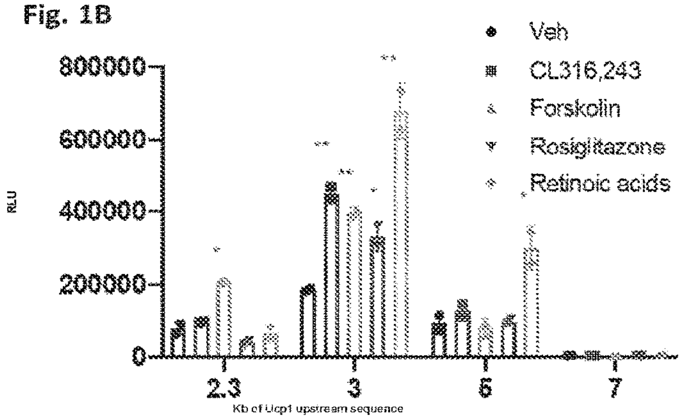
Figure 12A:
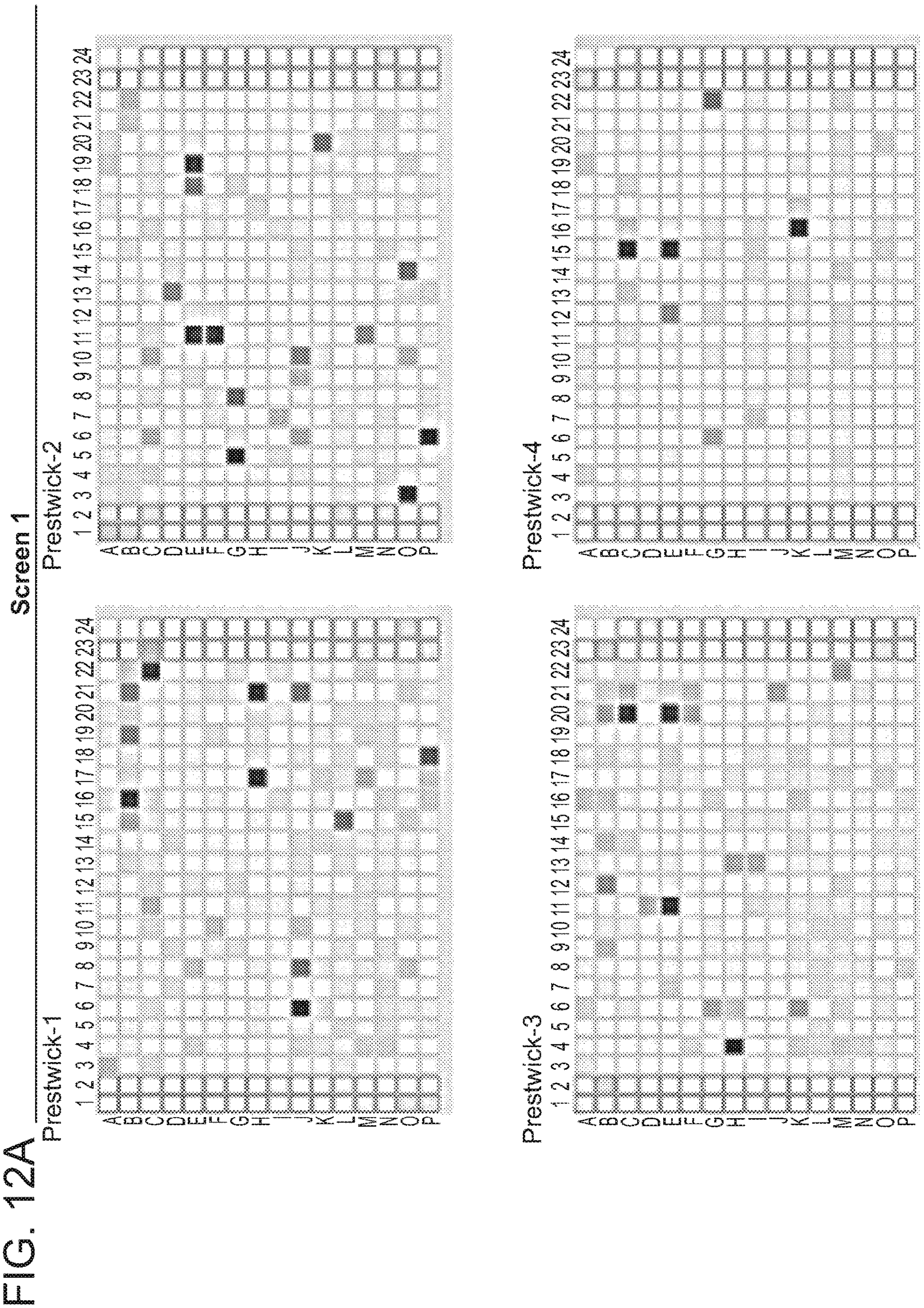
FIGS. 12A-12B depict the drug screen validation and drug concentration assessment.
Figure 12A:
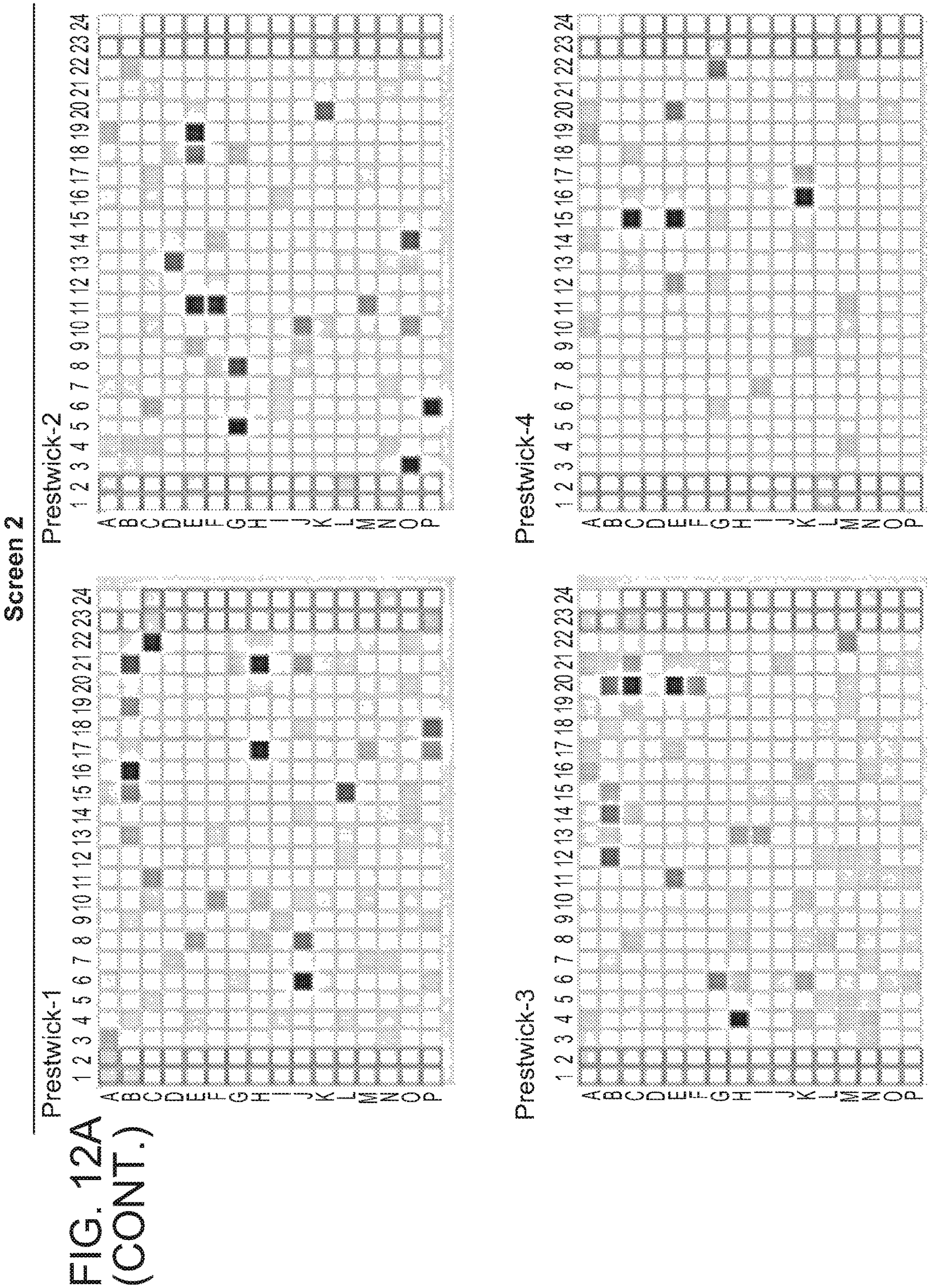

Transcriptional regulation of Ucp1 has been extensively documented. The transcriptional activation of Ucp1 is driven by two known regulatory regions: a proximal region next to the promoter and an enhancer element located 2.5 kb upstream of the transcription start site. By cross-species sequence comparisons, it was noted that additional evolutionarily conserved sequences are present upstream and downstream of the enhancer region (FIG. 1A). To assess the functional significance of these conserved elements, different lengths of the mouse Ucp1 promoter (2.3 kb, 3 kb, 5 kb, and 7 kb) were cloned upstream of a luciferase reporter gene in order to establish stable brown adipocyte cell lines with each of these constructs. Each cell line was tested for luciferase activity in response to known Ucp1 transcriptional activators: CL316,243 (synthetic β3-adrenergic agonist), forskolin (adenylyl cyclase activator), rosiglitazone (PPARγ agonist), and retinoic acids (retinoic acid receptor agonists). The maximal luciferase activity was observed for the 3 kb Ucp1 promoter construct, which includes the known enhancer (FIG. 1B). Longer sequences had diminished activity, suggesting the presence of negative regulatory elements upstream of the enhancer. Based on these pilot studies, the cell line expressing the 3 kb construct was elected for the small molecule screen. Screening was performed with 11,712 compounds (final concentration of 10 μM) in duplicate from a combination of libraries. Duplicate samples showed good reproducibility (FIG. 12A), providing confidence in the results, even though the Z score achieved with known Ucp1 inducers such as forskolin were modest (0.193 with forskolin).

Example 3: Validation of Compounds Using Endogenous Ucp1 Expression

Figure 1C:
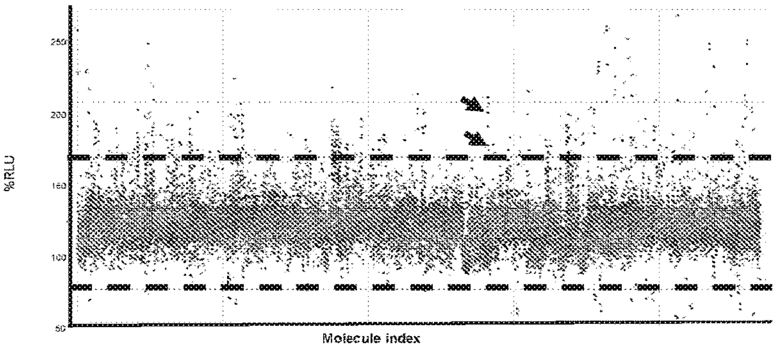

For further characterization, compounds showing increased activation over vehicle of >55% for both duplicates were identified (FIG. 1C). This group comprised 97 molecules, of which 30% had known functions, including several compounds with adrenergic agonist activity. To validate the compounds, brown adipocytes were treated with 92 compounds (excluding known adrenergic agonists) and measured the subsequent endogenous Ucp1 expression by qPCR. Twenty-two compounds induced Ucp1 expression >2-fold during two independent experiments. Most of these compounds also increased expression of Ppargc1a and Pparg. One compound with unknown function, AST 7062601, was selected for further characterization with the aims of understanding its mechanism of action.

Figure 1D:
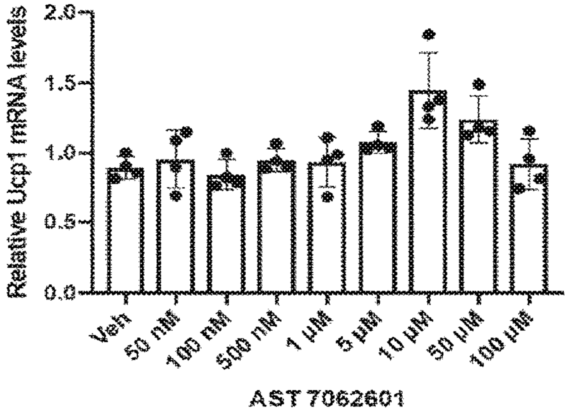
Figure 12B:
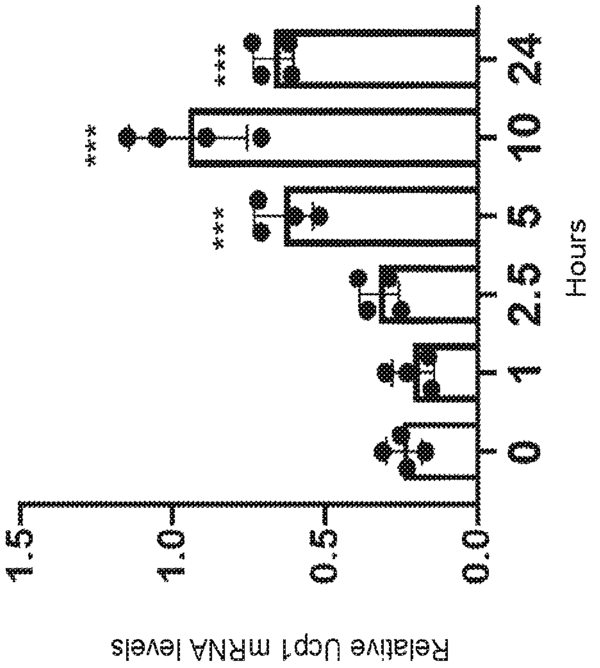

AST 7062601 (or AST070) is an N-(2,3-dihydro-1,4-benzodioxin-6-yl)-2-[(4-oxo-3,4-dihydroquinazolin-2-yl)sulfanyl]acetamide. Titration experiments revealed that AST070 induced Ucp1 expression optimally at a concentration of 10 μM, with lower induction at 1 μM (FIG. 1D). The effect of 10 μM AST070 on Ucp1 expression was observed as early as 5 h and lasted at least 24 h (FIG. 12B).

Figure 1E:
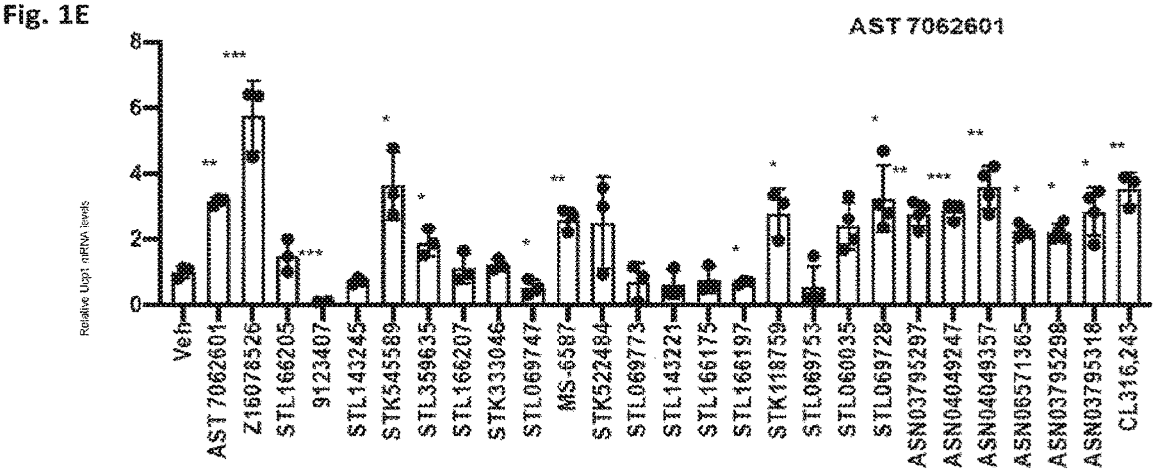
Figures 2A, 2B:
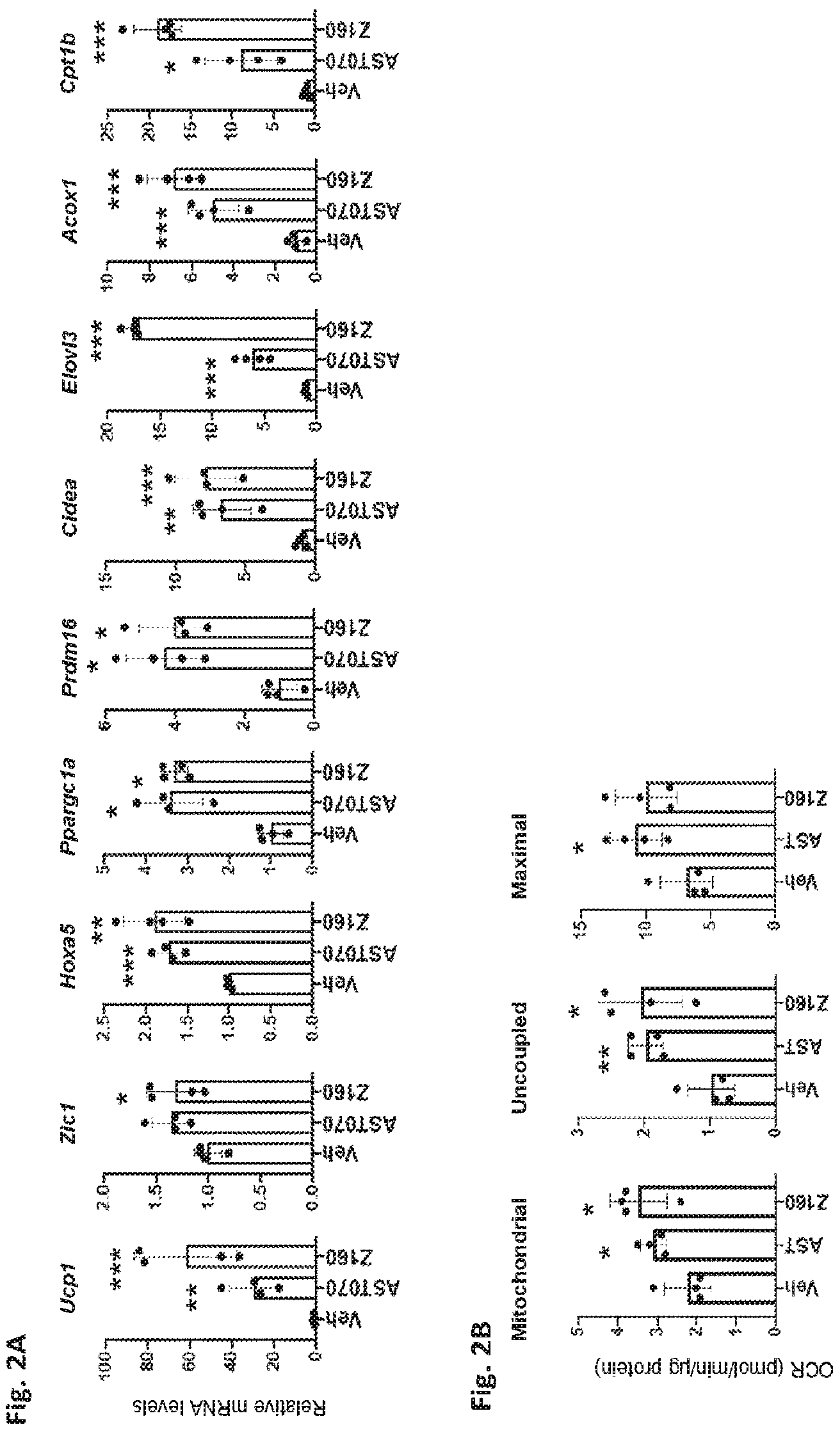
FIGS. 2A-2B depict how AST070 and Z160 activate thermogenic gene expression and mitochondrial activity in mouse immortalized brown adipocytes.
Figure 13:
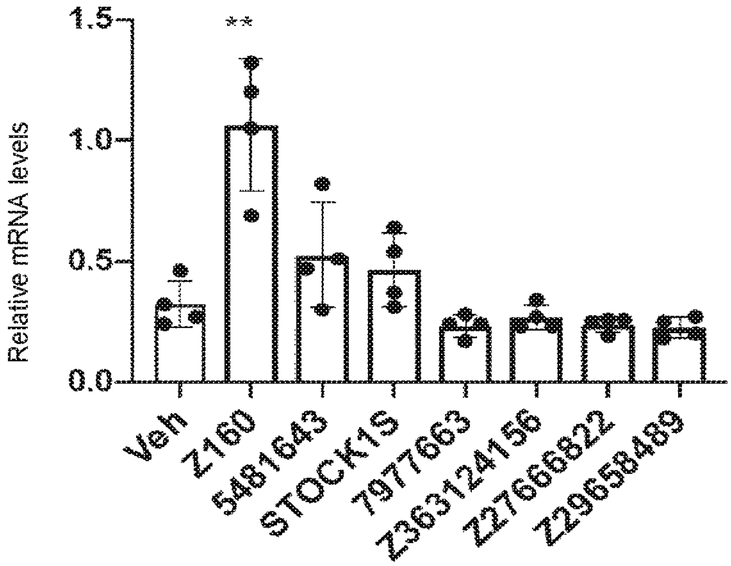
FIG. 13 is a bar graph showing the effects of 6 molecules with deleted functional groups on Ucp1 mRNA compared to AST 706201. Ucp1 expression was measured after overnight treatment in brown adipocytes. Mean±SD. **P<0.01.

To optimize the lead compound, 25 compounds were selected, each with more than 81% identity (Table 2) and assessed for their effect on Ucp1 expression. Many of the 25 compounds induced Ucp1 expression to a similar level as AST070 and to CL316,243 (FIG. 1E). One compound, Z16078526 (Z160), was found to have a greater potency than AST070 on Ucp1 induction. Both AST070 and Z160 robustly induced endogenous Ucp1 expression in primary mouse brown adipocytes (29-fold and 62-fold for AST070 and Z160, respectively; FIG. 2A), which was more pronounced than the drug action in immortalized brown adipocytes (FIG. 1E). AST070, Z160, and related compounds all contain quinazoline, sulfur, acetamide, and benzene chemical groups. Selected compounds (Table 3) which did not contain one of the aforementioned moieties were assessed against AST070 for their effect on Ucp1 mRNA induction. The removal of any of these functional groups blunted the induction of Ucp1 mRNA (FIG. 13).

TABLE 2

| Compounds utilized in lead optimization studies. | |
| --- | --- |
| AST 7062601 | 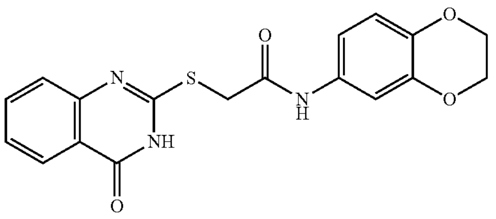 |
| Z16078526 | 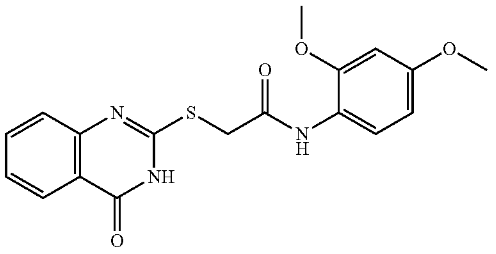 |
| STK545589 | 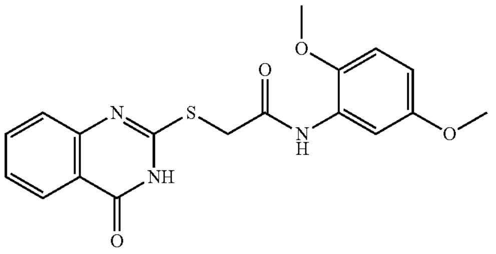 [SMILES: COc1ccc(OC)c(NC(=O)CSc2nc3ccccc3c(=O)[nH]2)c1] |
| STL359835 | 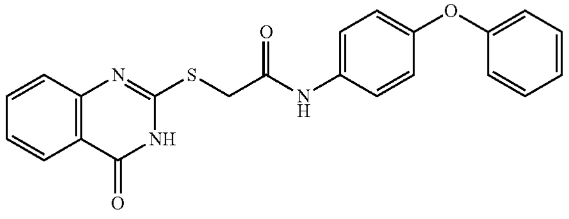 [SMILES: O=C(CSc1nc2ccccc2c(=O)[nH]1)Nc1ccc(Oc2ccccc2)cc1] |

TABLE 2-continued
Compounds utilized in lead optimization studies.
MS-6587
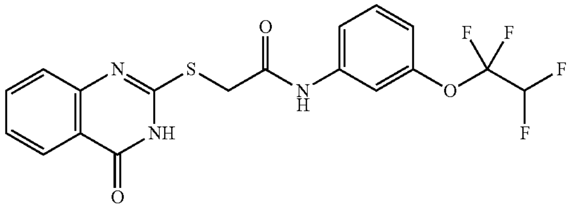 [SMILES: O=C(CSc1nc2ccccc2c(=O)[nH]1)Nc1cccc(OC(F)(F)C(F)F)c1]
STL069728
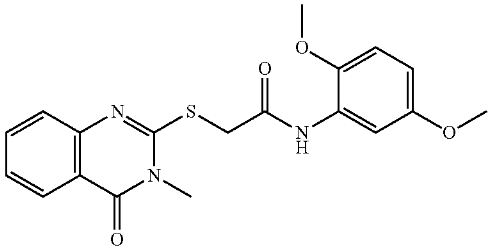 [SMILES: COc1ccc(OC)c(NC(=O)CSc2nc3ccccc3c(=O)n2C)c1]
ASN03795297
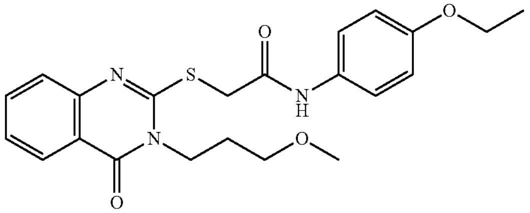 [SMILES: CCOc1ccc(NC(=O)CSc2nc3ccccc3c(=O)n2CCCOC)cc1]
ASN04049247
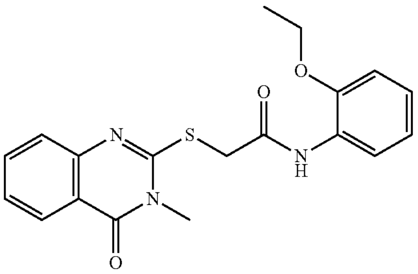 [SMILES: CCOc1ccccc1NC(=O)CSc1nc2ccccc2c(=O)n1C]
ASN04049357
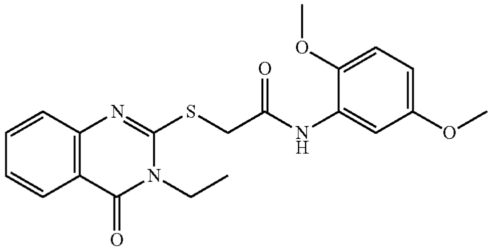 [SMILES: CCn1c(SCC(=O)Nc2cc(OC)ccc2OC)nc2ccccc2c1=O]
ASN06571365
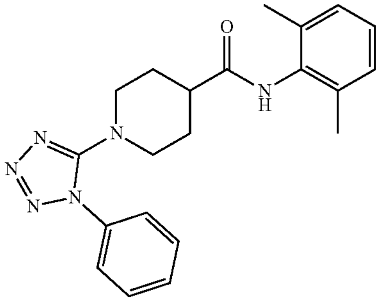 [SMILES: Cc1cccc(C)c1NC(=O)C1CCN(c2nnnn2-c2ccccc2)CC1]

TABLE 2-continued
Compounds utilized in lead optimization studies.
ASN03795298
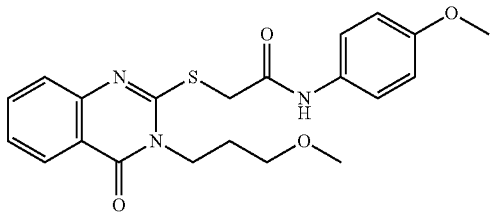 [SMILES: COCCCn1c(SCC(=O)Nc2ccc(OC)cc2)nc2ccccc2c1=O]
ASN03795318
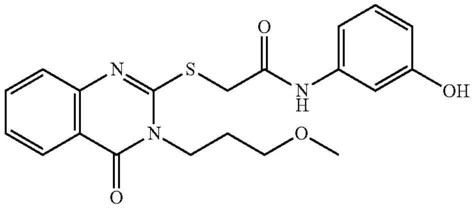 [SMILES: COCCCn1c(SCC(=O)Nc2cccc(O)c2)nc2ccccc2c1=O]
STK118759
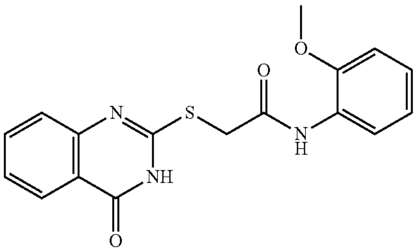 [SMILES: COc1ccccc1NC(=O)CSc1nc2ccccc2c(=O)[nH]1]
STL166205
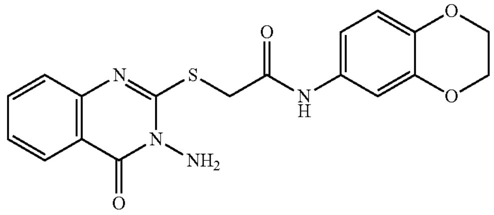 [SMILES: Nn1c(SCC(=O)Nc2ccc3c(c2)OCCO3)nc2ccccc2c1=O]
9123407
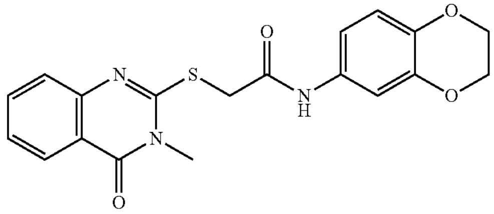 [SMILES: Cn1c(SCC(=O)Nc2ccc3c(c2)OCCO3)nc2ccccc2c1=O]
STK143245
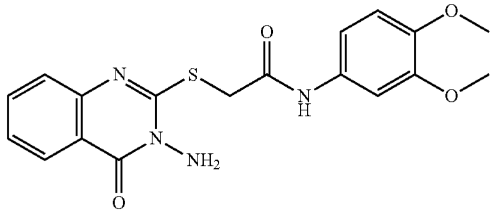 [SMILES: COc1ccc(NC(=O)CSc2nc3ccccc3c(=O)n2N)cc1OC]
STK522484
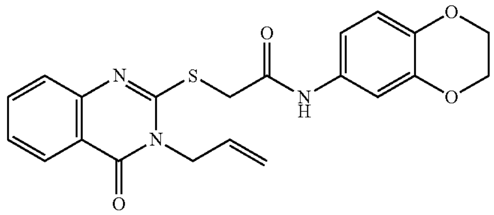 [SMILES: C=CCn1c(SCC(=O)Nc2ccc3c(c2)OCCO3)nc2ccccc2c1=O]

TABLE 2-continued
| Compounds utilized in lead optimization studies. | |
|---|---|
| STL069773 | 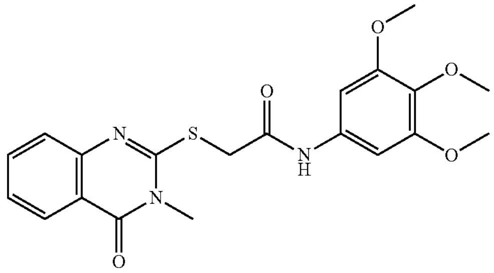 [SMILES: COc1cc(NC(=O)CSc2nc3ccccc3c(=O)n2C)cc(OC)c1OC] |
| STL166197 | 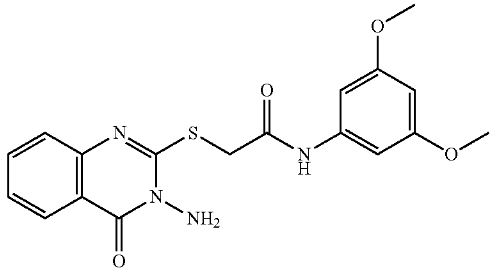 [SMILES: COc1cc(NC(=O)CSc2nc3ccccc3c(=O)n2N)cc(OC)c1] |
| STL166207 | 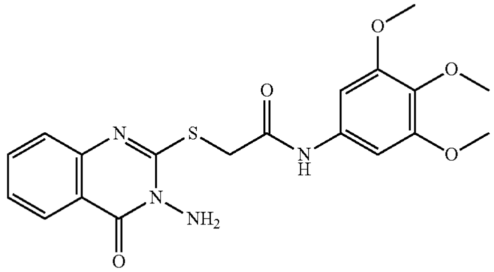 [SMILES: COc1cc(NC(=O)CSc2nc3ccccc3c(=O)n2N)cc(OC)c1OC] |
| STK333046 | 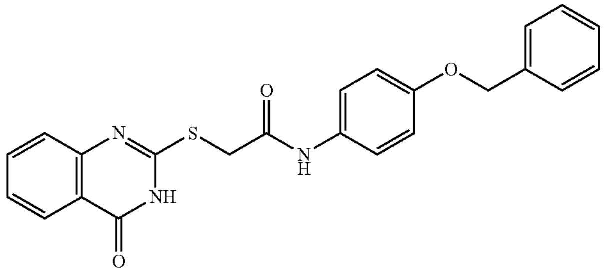 [SMILES: O=C(CSc1nc2ccccc2c(=O)[nH]1)Nc1ccc(OCc2ccccc2)cc1] |
| STL069747 | 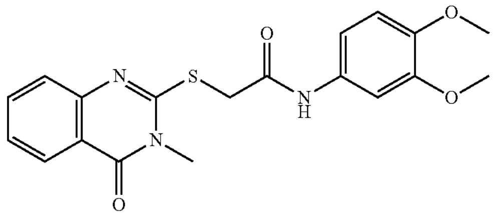 [SMILES: COc1ccc(NC(=O)CSc2nc3ccccc3c(=O)n2C)cc1OC] |
| STL143221 | 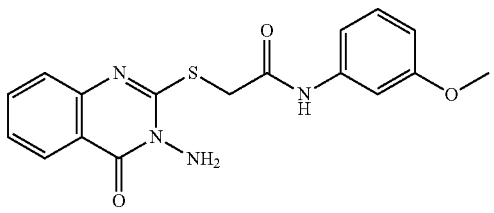 [SMILES: COc1cccc(NC(=O)CSc2nc3ccccc3c(=O)n2N)c1] |

TABLE 2-continued
| Compounds utilized in lead optimization studies. | |
|---|---|
| STL166175 | 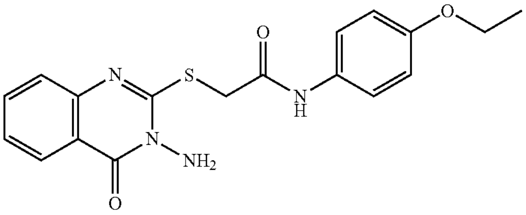 [SMILES: CCOc1ccc(NC(=O)CSc2nc3ccccc3c(=O)n2N)cc1] |
| STL060035 | 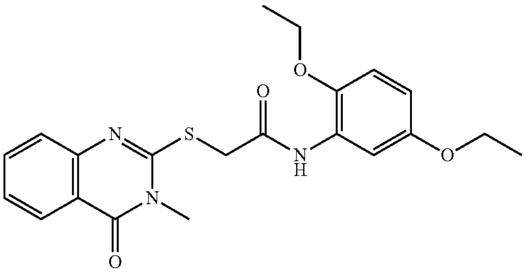 [SMILES: CCOc1ccc(OCC)c(NC(=O)CSc2nc3ccccc3c(=O)n2C)c1] |
| STL069753 | 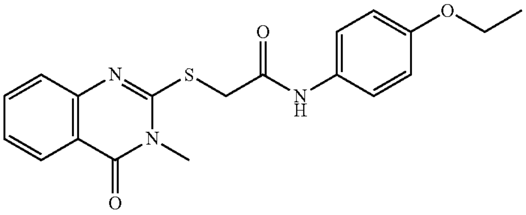 [SMILES: CCOc1ccc(NC(=O)CSc2nc3ccccc3c(=O)n2C)cc1] |
TABLE 3
Chemical structures of 6 compounds with deleted functional groups assessed against AST070.
| Deleted group compared to AST070 | Compounds |
|---|---|
| Without acetamide/benzene | 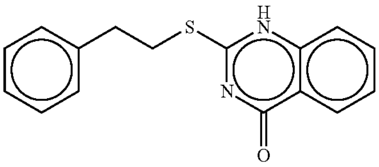 5481643 |
| | 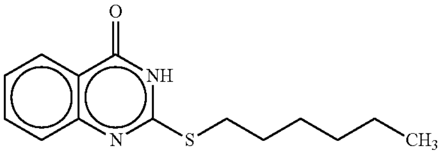 STOCK1S |
| Without quinazoline | 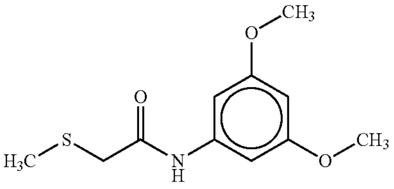 7977663 |

TABLE 3-continued

Chemical structures of 6 compounds with deleted functional groups assessed against AST070.

| Deleted group compared to AST070 | Compounds |
|---|---|
| | 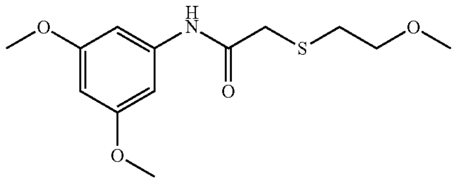<br>Z363124156 |
| Without sulfur | 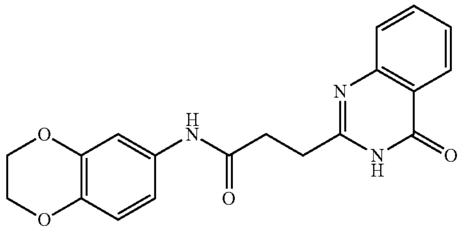<br>Z27666822 |
| | 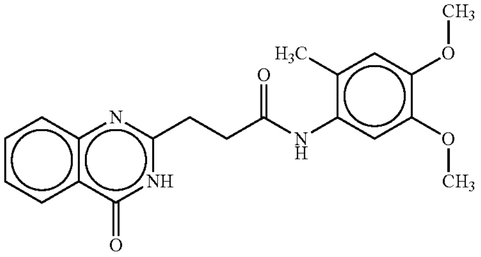<br>Z29658489 |

Figure 14A:
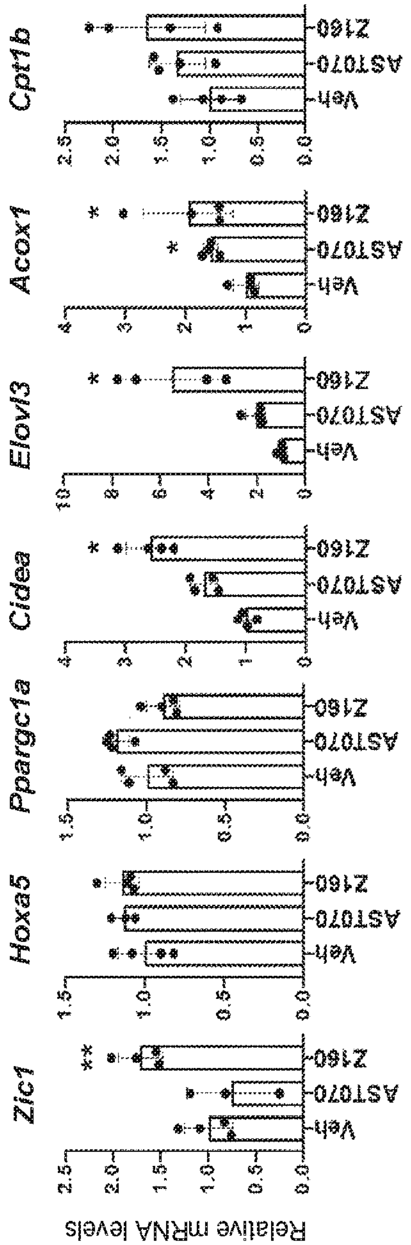
FIGS. 14A-14B depict the activation of thermogenic gene expression in mouse immortalized brown adipocytes.
Figure 14B:
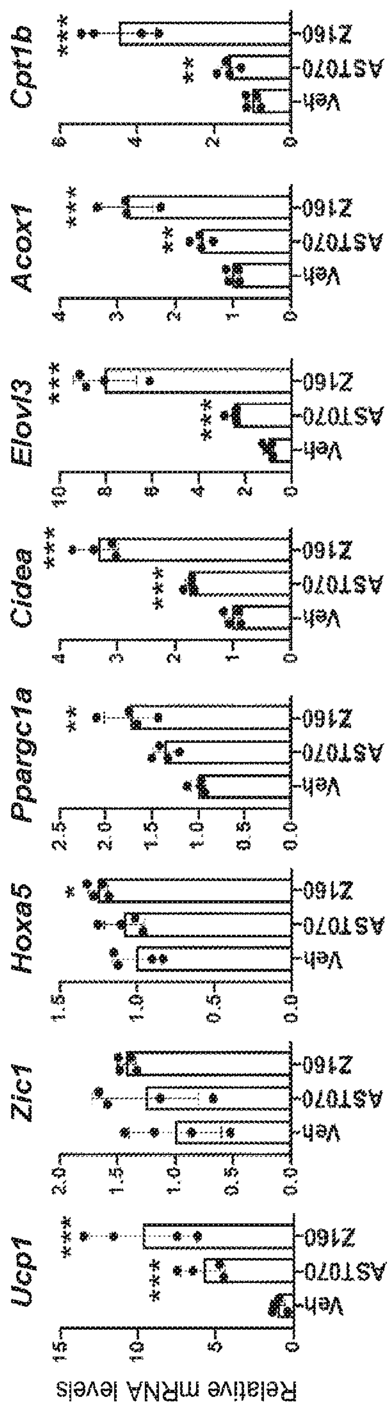

Example 4: AST070 and Z160 Promote Mitochondrial Activation in Brown and White Adipocytes The effects of AST070 and Z160 on adipocyte metabolism were probed by analyzing gene expression and mitochondrial respiration. Treatment of primary (FIG. 2A) and immortalized brown adipocytes (FIG. 14) with AST070 or Z160 promoted expression of markers of brown adipocyte identity, and of genes involved in mitochondrial function and fatty acid oxidation. Larger effects were observed in primary compared to immortalized cells. To investigate whether the compounds affected mitochondrial function, brown adipocytes were treated with AST070 and Z160 before assessing mitochondrial respiration with a Seahorse XF analyzer. Both AST070 and Z160 increased mitochondrial respiration, and more specifically, uncoupled respiration (FIG. 2B). Maximal respiration was also significantly elevated by AST070, and showed the same trend for Z160, suggesting an increase in mitochondrial reserve capacity.

Figures 3A, 3B, 3C, 3D:
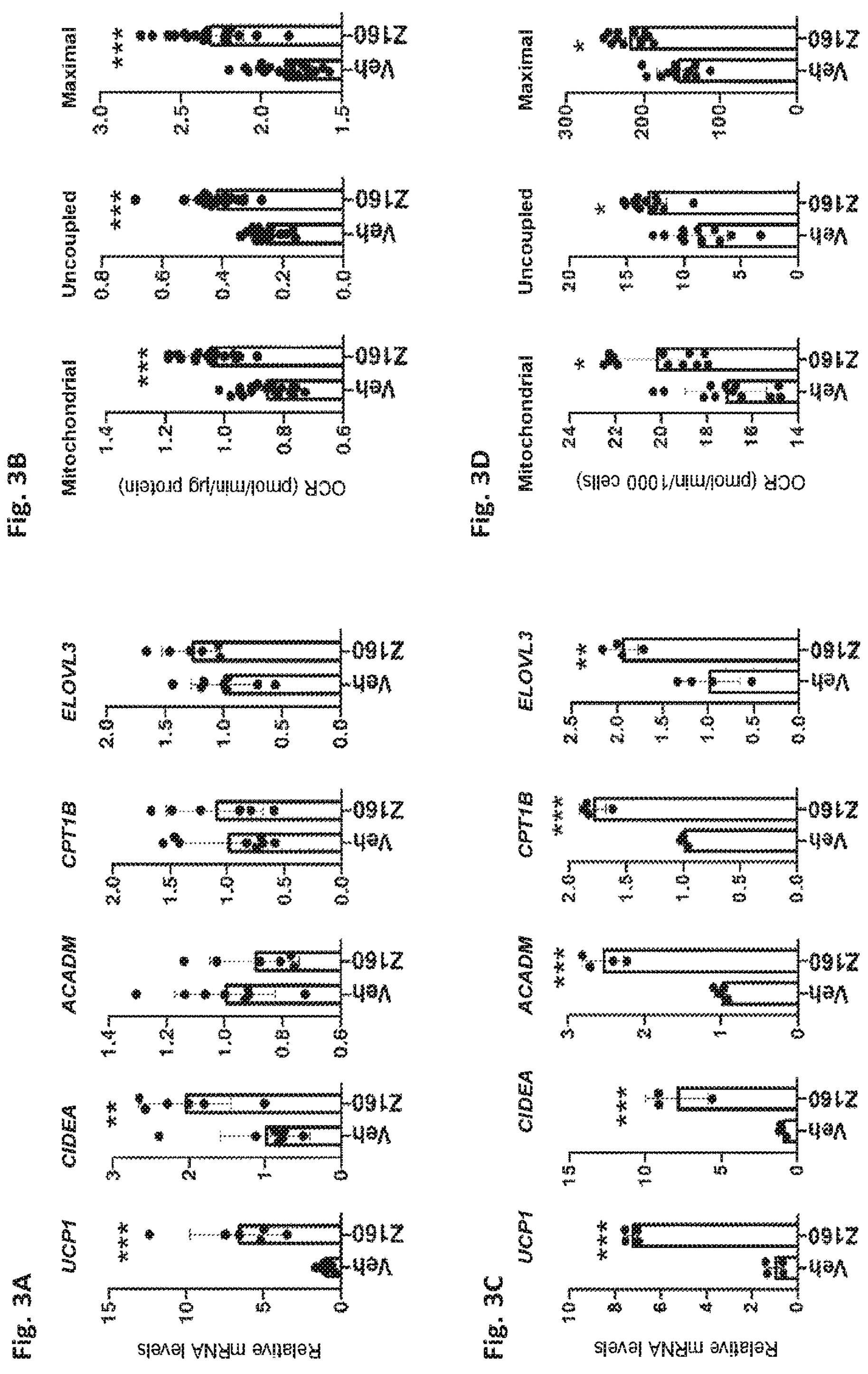
FIGS. 3A-3D depict how Z160 activates thermogenic gene expression and mitochondrial activity in immortalized human brown and white adipocytes.
Figure 4A:
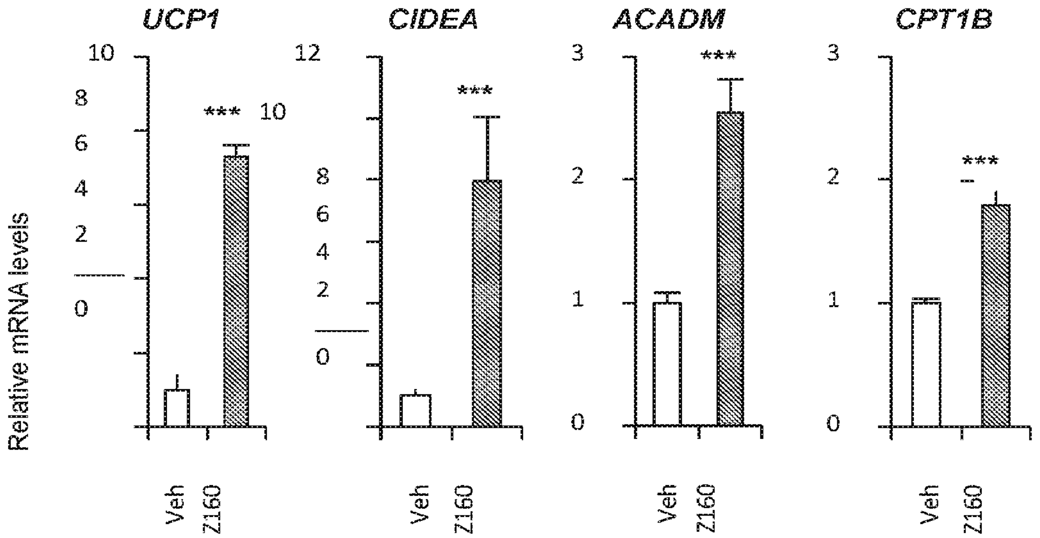
FIGS. 4A-4B depict how Z160 activates thermogenic gene expression and mitochondrial activity in human white adipocytes.
Figure 4B:
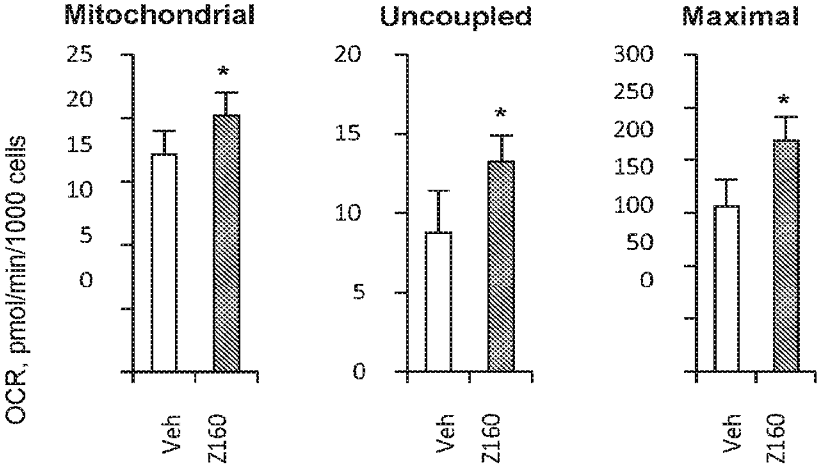

To validate these findings in a human cellular model, an immortalized human brown adipocyte cell line was employed. Z160 induced UCP1 expression nearly 7-fold, and increased expression of CIDEA (FIG. 3A). Importantly, Z160 also increased mitochondrial respiration (primarily uncoupled respiration), as well as maximal respiration, in the human brown adipocyte cell line (FIG. 3B) Given that white adipocytes have the ability to express brown adipocyte properties with specific metabolic stimuli, the ability of Z160 to influence brown adipocyte character in human white adipocytes was assessed. Interestingly, Z160 also induced UCP1 expression 7-fold, and greatly increased expression of CIDEA, ACADM, CPT1B and ELOVL3 (FIG. 3C). Similarly to the human brown adipocytes, Z160 also increased mitochondrial respiration (uncoupled), as well as maximal respiration, in the human white adipocyte cell line (FIG. 3D). Together, these results indicate that Z160 activates mitochondrial respiration in mouse brown adipocytes as well as in human brown and white adipocytes.

Figure 5A:
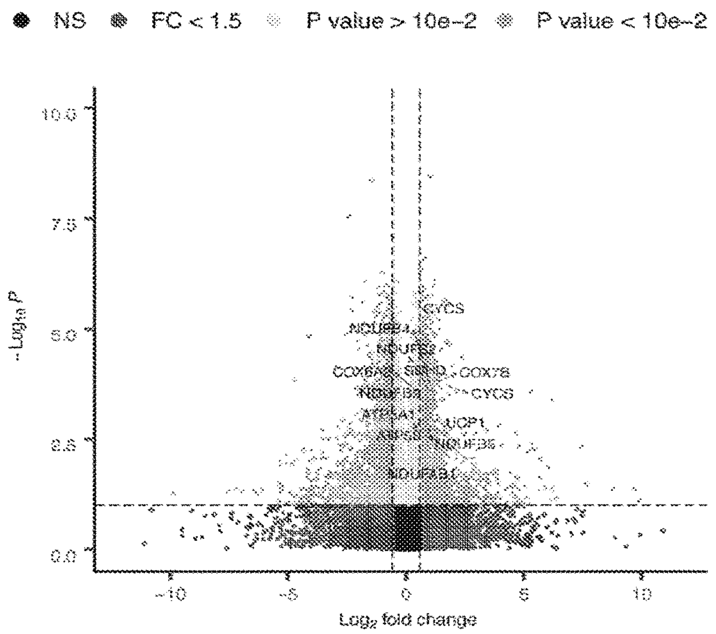
FIGS. 5A-5C depict the categories of genes regulated by Z160 in mouse immortalized brown adipocytes. Global gene expression analysis was performed by microarray hybridization of RNA from brown adipocytes treated with vehicle or with Z160. Genes with >1.5-fold alterations in gene expression in response to Z160 were identified and subjected to functional enrichment analysis (DAVID) using the GOTERM cellular component categories. The number of genes for each term, and multiple testing correction (Benjamini $p<0.001$) are presented.
Figure 5B:
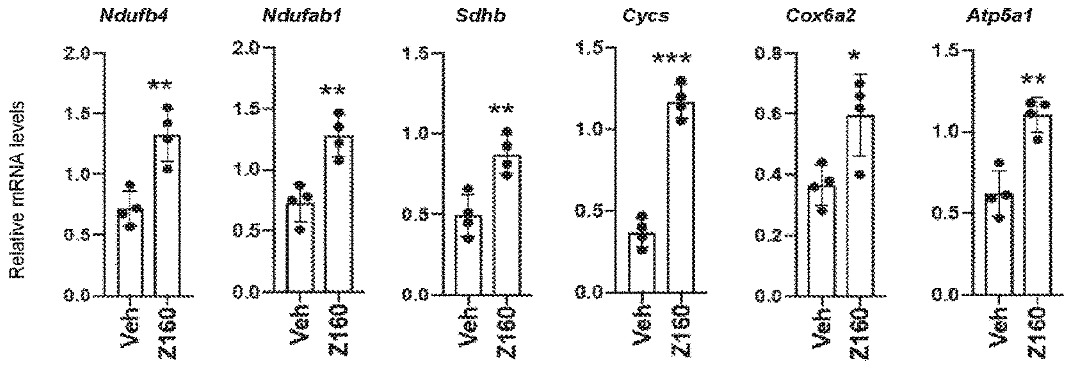
Figure 5C:
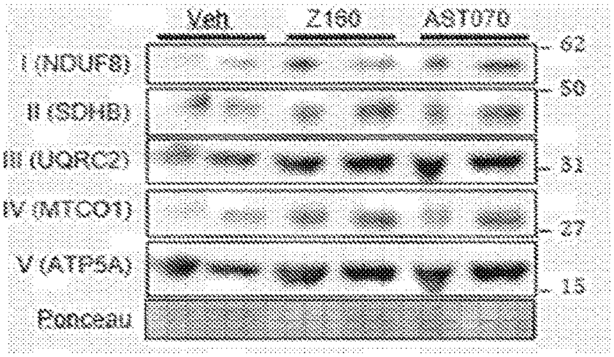

Example 5: Global Gene Expression Analysis Highlights Z160 Effects on Energy Metabolism To assess the effects of Z160 on global transcription in mouse brown adipocytes, microarray analysis of RNA isolated from immortalized brown adipocytes treated with either vehicle or Z160 was performed. Compared to vehicle-treated cells, 581 and 504 probes were up-regulated and down-regulated, respectively, by at least 1.5-fold. Consistent with the qPCR results obtained, Ucp1 was increased 2.5-fold in response to Z160, placing it in the top 20 up-regulated genes. Functional annotation was carried out on the genes up-regulated or down-regulated >1.5-fold by Z160 using the DAVID functional annotation tool. Z160 treatment increased expression of genes in mitochondrial categories (FIG. 5A), and down-regulated expression of genes that are distinct from mitochondrial function (Table 4). In addition to Ucp1, up-regulated genes included five belonging to mitochondrial complex I (Ndufb2, Ndufb4, Ndufb5, Ndufb9, Ndufab1), one associated with complex II (Sdhd) as well as cytochrome C (Cycs), two subunits of complex IV (Cox6a2 and Cox7b), and two of complex V (Atp5a1, Atp5e). The results of the microarray were corroborated using qPCR for representative genes from each electron transport chain complex (FIG. 5B). A slight enhancement in mitochondrial complex protein abundance was also observed in isolated mitochondria by Western blot (FIG. 5C).

TABLE 4

Showing up- and down-regulation by Z160. Using the GOTERM cellular component categories. The number of genes for each term, and multiple testing correction (Benjamini $p < 0.001$) are presented.

| Term | Genes | Benjamini |
|---|---|---|
| GO cellular component Up | | |
| Mitochondrion | 88 | 1.1E−10 |
| Mitochondrial inner membrane | 27 | 1.4E−4 |
| GO cellular component Down | | |
| Extracellular exosome | 119 | 4.2E−14 |
| Proteinaceous extracellular matrix | 35 | 5.3E−13 |
| Extracellular region | 86 | 3.6E−12 |
| Cell surface | 45 | 9.2E−11 |
| Extracellular space | 72 | 1.6E−9 |
| Basement membrane | 17 | 6.8E−9 |
| Focal adhesion | 25 | 9.5E−5 |
| Cytoplasm | 178 | 4.7E−4 |

Example 6: Z160 Stimulates Thermogenesis in the Mouse

Figure 6A:
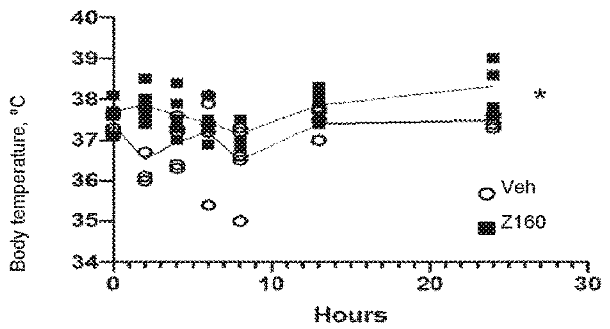
FIGS. 6A-6D depict body temperature and mitochondrial gene expression in mouse BAT. Z160 at 1.5 mg/kg body weight was injected subcutaneously. Results were analyzed 20 h later.
Figure 6B:
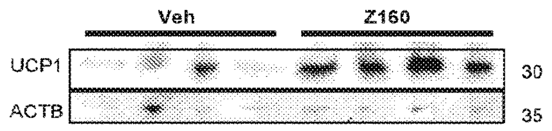
Figure 6C:
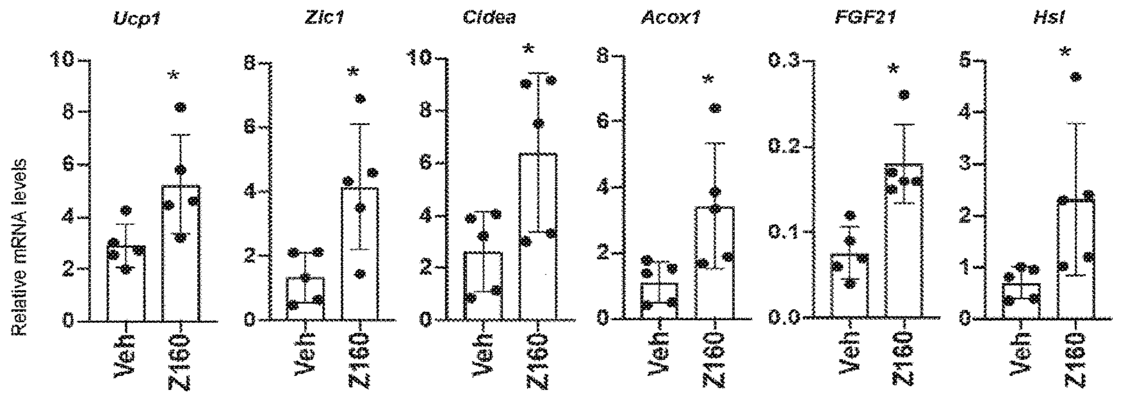
Figure 6D:
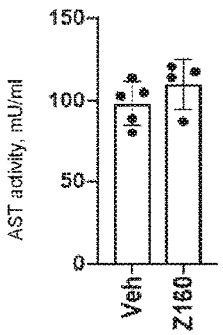

The ability of Z160 to stimulate thermogenesis in vivo in C57BL/J mice was analyzed. A single subcutaneous injection of the drug led to an increase in body temperature by 0.8° C. when measured 24 h later (37.5° C. vs. 38.3° C., $p<0.05$), consistent with activated thermogenesis (FIG. 6A). Additionally, BAT from treated mice had elevated Ucp1 mRNA and protein levels, and enhanced expression of several genes implicated in mitochondrial function and lipolysis (FIG. 6B, FIG. 6C). No liver toxicity was observed as assessed by circulating aspartate aminotransferase (AST) levels (FIG. 6D). Plasma glucose levels were not affected by Z160 (172.8±26.0 mg/dl vs. 157.6±26.2 mg/dl, for vehicle and Z160-treated mice, respectively).

Example 7: Z160 Activates PKA

Figure 7A:
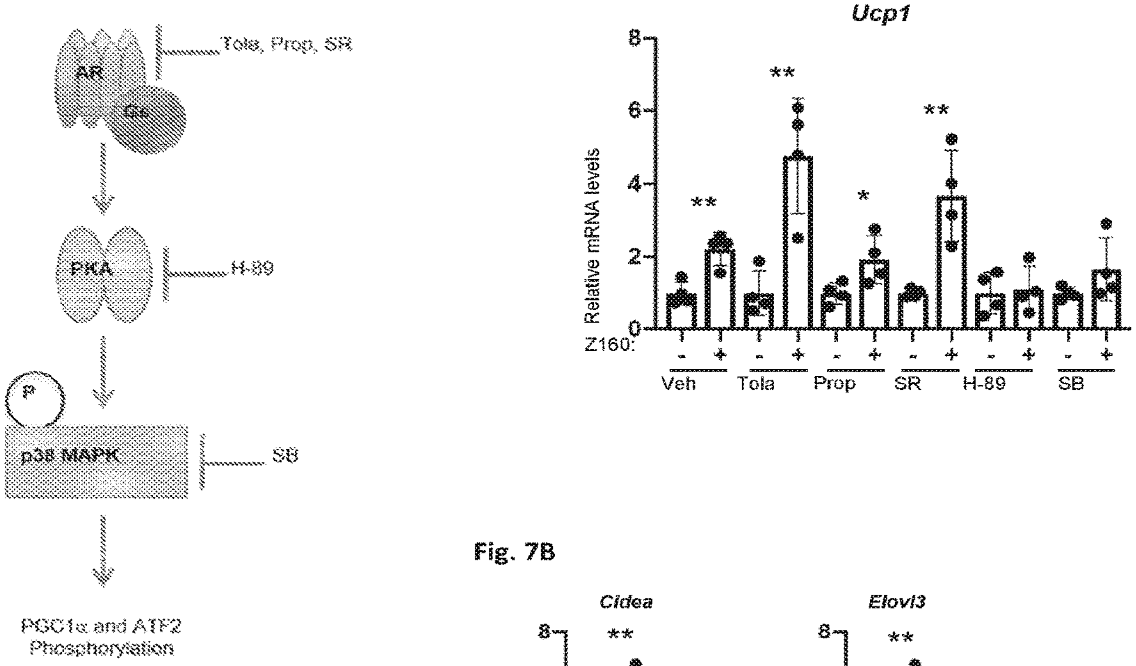
FIGS. 7A-7F depict the analyses of the activation of protein kinase A (PKA).
Figure 7B:
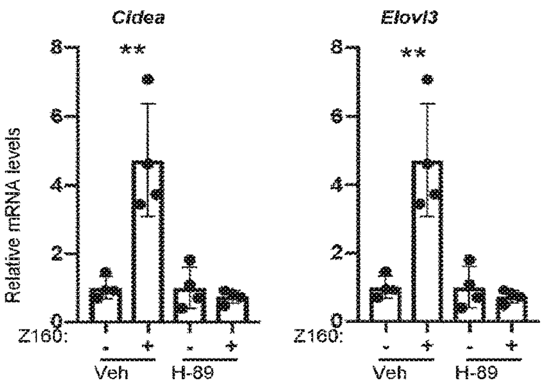

To understand the mechanism by which Z160 and related compounds enhance mitochondrial respiration, brown adipocytes were treated with Z160 in the presence of several known antagonists in the adrenergic receptor signaling pathway. Treatment with vehicle or non-selective α-(tolazoline, Tola) and β-(propranolol, Prop) adrenergic receptor antagonists did not prevent the induction of Ucp1 mRNA by Z160 (FIG. 7A). The same result was obtained with β3-adrenergic receptor antagonists (SR59230A, SR). By contrast, treatment with antagonists of PKA (H-89) or p38 MAPK (SB202190, SB) blocked the effect of Z160, suggesting that Z160 requires PKA activity to exert its effect on Ucp1 expression. Accordingly, the Z160 enhancement of Cidea and Elovl3 expression was also blunted by treatment with H-89 (FIG. 7B).

Figure 7C:
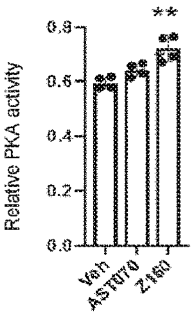
Figure 7D:
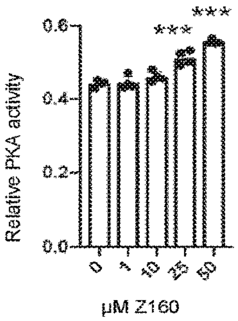
Figure 7E:
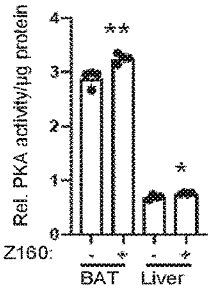
Figure 7F:
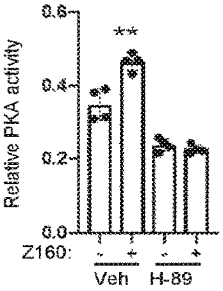

Based on the aforementioned results, the ability of either AST070 or Z160 to influence PKA activity was investigated using a solid phase ELISA. First, PKA activity was measured in immortalized brown adipocytes after overnight treatment with 10 μM AST070 or Z160. Treatment with either compound significantly increased PKA activity in an expected range (FIG. 7C). Next, lysate from brown adipocytes was treated with different Z160 concentrations for 30 min before the PKA assay. The highest Z160 concentrations (25 μM and 50 μM) showed a significant increase in PKA activity, indicating that the compound activates PKA even when the cells were disrupted (FIG. 7D). Importantly, 25 μM Z160 also stimulated PKA activation in mouse BAT or liver extracts (FIG. 7E). To confirm the results, cell lysates were treated for 10 min with PKA antagonist H-89 (500 μM) followed by 30 min incubation with Z160 (50 μM). Pre-incubation with the PKA antagonist reduced the PKA activity and negated the Z160 response (FIG. 7F).

Example 8: Z160 Promotes p38 MAPK Phosphorylation and Lipolysis

Figure 8A:
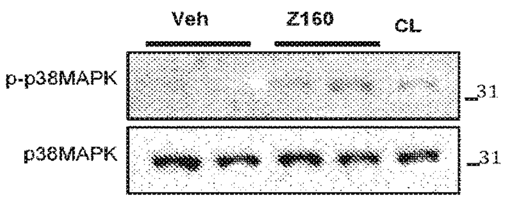
FIGS. 8A-8D depict how Z160 promotes p38 MAPK phosphorylation and lipolysis
Figure 8B:
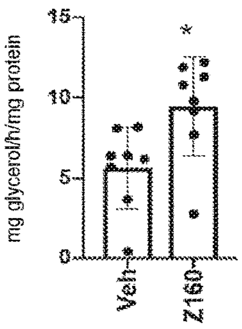
Figure 8C:
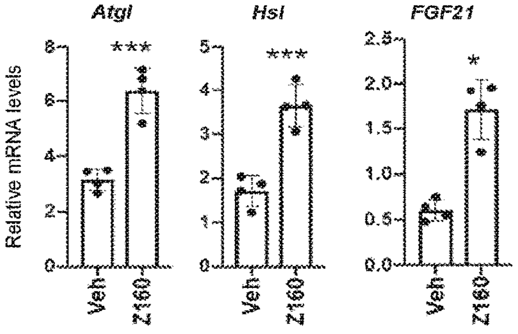
Figure 8D:
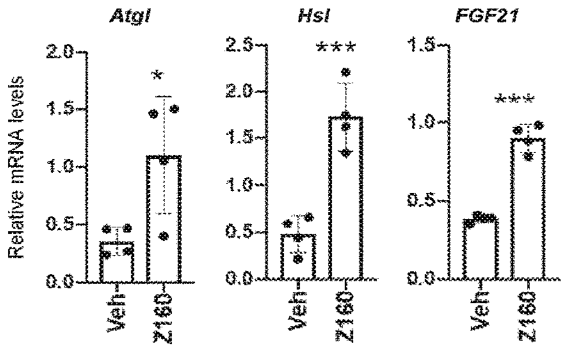

The demonstration that Z160 influences PKA activity inspired a further investigation as to its effects on pathways downstream of PKA activation. In adipocytes, PKA indirectly activates p38 MAPK and promotes lipolysis. Thus, the Z160-induced PKA activation was further characterized by first analyzing p38 MAPK phosphorylation. As depicted in FIG. 8A, Z160 caused p38 MAPK phosphorylation to a similar level as CL316,243. Additionally, Z160 induced lipolysis in brown adipocytes (FIG. 8B), and increased expression of lipolytic enzymes (adipose triglyceride lipase, Atgl; hormone-sensitive lipase, Hsl) and FGF21 (a lipolytic mediator) at the mRNA level in both immortalized (FIG. 8C) and primary brown adipocytes (FIG. 8D).

Figure 16A:
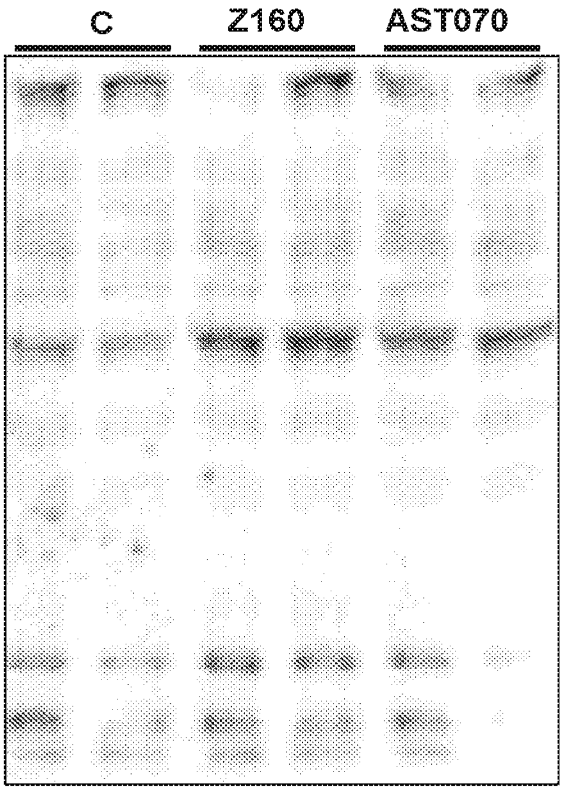
FIGS. 16A-16B depict the phosphorylation of PKA substrates and the mRNA levels in primary brown adipocytes.
Figure 16B:
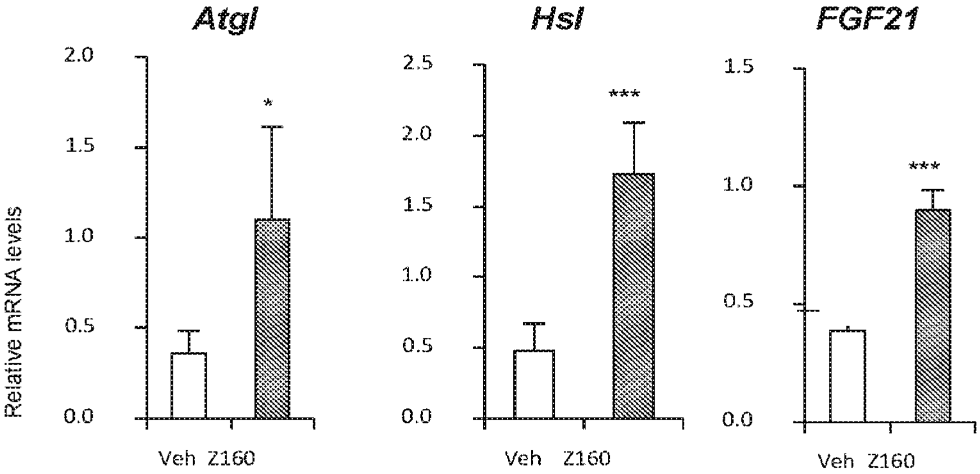

It was suspected that the Z160-induced PKA activation may trigger phosphorylation of other PKA targets. Thus, to interrogate this hypothesis, a specific phosphor-(Ser/Thr) PKA substrate antibody was used to assess the phosphorylation pattern of brown adipocytes after AST070 or Z160 treatment. Both compounds increased the levels of phosphorylation of several proteins (FIG. 16A). Additionally, Z160 induced lipolysis in brown adipocytes (FIG. 7B), and increased expression of lipolytic enzymes (adipose triglyceride lipase, Atgl, hormone-sensitive lipase, Hsl) and FGF21 (a lipolytic mediator) at the mRNA level (FIG. 7C). The same results were observed when primary brown adipocytes were treated with Z160 (FIG. 16B).

Example 9: Z160 Modifies AKAP Protein Conformation and the Mitochondrial PKA/AKAP Interaction in Brown Adipocytes The demonstration that Z160 has an effect on PKA activity when added to cellular extracts (e.g., FIG. 7D, FIG. 7E) suggested an effect of the compound directly on PKA or functionally associated proteins. The PKA tetramer consists of two catalytic and two regulatory subunits. In the mouse, these are catalytic subunits C-α and C-β, and regulatory subunits RI and RII, each with α and β isoforms (RI-α, RI-β, RII-α, RII-β). PKA is also bound to a family of anchoring proteins, A-kinase anchoring proteins (AKAPs), which allow the compartmentalization of cAMP signaling. To investigate whether Z160 binds PKA complex proteins, two techniques were applied both of which rely on ligand-induced alterations in protein stability: Cellular Thermal Shift Assay (CETSA) and Drug Affinity Responsive Target Stability (DARTS). CETSA is based on the principle that ligand binding will change the temperature at which a protein starts to unfold and aggregate, while DARTS relies on the protection of a protein from proteolysis upon specific binding to a small molecule.

Figures 9A, 9B, 9C, 9D, 9E:
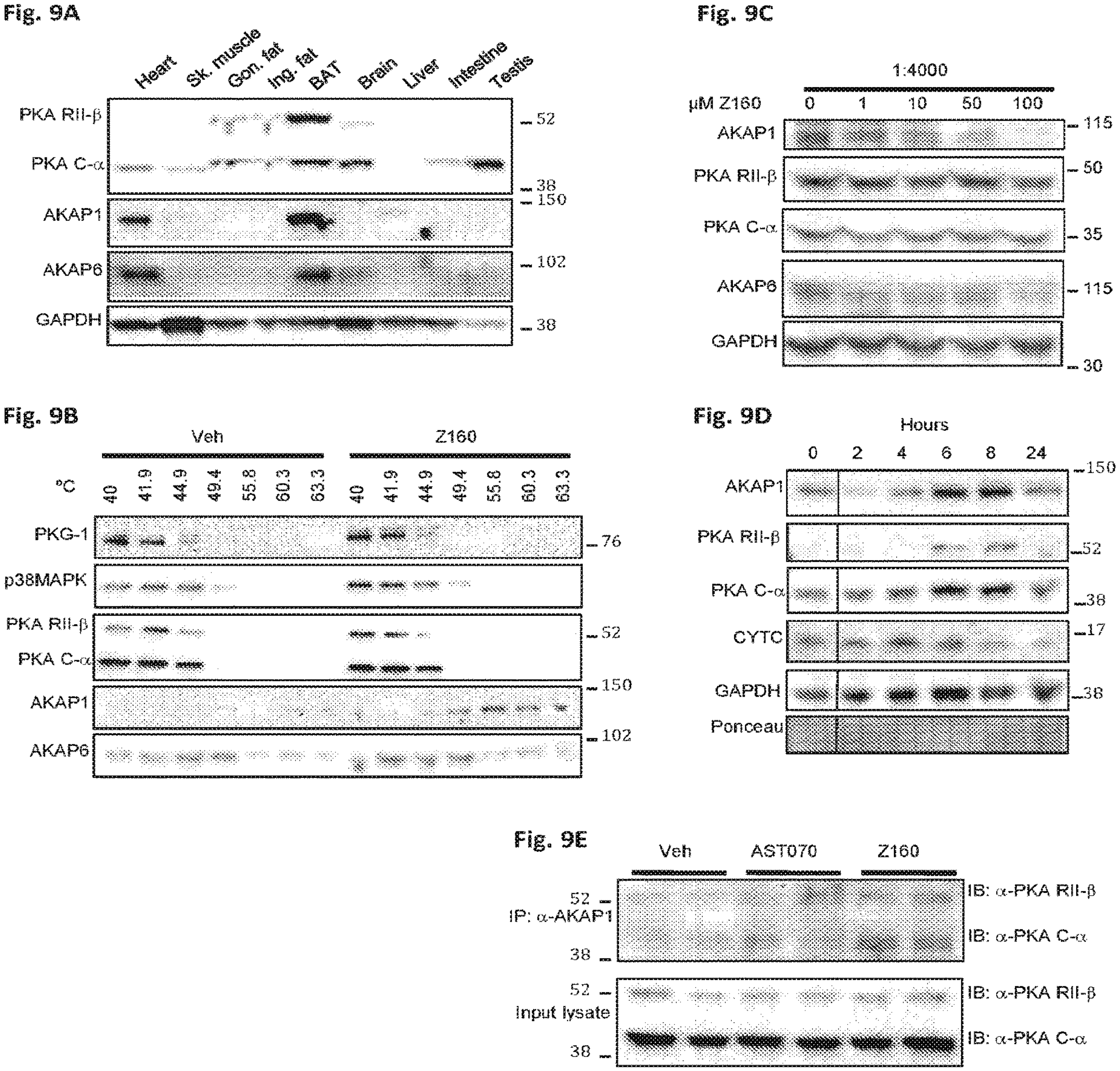
FIGS. 9A-9E depict how Z160 modifies AKAP protein conformation and localization in brown adipocytes.

The potential interaction of Z160 with PKA subunits and AKAPs was assessed first by identifying which PKA subunits and AKAP isoforms are normally present in BAT. Robust protein levels were observed in BAT for PKA C-α and RII-β subunits, AKAP1, and AKAP6 (also known as mAKAP) (FIG. 9A). To perform the CETSA assays, cultured brown adipocytes were incubated with 10 μM Z160 for 8 h, after which the thermal shift was analyzed by Western blot. The PKA subunits expressed in BAT (C-α and RII-β) did not show differences in denaturation in the presence of Z160 (FIG. 9B). However, AKAP1 showed altered protein stability in the presence of Z160: Z160 increased the heat stability of AKAP1 (compare vehicle and Z160 heated at 55.8-63.3° C.), suggesting that Z160 may interact with this protein (FIG. 9B). By contrast, Z160 did not influence the heat stability of AKAP6, p38 MAPK, or cGMP-dependent kinase 1 (PKG-1).

Figure 15A:
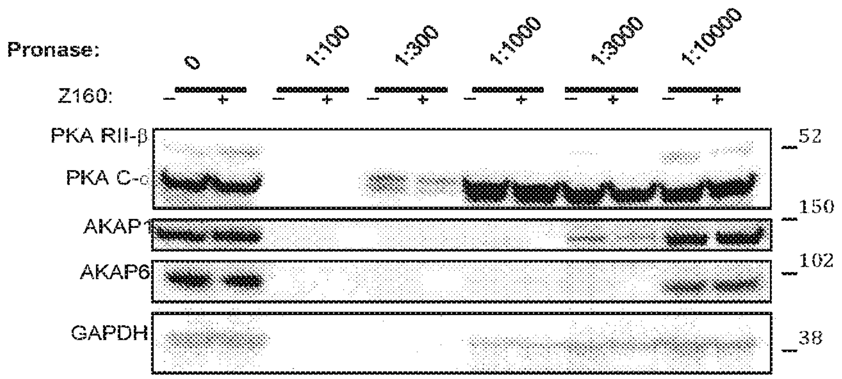
FIGS. 15A-15B depict the modification of AKAP protein confirmation in brown adipocytes.
Figure 15B:
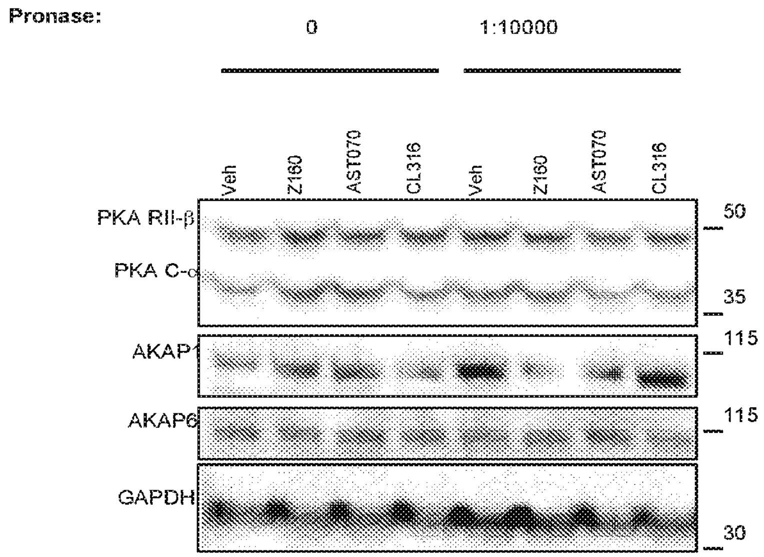

To provide further evidence for an interaction between Z160 and AKAP1, DARTS assays were employed. Lysates from brown fat were treated with different Z160 concentrations for 1 h followed by pronase digestion and immunoblotting. Representative data shown in FIG. 9C indicate that the presence of Z160 altered pronase susceptibility of AKAP1 (compare with and without Z160 at a pronase concentration of 1:4000). The protease susceptibility of other proteins tested was not influenced by the presence of Z160. The effect of Z160 on AKAP1 was confirmed using mouse brown adipocyte extracts (FIG. 15A). Importantly, the effect of AST070 or Z160 on AKAP1 was not observed with CL316,243, a chemically unrelated agent known to stimulate Ucp1 expression (FIG. 15B).

AKAP1 is known to localize PKA to the surface of mitochondria and to relay cAMP signaling for mitochondrial functions. Inspired by this information, an inquiry as to whether treatment with the reported compounds could alter the binding of AKAP1 to mitochondria was undertaken. Analysis began by treating brown adipocytes with Z160 and isolated mitochondria at different times. In the presence Z160, AKAP1 protein levels were increased in the mitochondrial fraction after 6-8 h, suggesting that it may influence the localization of AKAP1 (FIG. 9D). In parallel, PKA subunits showed increased mitochondrial association after 6-8 h of Z160 treatment. By contrast, the levels of CYTC and GAPDH in the mitochondrial fraction were not altered by the compound. Finally, an analysis of the extent to which Z160 enhances interactions between AKAP1 and PKA subunits, a mechanism that may promote the localization of PKA at mitochondria. Brown adipocytes were treated with Z160 or AST070 for 7 h and cell lysates were precipitated by anti-AKAP1 antibody and immunoblotted with anti-PKA C-α and RII-β (FIG. 9E). The signal for PKA subunit precipitation by AKAP1 was slightly enhanced after treatment, especially with Z160, suggesting that the compounds increase the interaction between AKAP1 and the PKA subunits.

Figure 10A:
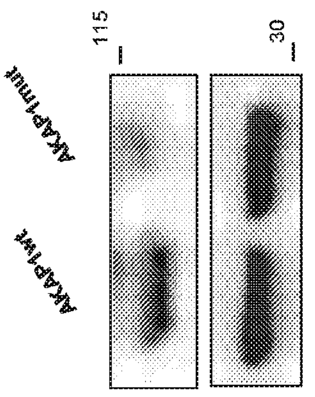
FIGS. 10A-10B depict the generation and characterization of an AKAP1 mutant brown adipocyte cell line.
Figure 10B:
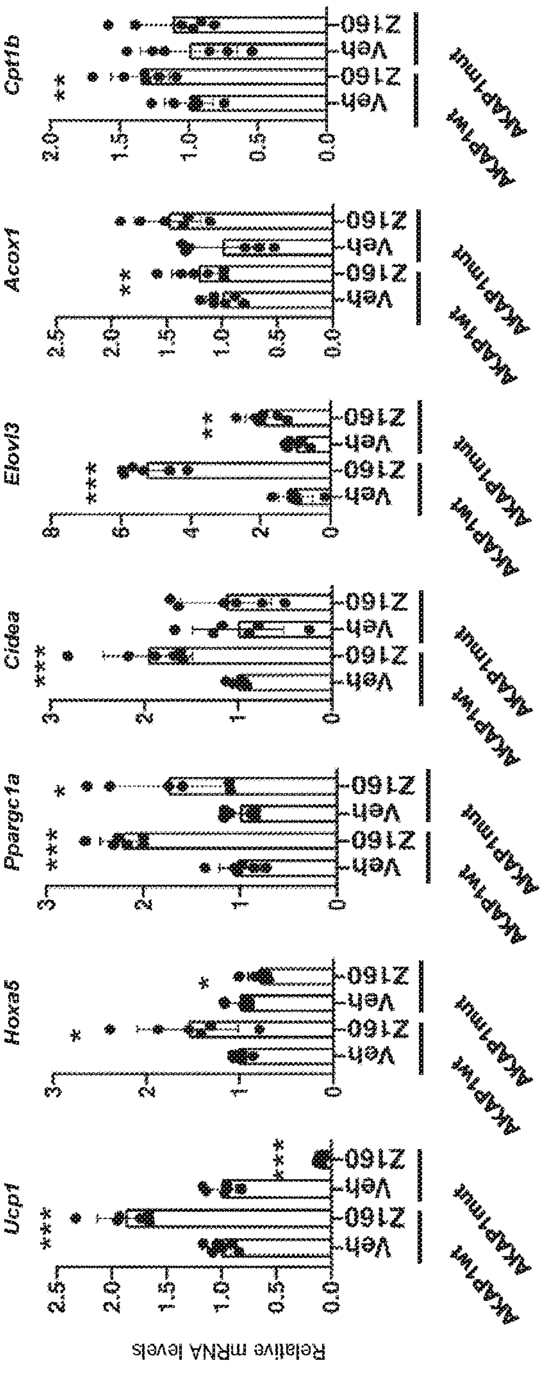
Figure 11:
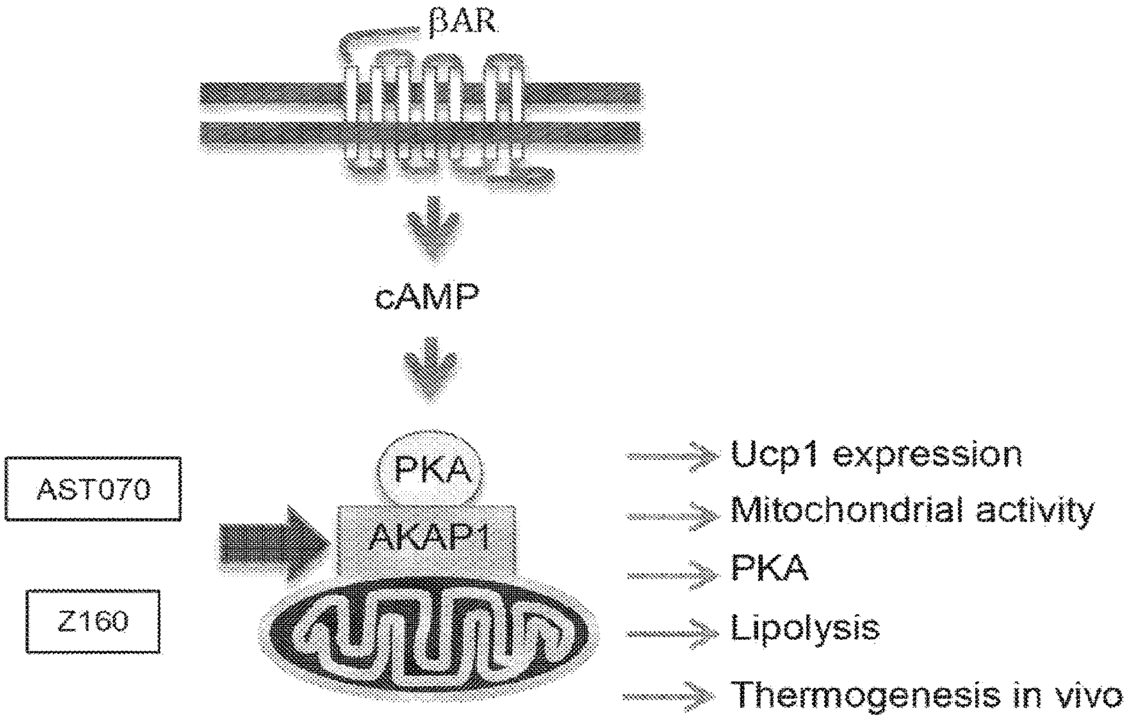
FIG. 11 is a schematic depicting how the compounds interact with and localize AKAP1 on mitochondria. The change in AKAP1/PKA subcellular localization seems to promote Ucp1 expression, mitochondrial and PKA activity, as well as lipolysis in brown and white adipocytes.

To further assess the requirement of AKAP1 to mediate the effects of Z160, AKAP1 was inactivated in an immortalized brown adipocyte cell line (AKAP1wt) using CRISPR/Cas9 gene editing. One clone (AKAP1mut) was selected based on very low AKAP1 protein levels (FIG. 10A). Unlike AKAP1wt cells, treatment of AKAP1mut cells did not respond to Z160 with increased Ucp1 expression (FIG. 10B). Additionally, the Z160-induced gene expression was blunted or reduced in AKAP1mut for Hoxa5, Cidea, Elovl3, Acox1, and Cpt1b. However, Z160 increased Ppargc1a expression in both AKAP1wt and AKAP1mut cells, suggesting that Z160 may exert some effects that are AKAP1-dependent, and others that are AKAP1-independent.

Example 10: Z160 Protects Against Hypertrophy in Cardiomyocytes

Figure 17A:
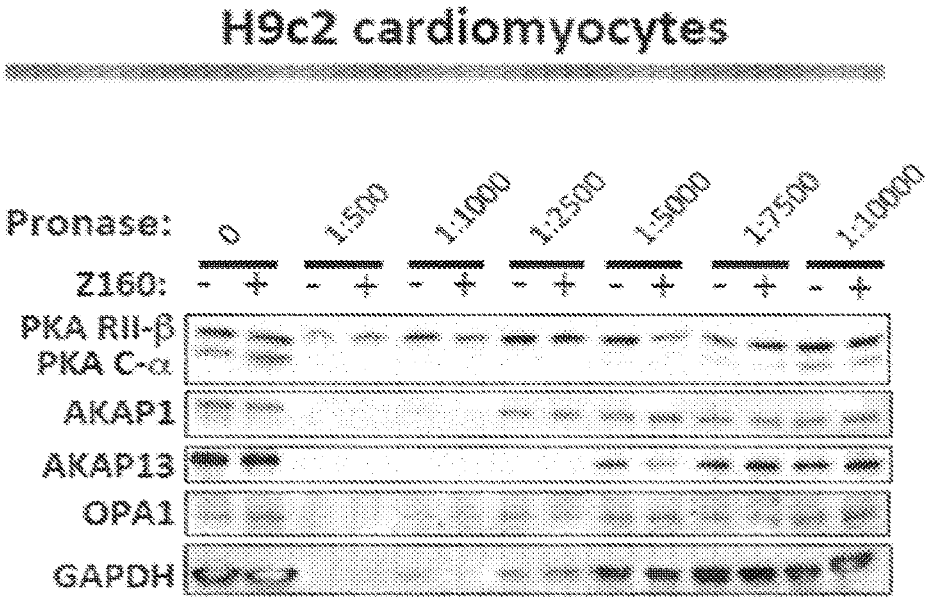
FIGS. 17A-17C depict how Z160 protects against hypertrophy in cardiomyocytes.
Figure 17B:
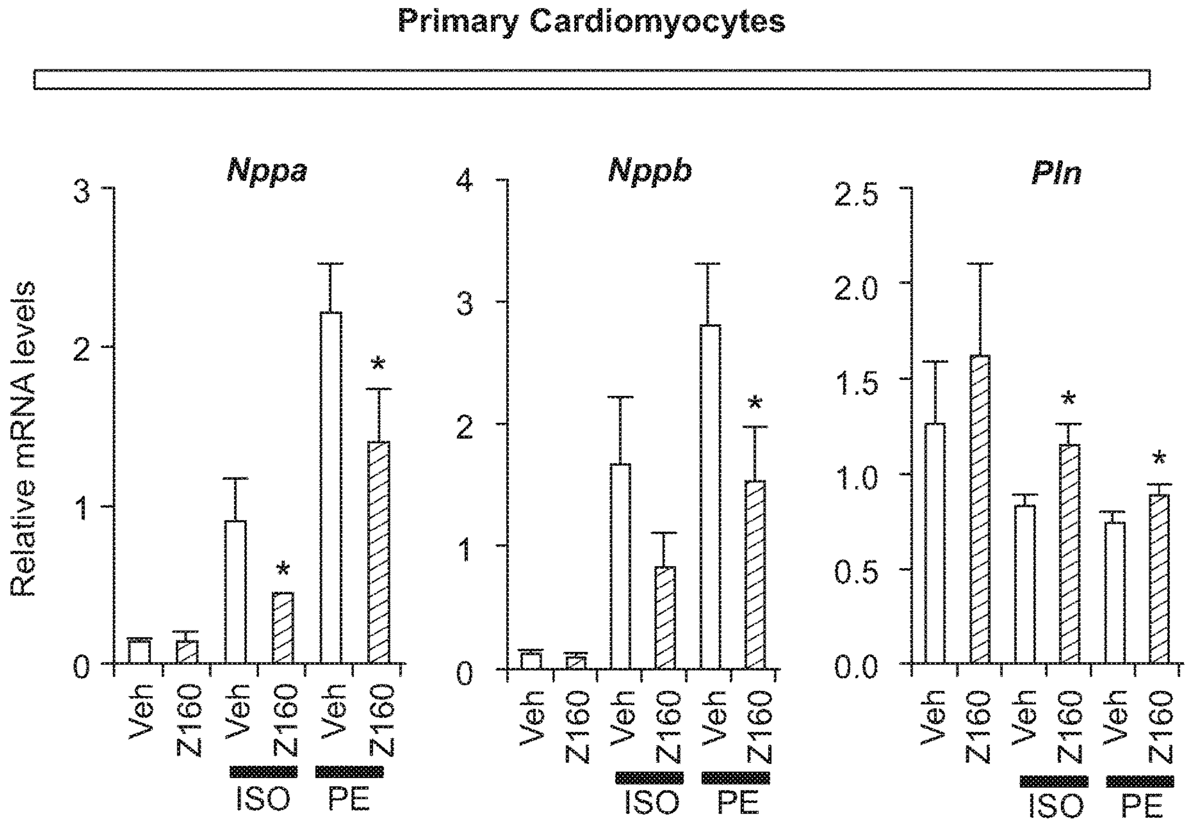
Figure 17C:
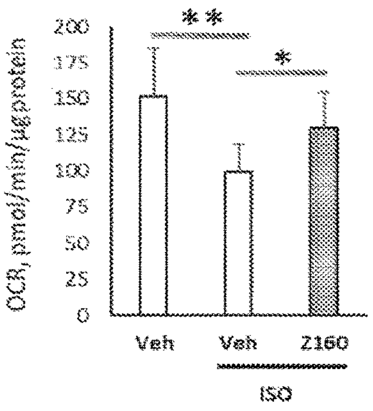

Cardiac hypertrophy affects mitochondrial respiration, especially reserve capacity. To determine whether Z160 mitigates this effect in an in vitro model of hypertrophy, NRVM were treated with isoproterenol (48 h with 100 μM isoproterenol followed by 24 h rest). As expected, isoproterenol decreased the reserve capacity of mitochondrial respiration in NRVM (FIG. 17C). Addition of Z160 for 24 h following isoproterenol treatment prevented reduction in reserve capacity (FIG. 17C). Z160 also prevented the induction of a hypertrophic gene expression profile in NRVM in response to β-adrenergic agonists, isoproterenol or phenylephrine. NRVM treated with isoproterenol or phenylephrine for 48 h induced the expression of natriuretic peptide A (Nppa) and natriuretic peptide B (Nppb), and reduced expression of phospholamban (Pln) (FIG. 17B). In contrast, treatment of NRVM with Z160 concomitantly with the β-adrenergic agonists mitigated the hypertrophic gene expression response (FIG. 17B). These results suggest that Z160 exhibits protective effects against cardiac hypertrophy-induced mitochondrial defects and gene expression patterns.

In brown adipocytes, AKAP1 was identified as a target of Z160 action. In heart, AKAP1 and AKAP13 have been implicated in protection from cardiac hypertrophy. It was investigated whether Z160 binds to AKAP1 or AKAP13 in cardiomyocytes. The DARTS assay was applied to H9c2 cells, a rat myocyte model of cardiac origin. AKAP13, but not AKAP1, had altered pronase susceptibility in the presence of Z160 (FIG. 17A). This provides evidence for Z160 interaction with AKAP13, and suggests that its action in cardiomyocytes may occur through an AKAP13/protein kinase A mechanism.

Further experimental procedures and results can be found in Vergnes, L; Lin, J. Y.; Davies, G. R.; Church, C. D.; Reue, K; Induction of UCP1 and thermogenesis by a small molecule via AKAP1/PKA modulation. *J. Biol. Chem.* 2020, 295(44), 15054-15069; which is hereby incorporated by reference herein in its entirety, and particularly for these experimental procedures and results.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

REFERENCES

[1] Twig, G., Yaniv, G., Levine, H., Leiba, A., Goldberger, N., Derazne, E., et al., 2016. Body-Mass Index in 2.3 Million Adolescents and Cardiovascular Death in Adulthood. New England Journal of Medicine 374(25): 2430-40, Doi: 10.1056/NEJMoa1503840.

[2] Juonala, M., Magnussen, C. G., Berenson, G. S., Venn, A., Burns, T. L., Sabin, M. A., et al., 2011. Childhood adiposity, adult adiposity, and cardiovascular risk factors. The New England Journal of Medicine 365(20): 1876-85, Doi: 10.1056/NEJMoa1010112.

[3] Galgani, J., Ravussin, E., 2008. Energy metabolism, fuel selection and body weight regulation. International Journal of Obesity 32(S7): S109-19, Doi: 10.1038/ijo.2008.246.

[4] Hill, J. O., Wyatt, H. R., Peters, J. C., 2012. Energy Balance and Obesity. Circulation 126(1): 126-32, Doi: 10.1161/CIRCULATIONAHA.111.087213.

[5] Kajimura, S., Saito, M., 2014. A New Era in Brown Adipose Tissue Biology: Molecular Control of Brown Fat Development and Energy Homeostasis. Annual Review of Physiology 76(1): 225-49, Doi: 10.1146/annurev-physiol-021113-170252.

[6] Giordano, A., Frontini, A., Cinti, S., 2016. Convertible visceral fat as a therapeutic target to curb obesity. Nature Reviews. Drug Discovery, Doi: 10.1038/nrd.2016.31.

[7] Wankhade, U. D., Shen, M., Yadav, H., Thakali, K. M., 2016. Novel Browning Agents, Mechanisms, and Therapeutic Potentials of Brown Adipose Tissue. BioMed Research International 2016: 1-15, Doi: 10.1155/2016/2365609.

[8] Betz, M. J., Enerbäck, S., 2018. Targeting thermogenesis in brown fat and muscle to treat obesity and metabolic disease. Nature Reviews. Endocrinology 14(2): 77-87, Doi: 10.1038/nrendo.2017.132.

[9] Nedergaard, J., Bengtsson, T., Cannon, B., 2007. Unexpected evidence for active brown adipose tissue in adult humans. American Journal of Physiology. Endocrinology and Metabolism 293(2): E444-52, Doi: 10.1152/ajpendo.00691.2006.

[10] Cypess, A. M., Lehman, S., Williams, G., Tal, I., Rodman, D., Goldfine, A. B., et al., 2009. Identification and importance of brown adipose tissue in adult humans The New England Journal of Medicine 360(15): 1509-17, Doi: 10.1056/NEJMoa0810780.

[11] van Marken Lichtenbelt, W. D., Vanhommerig, J. W., Smulders, N. M., Drossaerts, J. M. A. F. L., Kemerink, G. J., Bouvy, N. D., et al., 2009. Cold-activated brown adipose tissue in healthy men. The New England Journal of Medicine 360(15): 1500-8, Doi: 10.1056/NEJMoa0808718.

[12] Virtanen, K. A., Lidell, M. E., Orava, J., Heglind, M., Westergren, R., Niemi, T., et al., 2009. Functional Brown Adipose Tissue in Healthy Adults. New England Journal of Medicine 360(15): 1518-25, Doi: 10.1056/NEJMoa0808949.

[13] Sidossis, L. S., Porter, C., Saraf, M. K., Børsheim, E., Radhakrishnan, R. S., Chao, T., et al., 2015. Browning of Subcutaneous White Adipose Tissue in Humans after Severe Adrenergic Stress. Cell Metabolism 22(2): 219-27, Doi: 10.1016/j.cmet.2015.06.022.

[14] Kajimura, S., Spiegelman, B. M., Seale, P., 2015. Brown and Beige Fat: Physiological Roles beyond Heat Generation. Cell Metabolism 22(4): 546-59, Doi: 10.1016/j.cmet.2015.09.007.

[15] Wu, J., Boström, P., Sparks, L. M., Ye, L., Choi, J. H., Giang, A.-H., et al., 2012. Beige adipocytes are a distinct type of thermogenic fat cell in mouse and human. Cell 150(2): 366-76, Doi: 10.1016/j.cell.2012.05.016.

[16] Sharp, L. Z., Shinoda, K., Ohno, H., Scheel, D. W., Tomoda, E., Ruiz, L., et al., 2012. Human BAT possesses molecular signatures that resemble beige/brite cells. PloS One 7(11): e49452, Doi: 10.1371/journal.pone.0049452.

[17] Cannon, B., Nedergaard, J., 2004. Brown adipose tissue: function and physiological significance. Physiological Reviews 84(1): 277-359, Doi: 10.1152/physrev.00015.2003.

[18] Ricquier, D., 2011. Uncoupling Protein 1 of Brown Adipocytes, the Only Uncoupler: A Historical Perspective. Frontiers in Endocrinology 2: 85, Doi: 10.3389/fendo.2011.00085.

[19] Shi, F., Collins, S., 2017. Second messenger signaling mechanisms of the brown adipocyte thermogenic program: an integrative perspective. Hormone Molecular Biology and Clinical Investigation 0(0), Doi: 10.1515/hmbci-2017-0062.

[20] Collins, S., Yehuda-Shnaidman, E., Wang, H., 2010. Positive and negative control of Ucp1 gene transcription and the role of β-adrenergic signaling networks. International Journal of Obesity 34(S1): S28-33, Doi: 10.1038/ijo.2010.180.

[21] Villarroya, F., Peyrou, M., Giralt, M., 2017. Transcriptional regulation of the uncoupling protein-1 gene. Biochimie 134: 86-92, Doi: 10.1016/j.biochi.2016.09.017.

[22] Torres-Quesada, O., Mayrhofer, J. E., Stefan, E., 2017. The many faces of compartmentalized PKA signalosomes. Cellular Signalling 37: 1-11, Doi: 10.1016/j.cellsig.2017.05.012.

[23] Wong, W., Scott, J. D., 2004. AKAP signalling complexes: focal points in space and time. Nature Reviews. Molecular Cell Biology 5(12): 959-70, Doi: 10.1038/nrm1527.

[24] Rogne, M., Tasken, K., 2014. Compartmentalization of cAMP signaling in adipogenesis, lipogenesis, and lipolysis. Hormone and Metabolic Research=Hormon-Und Stoffwechselforschung=Hormones et Metabolisme 46(12): 833-40, Doi: 10.1055/s-0034-1389955.

[25] Calejo, A. I., Taskén, K., 2015. Targeting protein-protein interactions in complexes organized by A kinase anchoring proteins. Frontiers in Pharmacology 6: 192, Doi: 10.3389/fphar.2015.00192.

[26] Tröger, J., Moutty, M. C., Skroblin, P., Klussmann, E., 2012. A-kinase anchoring proteins as potential drug targets. British Journal of Pharmacology 166(2): 420-33, Doi: 10.1111/j.1476-5381.2011.01796.x.

[27] Thyagarajan, B., Foster, M. T., 2017. Beiging of white adipose tissue as a therapeutic strategy for weight loss in humans. Hormone Molecular Biology and Clinical Investigation 31(2), Doi: 10.1515/hmbci-2017-0016.

[28] Bonet, M. L., Oliver, P., Palou, A., 2013. Pharmacological and nutritional agents promoting browning of white adipose tissue. Biochimica et Biophysica Acta (BBA)—Molecular and Cell Biology of Lipids 1831(5): 969-85, Doi: 10.1016/j.bbalip.2012.12.002.

[29] Vergnes, L., Chin, R., Young, S. G., Reue, K., 2011. Heart-type Fatty Acid-binding Protein Is Essential for Efficient Brown Adipose Tissue Fatty Acid Oxidation and Cold Tolerance. Journal of Biological Chemistry 286(1): 380-90, Doi: 10.1074/jbc.M110.184754.

[30] Uldry, M., Yang, W., St-Pierre, J., Lin, J., Seale, P., Spiegelman, B. M., 2006. Complementary action of the PGC-1 coactivators in mitochondrial biogenesis and brown fat differentiation. Cell Metabolism 3(5): 333-41, Doi: 10.1016/j.cmet.2006.04.002.

[31] Xue, R., Lynes, M. D., Dreyfuss, J. M., Shamsi, F., Schulz, T. J., Zhang, H., et al., 2015. Clonal analyses and gene profiling identify genetic biomarkers of the thermogenic potential of human brown and white preadipocytes. Nature Medicine 21(7): 760-8, Doi: 10.1038/nm.3881.

[32] Plaisier, C. L., Bennett, B. J., He, A., Guan, B., Lusis, A. J., Reue, K., et al., 2012. Zbtb16 has a role in brown adipocyte bioenergetics. Nutrition & Diabetes 2(9): e46, Doi: 10.1038/nutd.2012.21.

[33] Vergnes, L., Davies, G. R., Lin, J. Y., Yeh, M. W., Livhits, M. J., Harari, A., et al., 2016. Adipocyte Browning and Higher Mitochondrial Function in Periadrenal But Not SC Fat in Pheochromocytoma. The Journal of Clinical Endocrinology & Metabolism 101(11): 4440-8, Doi: 10.1210/jc.2016-2670.

[34] Rogers, G. W., Brand, M. D., Petrosyan, S., Ashok, D., Elorza, A. A., Ferrick, D. A., et al., 2011. High throughput microplate respiratory measurements using minimal quantities of isolated mitochondria. PloS One 6(7): e21746, Doi: 10.1371/journal.pone.0021746.

[35] Schneider, C. A., Rasband, W. S., Eliceiri, K. W., 2012. NIH Image to ImageJ: 25 years of image analysis. Nature Methods 9(7): 671-5.

[36] Jafari, R., Almqvist, H., Axelsson, H., Ignatushchenko, M., Lundback, T., Nordlund, P., et al., 2014. The cellular thermal shift assay for evaluating drug target interactions in cells. Nature Protocols 9(9): 2100-22, Doi: 10.1038/nprot.2014.138.

[37] Lomenick, B., Jung, G., Wohlschlegel, J. A., Huang, J., 2011. Target Identification Using Drug Affinity Responsive Target Stability (DARTS). Current Protocols in Chemical Biology, vol. 3. Hoboken, NJ, USA: John Wiley & Sons, Inc. p. 163-80.

[38] de Jong, J. M. A., Larsson, O., Cannon, B., Nedergaard, J., 2015. A stringent validation of mouse adipose tissue identity markers. American Journal of Physiology. Endocrinology and Metabolism 308(12): E1085-105, Doi: 10.1152/ajpendo.00023.2015.

[39] Roh, H. C., Tsai, L. T. Y., Shao, M., Tenen, D., Shen, Y., Kumari, M., et al., 2018. Warming Induces Significant Reprogramming of Beige, but Not Brown, Adipocyte Cellular Identity. Cell Metabolism 27(5): 1121-1137.e5, Doi: 10.1016/j.cmet.2018.03.005.

[40] Huang, D. W., Sherman, B. T., Lempicki, R. A., 2009. Systematic and integrative analysis of large gene lists using DAVID bioinformatics resources. Nature Protocols 4(1): 44-57, Doi: 10.1038/nprot.2008.211.

[41] Cao, W., Daniel, K. W., Robidoux, J., Puigserver, P., Medvedev, A. V., Bai, X., et al., 2004. p38 mitogen-activated protein kinase is the central regulator of cyclic AMP-dependent transcription of the brown fat uncoupling protein 1 gene. Molecular and Cellular Biology 24(7): 3057-67.

[42] Robidoux, J., Cao, W., Quan, H., Daniel, K. W., Moukdar, F., Bai, X., et al., 2005. Selective Activation of Mitogen-Activated Protein (MAP) Kinase Kinase 3 and p38 MAP Kinase Is Essential for Cyclic AMP-Dependent UCP1 Expression in Adipocytes. Molecular and Cellular Biology 25(13): 5466-79, Doi: 10.1128/MCB.25.13.5466-5479.2005.

[43] Martinez Molina, D., Jafari, R., Ignatushchenko, M., Seki, T., Larsson, E. A., Dan, C., et al., 2013. Monitoring drug target engagement in cells and tissues using the cellular thermal shift assay. Science (New York, N.Y.) 341(6141): 84-7, Doi: 10.1126/science.1233606.

[44] Merrill, R. A., Strack, S., 2014. Mitochondria: a kinase anchoring protein 1, a signaling platform for mitochondrial form and function. The International Journal of Biochemistry & Cell Biology 48: 92-6, Doi: 10.1016/j.biocel.2013.12.012.

[45] Carlucci, A., Lignitto, L., Feliciello, A., 2008. Control of mitochondria dynamics and oxidative metabolism by cAMP, AKAPs and the proteasome. Trends in Cell Biology 18(12): 604-13, Doi: 10.1016/j.tcb.2008.09.006.

[46] Valsecchi, F., Ramos-Espiritu, L. S., Buck, J., Levin, L. R., Manfredi, G., 2013. cAMP and Mitochondria. Physiology 28(3): 199-209, Doi: 10.1152/physiol.00004.2013.

[47] Papa, S., Scacco, S., De Rasmo, D., Signorile, A., Papa, F., Panelli, D., et al., 2010. cAMP-dependent protein kinase regulates post-translational processing and expression of complex I subunits in mammalian cells. Biochimica et Biophysica Acta (BBA)—Bioenergetics 1797(6-7): 649-58, Doi: 10.1016/j.bbabio.2010.03.013.

[48] Acin-Perez, R., Gatti, D. L., Bai, Y., Manfredi, G., 2011. Protein Phosphorylation and Prevention of Cytochrome Oxidase Inhibition by ATP: Coupled Mechanisms of Energy Metabolism Regulation. Cell Metabolism 13(6): 712-9, Doi: 10.1016/j.cmet.2011.03.024.

[49] Chaudhry, A., Zhang, C., Granneman, J. G., 2002. Characterization of RII(beta) and D-AKAP1 in differentiated adipocytes. American Journal of Physiology. Cell Physiology 282(1): C205-12, Doi: 10.1152/ajpcell.2002.282.1.C205.

[50] Clapham, J. C., 2004. Treating obesity: pharmacology of energy expenditure. Current Drug Targets 5(3): 309-23.

[51] Gaundar, S. S., Bendall, L. J., 2010. The potential and limitations of p38MAPK as a drug target for the treatment of hematological malignancies. Current Drug Targets 11(7): 823-33.

[52] Wright, M. B., Bortolini, M., Tadayyon, M., Bopst, M., 2014. Minireview: Challenges and Opportunities in Development of PPAR Agonists. Molecular Endocrinology 28(11): 1756-68, Doi: 10.1210/me.2013-1427.

[53] Psaty, B. M., Furberg, C. D., 2007. Rosiglitazone and Cardiovascular Risk. New England Journal of Medicine 356(24): 2522-4, Doi: 10.1056/NEJMe078099.

[54] Bridges, D., MacDonald, J. A., Wadzinski, B., Moorhead, G. B. G., 2006. Identification and characterization of D-AKAP1 as a major adipocyte PKA and PP1 binding protein. Biochemical and Biophysical Research Communications 346(1): 351-7, Doi: 10.1016/j.bbrc.2006.05.138.

[55] Schiattarella G G, Boccella N, Paolillo R, Cattaneo F, Trimarco V, Franzone A, D'Apice S, Giugliano G, Rinaldi L, Borzacchiello D, Gentile A, Lombardi A, Feliciello A, Esposito G, Perrino C., 2018. Loss of Akap1 Exacerbates Pressure Overload-Induced Cardiac Hypertrophy and Heart Failure. Front Physiol. 9:558. doi: 10.3389/fphys.2018.00558.

[56] Appert-Collin, A., Cotecchia, S., Nenniger-Tosato, M., Pedrazzini, T., Diviani, D., 2007. The A-kinase anchoring protein (AKAP)-Lbc-signaling complex mediates alpha1 adrenergic receptor-induced cardiomyocyte hypertrophy. Proceedings of the National Academy of Sciences of the United States of America 104(24): 10140-5, Doi: 10.1073/pnas.0701099104.

What is claimed is:

1. A method of treating or preventing a condition, comprising administering to a subject in need thereof an effective amount of a compound of formula (Ia):

(Ia)

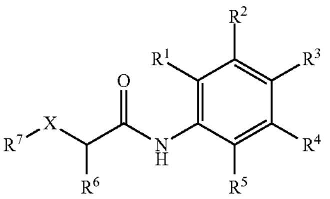

or a tautomer and/or salt thereof;

wherein:

X is S or $CH_2$;

$R^1$ is H, $C_{1-3}$ alkyl, or $C_{1-3}$ alkoxy;

$R^2$ is H or $C_{1-3}$ alkoxy;

$R^3$ is H, $C_{1-3}$ alkoxy, phenoxy, or benzyloxy;

$R^4$ is H, hydroxyl, $C_{1-3}$ alkoxy, or $C_{1-3}$ haloalkoxy;

or $R^3$ and $R^4$ combine to form a dioxane or dioxolane ring, including the atoms to which $R^3$ and $R^4$ are attached;

$R^5$ is H or $C_{1-3}$ alkyl;

$R^6$ is H;

$R^7$ is a quinazolin-4-on-2-yl group

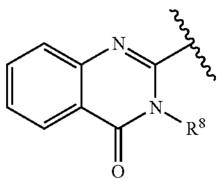

, wherein the phenyl ring of the quinazolin-4-on-2-yl group may be substituted or unsubstituted; and $R^8$ is H, $C_{1-5}$ alkyl, $C_{1-5}$ alkenyl, or amino;

wherein the condition is selected from obesity and associated complex metabolic, endocrine, and hemodynamic changes, dyslipidemias, cardiovascular disease, and type 2 diabetes.

2. The method of claim 1, wherein:

$R^1$ is H, $CH_3$, methoxy, or ethoxy;

$R^2$ is H or methoxy;

$R^3$ is H, methoxy, ethoxy, phenoxy, or benzyloxy;

$R^4$ is H, methoxy, ethoxy, tetrafluoroethoxy, or hydroxyl;

or $R^3$ and $R^4$ combine to form a dioxane or dioxolane ring, including the atoms to which $R^3$ and $R^4$ are attached; and $R^5$ is H or methyl.

3. The method of claim 2, wherein:

$R^2$ is H;

$R^3$ is H, methoxy, ethoxy, or phenoxy; and $R^4$ is H, methoxy, tetrafluoroethoxy, or hydroxyl;

or $R^3$ and $R^4$ combine to form a dioxane or dioxolane ring including the atoms to which $R^3$ and $R^4$ are attached.

4. The method of claim 3, wherein the compound of formula (Ia) is selected from:

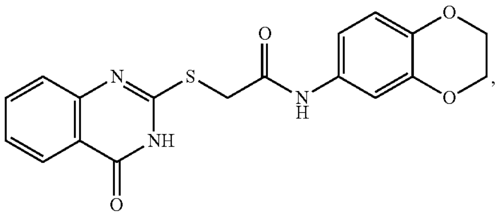

,

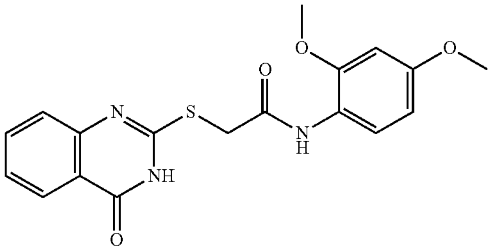

,

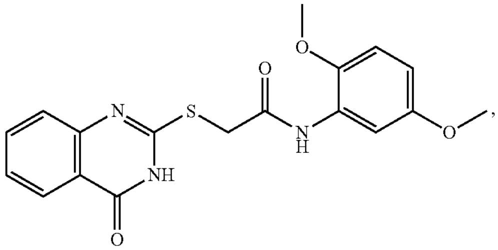

,

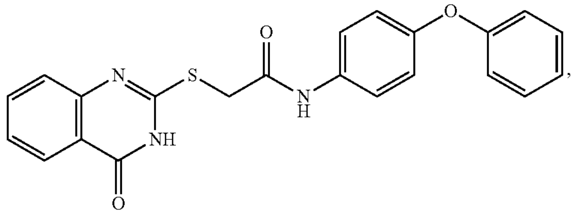

,

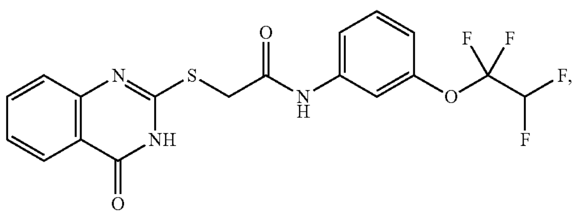

,

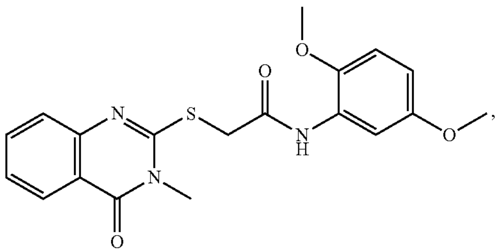

,

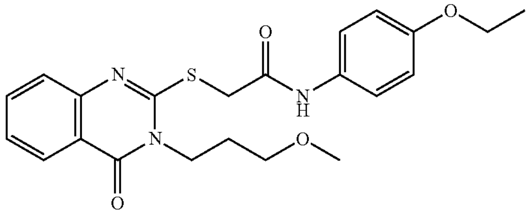

,

-continued
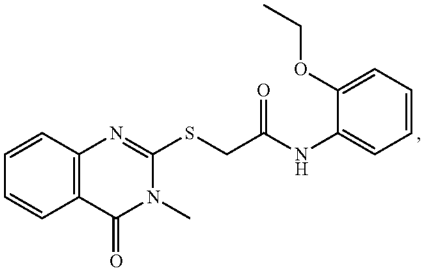
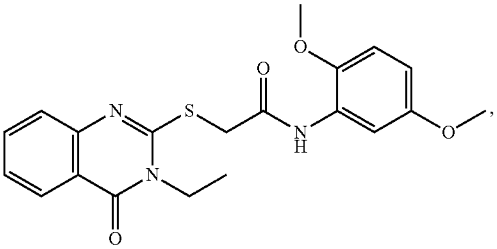
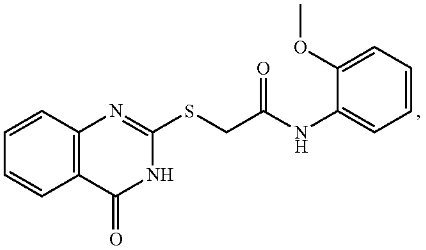
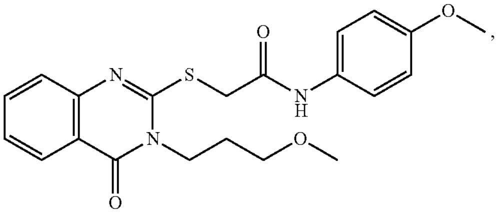
and
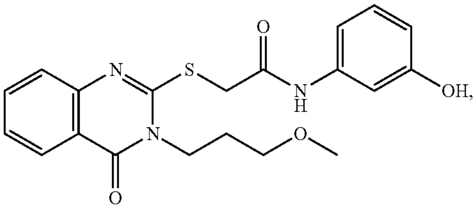
or a tautomer and/or salt thereof.
5. The method of claim 2, wherein:
$R^7$ is
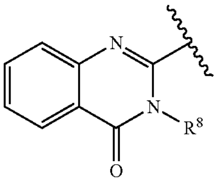
;
and
$R^8$ is H, $CH_3$, ethyl, methoxypropyl, or amino.
6. The method of claim 5, wherein the compound of formula (Ia) is selected from:
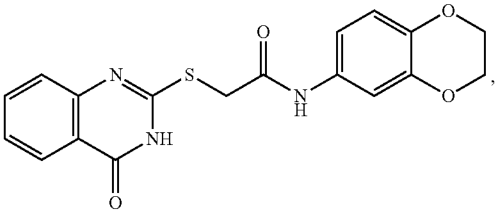
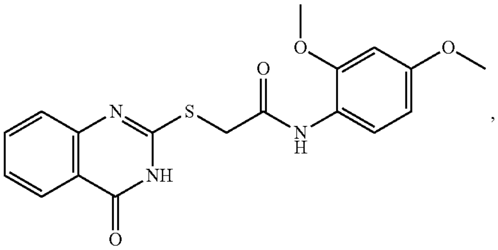
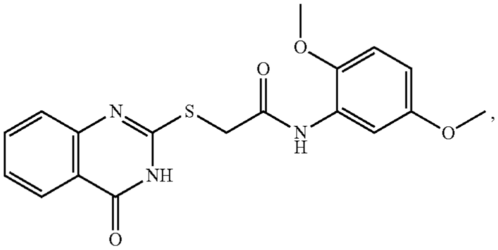
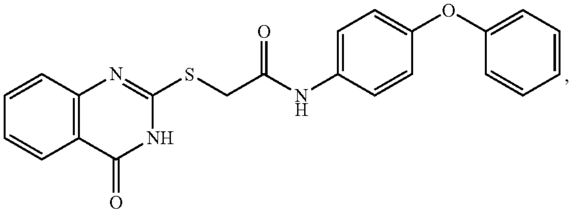
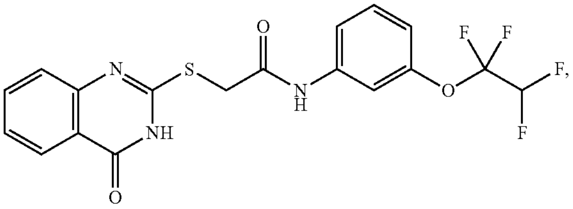
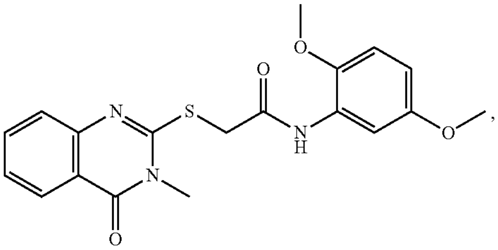
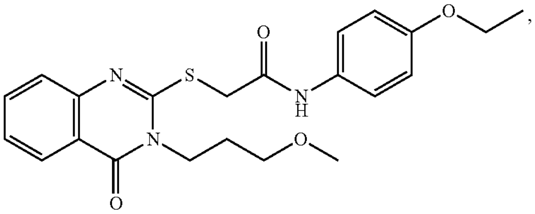

-continued

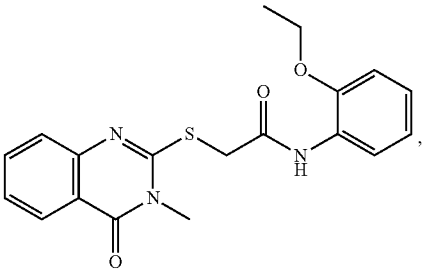

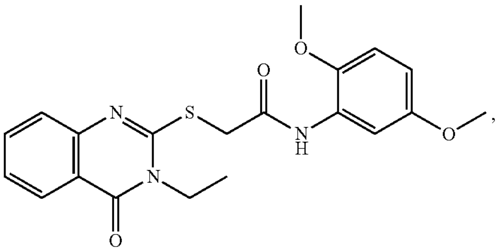

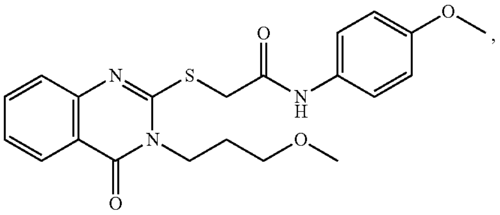

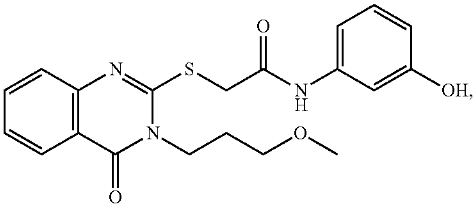

and

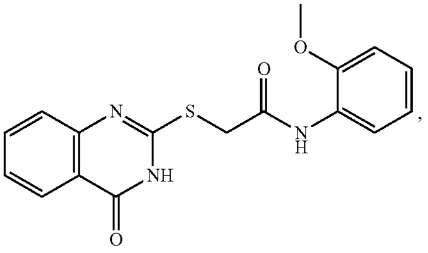

or a tautomer and/or salt thereof.

7. The method of claim 5, wherein the compound of formula (Ia) is a compound of formula (Ib):

(Ib)

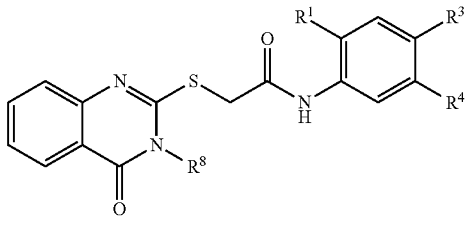

or a tautomer or salt thereof; wherein:

$R^1$ is H or methoxy;

$R^3$ is H or methoxy, and $R^4$ is H or methoxy, or $R^3$ and $R^4$ combine to form a dioxane or dioxolane ring including the atoms to which $R^3$ and $R^4$ are attached;

and $R^8$ is H or $C_{1-3}$ alkyl.

8. The method of claim 7, wherein the compound of formula (Ib) is selected from:

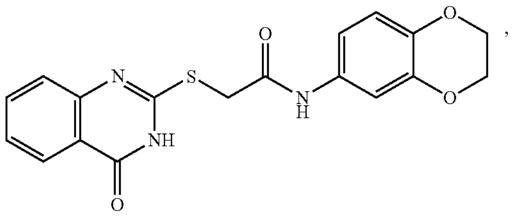

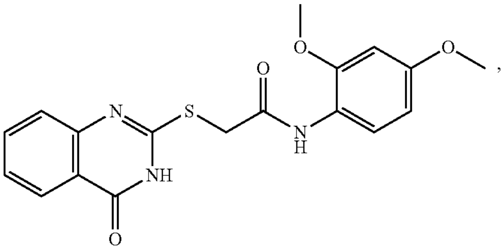

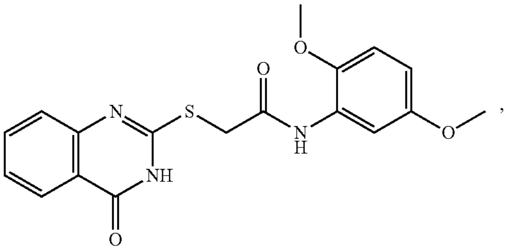

and

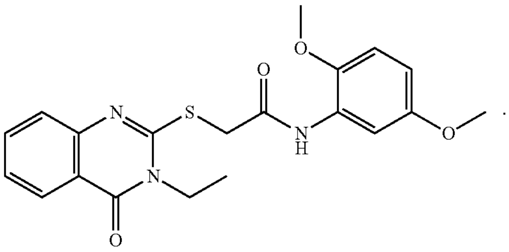

or a tautomer and/or salt thereof.

9. The method of claim 5, wherein the compound of formula (Ia) is

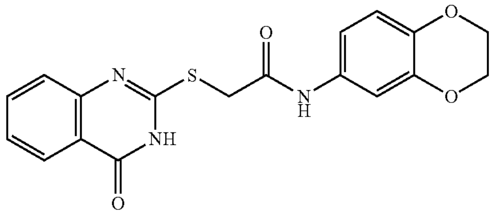

-continued or

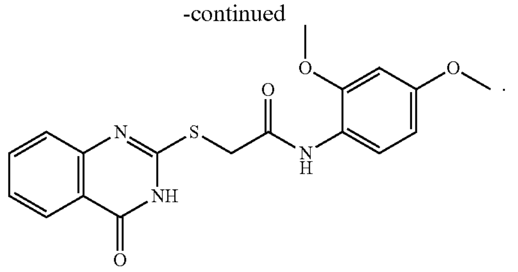

or a tautomer and/or salt thereof.

10. The method of claim 9, wherein the compound of formula (Ia) is

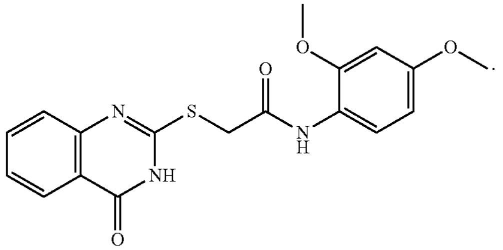 [SMILES: COc1ccc(NC(=O)CSc2nc3ccccc3c(=O)[nH]2)c(OC)c1]

or a tautomer and/or salt thereof.

11. A method of administering a β-adrenergic agonist to a patient, comprising conjointly administering the β-adrenergic agonist with a compound of formula (Ia):

(Ia)

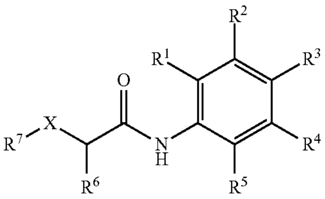

or a tautomer and/or salt thereof;

wherein:

X is S or $CH_2$;

$R^1$ is H, $C_{1-3}$ alkyl, or $C_{1-3}$ alkoxy;

$R^2$ is H or $C_{1-3}$ alkoxy;

$R^3$ is H, $C_{1-3}$ alkoxy, phenoxy, or benzyloxy;

$R^4$ is H, hydroxyl, $C_{1-3}$ alkoxy, or $C_{1-3}$ haloalkoxy;

or $R^3$ and $R^4$ combine to form a dioxane or dioxolane ring, including the atoms to which $R^3$ and $R^4$ are attached;

$R^5$ is H or $C_{1-3}$ alkyl;

$R^6$ is H;

$R^7$ is a quinazolin-4-on-2-yl group,

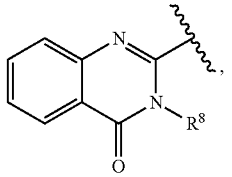

wherein the phenyl ring of the quinazolin-4-on-2-yl group may be substituted or unsubstituted; and $R^8$ is H, $C_{1-5}$ alkyl, $C_{1-5}$ alkenyl, or amino.

12. A method of reducing β-adrenergic agonist-induced cardiac hypertrophy, comprising administering, to a patient receiving a β-adrenergic agonist, a compound of formula (Ia):

(Ia)

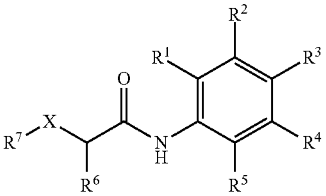

or a tautomer and/or salt thereof;

wherein:

X is S or $CH_2$;

$R^1$ is H, $C_{1-3}$ alkyl, or $C_{1-3}$ alkoxy;

$R^2$ is H or $C_{1-3}$ alkoxy;

$R^3$ is H, $C_{1-3}$ alkoxy, phenoxy, or benzyloxy;

$R^4$ is H, hydroxyl, $C_{1-3}$ alkoxy, or $C_{1-3}$ haloalkoxy;

or $R^3$ and $R^4$ combine to form a dioxane or dioxolane ring, including the atoms to which $R^3$ and $R^4$ are attached;

$R^5$ is H or $C_{1-3}$ alkyl;

$R^6$ is H;

$R^7$ is a quinazolin-4-on-2-yl group,

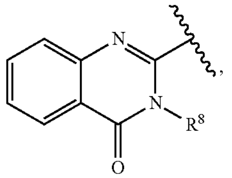

wherein the phenyl ring of the quinazolin-4-on-2-yl group may be substituted or unsubstituted; and $R^8$ is H, $C_{1-5}$ alkyl, $C_{1-5}$ alkenyl, or amino.

13. The method of claim 11, wherein the compound of formula (Ia) is selected from:

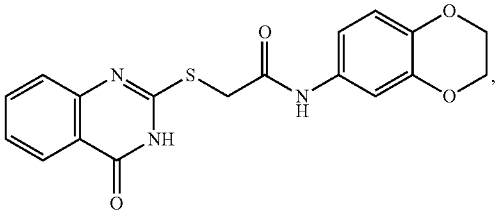

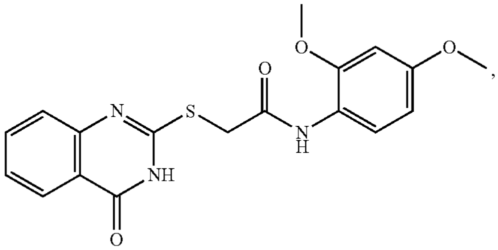

-continued

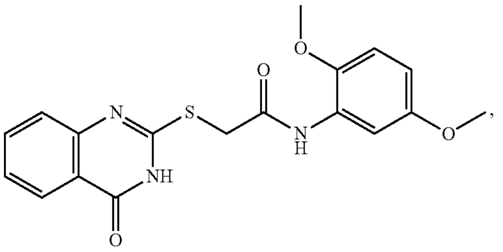

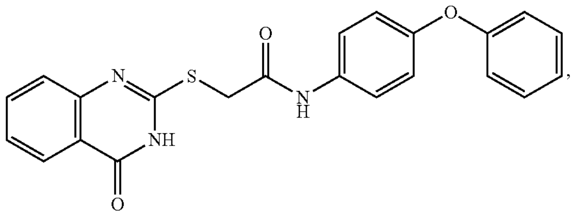

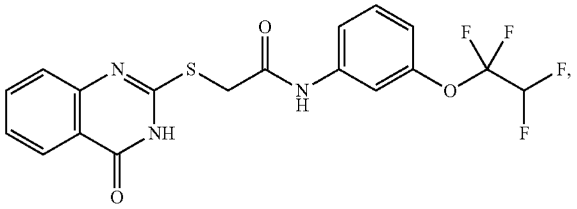

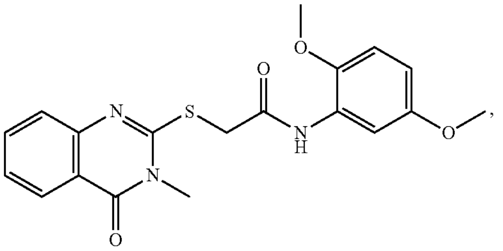

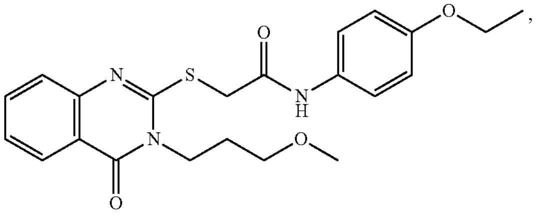

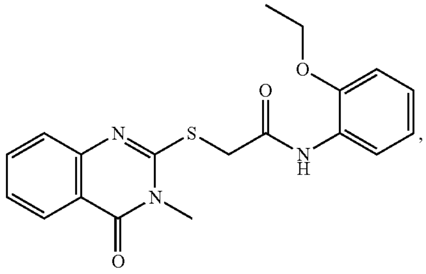

-continued

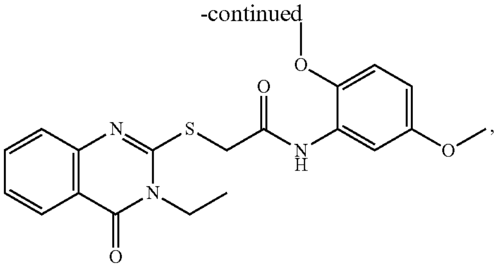

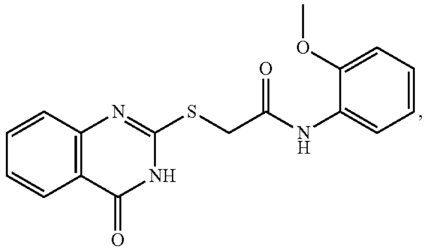

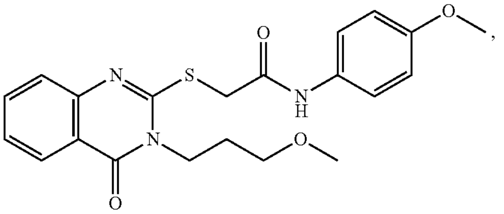

and

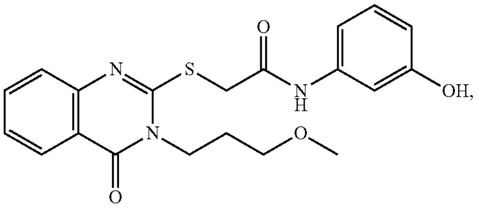

or a tautomer and/or salt thereof.

14. The method of claim 11, wherein the β-adrenergic agonist is selected from isoproterenol, phenylephrine, denopamine, dobutamine, dopexamine, epinephrine, prenalterol, xamoterol, Arformoterol, Buphenine, Clenbuterol, Dopexamine, Epinephrine, Fenoterol, Formoterol, Isoetarine, Isoprenaline, Levosalbutamol, levalbuterol, Orciprenaline, metaproterenol, Pirbuterol, Procaterol, Ritodrine, Salbutamol, albuterol, Salmeterol, Terbutaline, Arbutamine, Befunolol, Bromoacetylalprenololmenthane, Broxaterol, Cimaterol, Cirazoline, Etilefrine, Hexoprenaline, Higenamine, Isoxsuprine, Mabuterol, Methoxyphenamine, Oxyfedrine, Ractopamine, Reproterol, Rimiterol, Tretoquinol, Tulobuterol, Zilpaterol, Zinterol, CL316,243, Rafabegron, Mirabegron, Solabegron, Amibegron, Talibegron, and L-796568.

15. The method of claim 14, wherein the β-adrenergic agonist is selected from isoproterenol and phenylephrine.

* * * * *

SEQUENCE LISTING

<160> NUMBER OF SEQ ID NOS: 49

<210> SEQ ID NO 1
<211> LENGTH: 23
<212> TYPE: DNA
<213> ORGANISM: Mus musculus

<400> SEQUENCE: 1
cttgatgtgt ggagctgagt agc 23

<210> SEQ ID NO 2
<211> LENGTH: 21
<212> TYPE: DNA
<213> ORGANISM: Mus musculus

<400> SEQUENCE: 2
gtgccgtcac taacagtact g 21

<210> SEQ ID NO 3
<211> LENGTH: 21
<212> TYPE: DNA
<213> ORGANISM: Mus musculus

<400> SEQUENCE: 3
ctgcagactc ctgacacagc t 21

<210> SEQ ID NO 4
<211> LENGTH: 27
<212> TYPE: DNA
<213> ORGANISM: Mus musculus

<400> SEQUENCE: 4
ggaaagtggt tcagtttgat tagaagg 27

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 5
ctaggtagtg ccagtgcaga g 21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6
gggcccttgt aaacaacaaa 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 7
gtcggtcctt ccttggtgta 20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
aacctcaaga tccacaaaag ga 22

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
cctcgaactc gcacttgaa 19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
caagctgcac attagtcacg 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 11
ggtagcggtt gaagtggaat 20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12
ctcacagaga cactggacag t 21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
tgtagctgag ctgagtgttg g 21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
atcacaactg gcctggttac g 21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
tactacccgg tgtccatttc t 21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
gatggttctg ggcaccatct t 21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
cgttgttgtg tggcatcctt 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
caggaagagc aaggaagtgg 20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
cctttctggc tgatcccata 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
gtcgcttctt caaggtctgg 20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
aagaaagcag cacgttcgat 20

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
cgctgtgatg agtgtgatga g 21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
cgtgtggacg atcatgtgtt g 21

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
cttgcatagg tccagcgaat 20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
ggcttaaacg ggagtatctg c 21

-continued

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
actgtactgg cggcacaaat 20

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
gagggaatcc ggaggaga 18

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
tgacacataa gcgggtctga 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
catggcggtt ctcttaaagc 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
ccagtcttat gcttgcctcc 20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
ggacgtctgt cttcgagtcc 20

<210> SEQ ID NO 32

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32

gaagagccag cacaaaggtc                                                  20


<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33

ggctctgcct ctaaaggtcc                                                  20


<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34

caacaaagga tgaccccaaa                                                  20


<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

aagctgcaag gatgctgtct                                                  20


<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

tcgtgtttca gacggagaga a                                                21


<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

cagacattgg cctggatgag                                                  20


<210> SEQ ID NO 38
<211> LENGTH: 20
```

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 38
ggaactaagt ggacgcaagc 20

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 39
ccagggctgc ctcagacac 19

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 40
acctggagat cagggaggat 20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
gtcctccagc agcagttctc 20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
cagcatggct cgctcggtga c 21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 43
cgtagcagtt cagtatgttc g 21

<210> SEQ ID NO 44
<211> LENGTH: 23
<212> TYPE: DNA

-continued

<213> ORGANISM: Artificial Sequence
<220> FEATURE:
<223> OTHER INFORMATION: Description of Artificial Sequence: Synthetic oligonucleotide

<400> SEQUENCE: 44
acccttcacc aatgactcct atg 23

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
atgatgactg cagcaaatcg c 21

<210> SEQ ID NO 46
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 46
gagggggcaa guaacccgag 20

<210> SEQ ID NO 47
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 47
acuggcucca caaagcuacu 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
gcaagagtct tcaagccccg 20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
ggagaagagg tgagccatgg 20